United States Patent
Campbell et al.

(10) Patent No.: US 7,423,037 B2
(45) Date of Patent: Sep. 9, 2008

(54) MORPHOLINE DERIVATIVES AS NOREPINEPHRINE REUPTAKE INHIBITORS

(75) Inventors: Gordon Iain Campbell, Basingstoke (GB); Manuel Javier Cases-Thomas, Basingstoke (GB); Teresa Man, Basingstoke (GB); John Joseph Masters, Fishers, IN (US); Hélène Catherine Eugénie Rudyk, Basingstoke (GB); Magnus Wilhelm Walter, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 250 days.

(21) Appl. No.: 10/577,841

(22) PCT Filed: Oct. 28, 2004

(86) PCT No.: PCT/US2004/032771

§ 371 (c)(1),
(2), (4) Date: Apr. 29, 2006

(87) PCT Pub. No.: WO2005/047272

PCT Pub. Date: May 26, 2005

(65) Prior Publication Data

US 2007/0083046 A1    Apr. 12, 2007

(30) Foreign Application Priority Data

Nov. 10, 2003  (GB) .................................. 0326148.4

(51) Int. Cl.
*A61K 31/535* (2006.01)
*C07D 413/06* (2006.01)

(52) U.S. Cl. .................................. 514/231.5; 544/149

(58) Field of Classification Search ................. 544/149; 514/231.5
See application file for complete search history.

(56) References Cited

U.S. PATENT DOCUMENTS 7,354,920 B2    4/2008    Cases-Thomas

FOREIGN PATENT DOCUMENTS

| FR | 2 852 954 | 10/2004 |
| JP | 2004 277318 | 10/2004 |
| WO | WO 99/37305 | 7/1999 |
| WO | WO 01/00214 | 1/2001 |
| WO | WO 01/01973 | 1/2001 |
| WO | WO 03/018576 | 3/2003 |
| WO | WO 2004/018441 | 3/2004 |
| WO | WO 2004/087647 | 10/2004 |

OTHER PUBLICATIONS

Morilak et al., Progress in Neuro-Psychopharmacology & Biology Psychiatry, 29(2005), pp. 1214-1224.*

Kato, Shiro, et al., "1-(1-Substituted-4-piperidinylmethyl)piperidine derivatives as 5-TH4 receptor agonists, pharmaceutical compositions containing them, and their use," XP002317575, Database CA 'Online! Chemical Abstracts Service, Columbus, Ohio, US, retrieved from STN Database accession No. 2004:819908 abstract.

King, Frank, et al., "The synthesis of 2-morpholinecarboxylic acid derivatives and their elaboration to 1-aza-4-oxabicyclo'3.3.1!nonan-6-one", *Tetrahedron Letters*, 32(20):2281-4, 1991.

* cited by examiner

*Primary Examiner*—Rebecca L Anderson
(74) *Attorney, Agent, or Firm*—Thomas E. Jackson; Charles E. Cohen

(57) ABSTRACT

Compounds of the general formula (I) are inhibitors of the reuptake of norepinephrine. As such, they may be useful for the treatment of disorders of the central and/or peripheral nervous system.

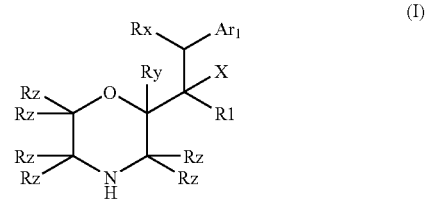

8 Claims, No Drawings

MORPHOLINE DERIVATIVES AS NOREPINEPHRINE REUPTAKE INHIBITORS

This invention relates to novel morpholine compounds, and to their use in selectively inhibiting norepinephrine reuptake.

Selective inhibition of norepinephrine reuptake is a relatively new mode of action for the treatment of affective disorders. Norepinephrine appears to play an important role in the disturbances of vegetative function associated with affective, anxiety and cognitive disorders. Atomoxetine hydrochloride is a selective inhibitor of norepinephrine reuptake, and is marketed for the treatment of attention deficit hyperactivity disorder (ADHD). Reboxetine is also a selective norepinephrine reuptake inhibitor, and is marketed for the treatment of depression. WO99/15177 discloses the use of reboxetine to treat ADHD and WO01/01973 discloses the use of S,S-reboxetine to treat inter alia ADHD. WO2004/018441 discloses certain morpholine derivatives as selective inhibitors of the reuptake of norepinephrine.

According to the present invention there is provided a compound of formula (I)

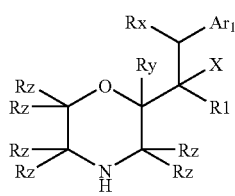

wherein,

X is OH, C1-C4 alkoxy, $NH_2$ or NH(C1-C4 alkyl);
Rx is H or C1-C4 alkyl;
Ry is H or C1-C4 alkyl;
each Rz group is independently H or C1-C4 alkyl, with the proviso that not more than 3 Rz groups may be C1-C4 alkyl;
R1 is C1-C6 alkyl (optionally substituted with 1, 2 or 3 halogen atoms and/or with 1 substituent selected from C1-C4 alkylthio (optionally substituted with 1, 2 or 3 fluorine atoms), C1-C4 alkoxy (optionally substituted with 1, 2 or 3 fluorine atoms), C3-C6 cycloalkoxy, C1-C4 alkylsulfonyl, cyano, —CO—O(C1-C2 alkyl), —O—CO—(C1-C2 alkyl) and hydroxy); C2-C6 alkenyl (optionally substituted with 1, 2 or 3 halogen atoms); C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C, S—C or C=C bond; C4-C7 cycloalkylalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C, S—C or C=C bond; or $CH_2Ar2$; and Ar1 and Ar2 are each independently a phenyl ring or a 5- or 6-membered heteroaryl ring each of which is optionally substituted with 1, 2 or 3 substituents (depending upon the number of available substitution positions) each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), —CO—O(C1-C4 alkyl), cyano, —NRR, —CONRR, halo and hydroxy and/or with 1 substituent selected from pyridyl, thiophenyl, phenyl, benzyl and phenoxy each of which is optionally ring-substituted with 1, 2 or 3 substituents each independently selected from halogen, C1-C4 alkyl (optionally substituted with 1, 2 or 3 halogen atoms), C1-C4 alkoxy (optionally substituted with 1, 2 or 3 halogen atoms), carboxy, nitro, hydroxy, cyano, —NRR, —CONRR, $SO_2NRR$ and $SO_2R$; and each R is independently H or C1-C4 alkyl;

or a pharmaceutically acceptable salt thereof.

In the present specification the term "C1-C4 alkyl" means a monovalent unsubstituted saturated straight-chain or branched-chain hydrocarbon radical having from 1 to 4 carbon atoms. Thus the term "C1-C4 alkyl" includes, for example, methyl, ethyl, n-propyl, isopropyl, n-butyl, isobutyl, sec-butyl and tert-butyl.

In the present specification the term "C1-C4 alkoxy" means a monovalent unsubstituted saturated straight-chain or branched-chain hydrocarbon radical having from 1 to 4 carbon atoms linked to the point of substitution by a divalent O radical. Thus the term "C1-C4 alkoxy" includes, for example, methoxy, ethoxy, n-propoxy, isopropoxy, n-butoxy, isobutoxy, sec-butoxy and tert-butoxy.

In the present specification the term "C1-C4 alkylthio" means a monovalent unsubstituted saturated straight-chain or branched-chain hydrocarbon radical having from 1 to 4 carbon atoms linked to the point of substitution by a divalent S radical. Thus the term "C1-C4 alkylthio" includes, for example, methylthio, ethylthio, n-propylthio, isopropylthio, n-butylthio, isobutylthio, sec-butylthio and tert-butylthio.

In the present specification the term "C3-C6 cycloalkyl" means a monovalent unsubstituted saturated cyclic hydrocarbon radical having from 3 to 6 carbon atoms. Thus the term "C3-C6 cycloalkyl" includes, for example, cyclopropyl, cyclobutyl, cyclopentyl and cyclohexyl.

In the present specification the term "C4-C7 cycloalkylalkyl" means a monovalent unsubstituted saturated cyclic hydrocarbon radical having from 3 to 6 carbon atoms linked to the point of substitution by a divalent unsubstituted saturated straight-chain or branched-chain hydrocarbon radical having at least 1 carbon atom. Thus the term "C4-C7 cycloalkyl" includes, for example, cyclopropylmethyl, cyclopropylethyl, cyclobutylmethyl, cyclopentylmethyl and cyclohexylmethyl.

In the present specification the phrase "wherein one C—C bond within the cycloalkyl moiety is optionally substituted by an O—C, S—C or C=C bond" means that either (i) any two adjacent carbon atoms within a cycloalkyl ring may be linked by a double bond rather than a single bond (with the number of substituents on each carbon atom being reduced accordingly), or that (ii) one of any two adjacent C atoms within a cycloalkyl ring (and any substituents thereon) may be replaced by an oxygen or sulphur atom.

Examples of groups encompassed by this phrase when used in conjunction with the term C3-C6 cycloalkyl include, for example:

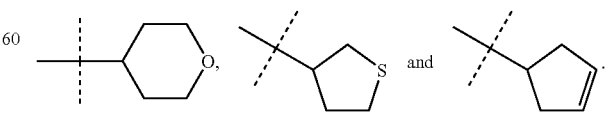

Examples of groups encompassed by this phrase when used in conjunction with the term C4-C7 cycloalkylalkyl include, for example:

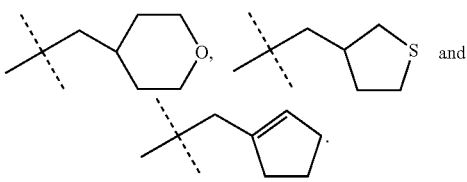

In the present specification the term "C2-C6 alkenyl" means a monovalent unsubstituted unsaturated straight-chain or branched-chain hydrocarbon radical having from 2 to 6 carbon atoms and containing at least one carbon-carbon double bond. Thus the term "C1-C4 alkenyl" includes, for example, ethenyl, propenyl, 2-methyl-2-propenyl and butenyl.

In the present specification the term "C3-C6 cycloalkoxy" means a monovalent unsubstituted saturated cyclic hydrocarbon radical having from 3 to 6 carbon atoms in the ring linked to the point of substitution by a divalent O radical. Thus the term "C3-C6 cycloalkoxyl" includes, for example, cyclopropoxy.

In the present specification the term "C1-C4 alkylsulfonyl" means a monovalent unsubstituted saturated straight-chain or branched-chain hydrocarbon radical having from 1 to 4 carbon atoms linked to the point of substitution by a divalent $SO_2$ radical. Thus the term "C1-C4 alkylsulfonyl" includes, for example, methylsulfonyl.

In the present specification terms similar to the above definitions specifying different numbers of C atoms take an analogous meaning. Specifically, "C1-C6 alkyl" means a monovalent unsubstituted saturated straight-chain or branched-chain hydrocarbon radical having from 1 to 6 carbon atoms. Thus the term "C1-C6 alkyl" represents a larger set of compounds that encompasses the subset "C1-C4 alkyl" but also includes, for example, n-pentyl, 3-methyl-butyl, 2-methyl-butyl, 1-methyl-butyl, 2,2-dimethyl-propyl, n-hexyl, 4-methyl-pentyl and 3-methyl-pentyl. Specifically, "C1-C2 alkyl" means a monovalent unsubstituted saturated hydrocarbon radical having 1 or 2 carbon atoms. Thus the term "C1-C2 alkyl" represents a subset of compounds within the term "C1-C4 alkyl" and includes methyl and ethyl.

In the present specification the term "halo" or "halogen" means F, Cl, Br or I.

In the present specification the term "phenoxy" means a monovalent unsubstituted phenyl radical linked to the point of substitution by a divalent O radical.

In the present specification the term "5-membered heteroaryl ring" means a 5-membered aromatic ring including one or more heteroatoms each independently selected from N, O and S. Preferably there are not more than three heteroatoms in total in the ring. More preferably there are not more than two heteroatoms in total in the ring. More preferably there is not more than one heteroatom in total in the ring. The term includes, for example, the groups thiazolyl, isothiazolyl, oxazolyl, isoxazolyl, thiophenyl, furanyl, pyrrolyl, imidazolyl, triazolyl, oxadiazolyl and thiadiazolyl.

"Thiazolyl" as used herein includes 2-thiazolyl, 4-thiazolyl and 5-thiazolyl. "Isothiazolyl" as used herein includes 3-isothiazolyl, 4-isothiazolyl, and 5-isothiazolyl. "Oxazolyl" as used herein includes 2-oxazolyl, 4-oxazolyl and 5-oxazolyl. "Isoxazolyl" as used herein includes 3-isoxazolyl, 4-isoxazolyl, and 5-isoxazolyl. "Thiophenyl" as used herein includes 2-thiophenyl and 3-thiophenyl. "Furanyl" as used herein includes 2-furanyl and 3-furanyl. "Pyrrolyl" as used herein includes 2-pyrrolyl and 3-pyrrolyl. "Imidazolyl" as used herein includes 2-imidazolyl and 4-imidazolyl. "Triazolyl" as used herein includes 1-triazolyl, 4-triazolyl and 5-triazolyl. "Oxadiazolyl" as used herein includes 4- and 5-(1,2,3-oxadiazolyl), 3- and 5-(1,2,4-oxadiazolyl), 3-(1,2,5-oxadiazolyl), 2-(1,3,4-oxadiazolyl). "Thiadiazolyl" as used herein includes 4- and 5-(1,2,3-thiadiazolyl), 3- and 5-(1,2,4-thiadiazolyl), 3-(1,2,5-thiadiazolyl), 2-1,3,4-thiadiazolyl).

In the present specification the term "6-membered heteroaryl ring" means a 6-membered aromatic ring including one or more heteroatoms each independently selected from N, O and S. Preferably there are not more than three heteroatoms in total in the ring. More preferably there are not more than two heteroatoms in total in the ring. More preferably there is not more than one heteroatom in total in the ring. The term includes, for example, the groups pyridyl, pyrimidyl, pyrazinyl, pyridazinyl and triazinyl.

"Pyridyl" as used herein includes 2-pyridyl, 3-pyridyl and 4-pyridyl. "Pyrimidyl" as used herein includes 2-pyrimidyl, 4-pyrimidyl and 5-pyrimidyl. "Pyrazinyl" as used herein includes 2-pyrazinyl and 3-pyrazinyl. "Pyridazinyl" as used herein includes 3-pyridazinyl and 4-pyridazinyl. "Triazinyl" as used herein includes 2-(1,3,5-triazinyl), 3-, 5- and 6-(1,2,4-triazinyl) and 4- and 5-(1,2,3-triazinyl).

In the present specification the term "ortho" refers to a position on the Ar1 aromatic ring which is adjacent to the position from which Ar1 links to the rest of the compound of formula (I).

In the present specification the term "N-protecting group" means a functional group which renders the N atom to which it is attached unreactive under the reaction conditions to which the N-protected compound is subsequently exposed, except where said protected N atom is also bonded to an H atom and except where such conditions are specifically chosen to remove the N-protecting group. The choice of N-protecting group will depend upon the subsequent reaction conditions and suitable N-protecting groups for given situations will be known to the person skilled in the art. Further information on suitable N-protecting groups, including methods for their addition and removal, is contained in the well known text "Protective Groups in Organic Synthesis", Theodora W. Greene and Peter G. M. Wuts, John Wiley & Sons, Inc., New York, 1999, pp. 494-653. Examples of N-protecting groups include carbamate protecting groups —CO—OR$_A$ wherein R$_A$ is, for example, methyl, ethyl, 9-fluorenylmethyl (Fmoc), 2,2,2-trichloroethyl (Troc), 2-trimethylsilylethyl (Teoc), t-butyl (Boc), allyl (Alloc), benzyl (Cbz) or p-methoxybenzyl (Moz); amide protecting groups —CO—R$_B$ wherein R$_B$ is, for example, H, methyl, benzyl or phenyl; alkylamine protecting groups —R$_C$ wherein R$_C$ is, for example, methyl, t-butyl, allyl, [2-(trimethylsilyl))ethoxy]methyl, benzyl, 4-methoxybenzyl, 2,4-dimethoxybenzyl, diphenylmethyl or triphenylmethyl (trityl); and sulfonamide protecting groups —SO$_2$—R$_D$ wherein R$_D$ is, for example, methyl, benzyl, phenyl or phenyl substituted with from 1 to 5 substituents each independently selected from methyl, t-butyl, methoxy and nitro. In some instances, the reaction conditions employed mean that N-protecting groups which are stable under strongly basic conditions and/or in the presence of strong nucleophiles (such as organometallic reagents) are generally preferred. Examples of such preferred N-protecting groups include alkylamine protecting groups —R$_C$ wherein R$_C$ is, for example, methyl, t-butyl, allyl, [2-(trimethylsilyl)) ethoxy]methyl, benzyl, 4-methoxybenzyl, 2,4-dimethoxybenzyl, diphenylmethyl or triphenylmethyl (trityl). Benzyl is an especially preferred N-protecting group.

In a preferred embodiment of the present invention, X is OH, C1-C4 alkoxy, or $NH_2$. More preferably, X is OH or $NH_2$. Most preferably X is OH.

In a preferred embodiment of the present invention, Rx is H or methyl. Most preferably Rx is H.

In a preferred embodiment of the present invention, Ry is H or methyl. Most preferably Ry is H.

In a preferred embodiment of the present invention, each Rz group is independently H or methyl, with the proviso that not more than 3 Rz groups may be methyl. Most preferably, each Rz is H.

In a preferred embodiment of the present invention, R1 is C1-C6 alkyl (optionally substituted with 1, 2 or 3 halogen atoms and/or with 1 substituent selected from C1-C4 alkylthio (optionally substituted with 1, 2 or 3 fluorine atoms), C1-C4 alkoxy (optionally substituted with 1, 2 or 3 fluorine atoms), C3-C6 cycloalkoxy, C1-C4 alkylsulfonyl, cyano, —CO—O(C1-C2 alkyl), —O—CO—(C1-C2 alkyl) and hydroxy). More preferably, R1 is C1-C6 alkyl (optionally substituted with 1, 2 or 3 halogen atoms and/or with 1 substituent selected from C1-C4 alkoxy (optionally substituted with 1, 2 or 3 fluorine atoms), cyano and hydroxy). More preferably, R1 is C1-C6 alkyl (optionally substituted with 1, 2 or 3 halogen atoms). More preferably, R1 is C1-C6 alkyl (optionally substituted with 1, 2 or 3 fluorine atoms). Examples of specific identities for R1 within this embodiment include methyl, ethyl, iso-propyl, iso-butyl, n-butyl, 3,3,3-trifluoropropyl and 4,4,4-trifluorobutyl.

In a preferred embodiment of the present invention, R1 is C2-C6 alkenyl (optionally substituted with 1, 2 or 3 halogen atoms).

In a preferred embodiment of the present invention, R1 is C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C, S—C or C=C bond. More preferably, R1 is C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C bond. More preferably, R1 is C3-C6 cycloalkyl wherein one C—C bond within the cycloalkyl moiety is optionally substituted by an O—C bond. Examples of specific identities for R1 within this embodiment include cyclopropyl, cyclopentyl and tetrahydropyranyl (in particular tetrahydro-2H-pyran-4-yl).

In a preferred embodiment of the present invention, R1 is C3-C6 cycloalkyl (optionally substituted with 1, 2 or 3 halogen atoms and/or with 1 substituent selected from C1-C4 alkoxy and hydroxy). More preferably, R1 is C3-C6 cycloalkyl. Examples of specific identities for R1 within this embodiment include cyclopropyl and cyclopentyl.

In a preferred embodiment of the present invention, R1 is C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is substituted by an O—C, S—C or C=C bond. More preferably, R1 is C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is substituted by an O—C bond. More preferably, R1 is C3-C6 cycloalkyl wherein one C—C bond within the cycloalkyl moiety is substituted by an O—C bond. An example of a specific identity for R1 within this embodiment is tetrahydropyranyl (in particular tetrahydro-2H-pyran-4-yl).

In a preferred embodiment of the present invention, R1 is C4-C7 cycloalkylalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C, S—C or C=C bond.

In a preferred embodiment of the present invention, R1 is C4-C7 cycloalkylalkyl (optionally substituted with 1, 2 or 3 halogen atoms and/or with 1 substituent selected from C1-C4 alkoxy and hydroxy).

In a preferred embodiment of the present invention, R1 is C4-C7 cycloalkylalkyl (optionally substituted with 1, 2 or 3 halogen atoms and/or with 1 substituent selected from C1-C4 alkoxy and hydroxy) wherein one C—C bond within the cycloalkyl moiety is substituted by an O—C, S—C or C=C bond.

In a preferred embodiment of the present invention, R1 is $CH_2Ar2$ wherein Ar2 is as defined above. More preferably, R1 is $CH_2Ar2$ wherein Ar2 is a phenyl ring or a pyridyl (preferably 2-pyridyl) ring each of which may be substituted with 1, 2 or 3 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo and hydroxy. More preferably, R1 is $CH_2Ar2$ wherein Ar2 is a phenyl ring optionally substituted in the manner described in the preceding sentence. More preferably, R1 is $CH_2Ar2$ wherein Ar2 is a phenyl ring optionally substituted with 1 or 2 substituents each independently selected from C1-C4 alkyl (optionally substituted with 1, 2 or 3 halogen atoms), C1-C4 alkoxy (optionally substituted with 1, 2 or 3 halogen atoms), halo and hydroxy. Examples of specific identities for R1 within this embodiment include phenylmethyl and (2-methoxy-phenyl)methyl.

In a preferred embodiment of the present invention, Ar1 is a phenyl ring or a 5- or 6-membered heteroaryl ring; each of which is substituted in the ortho position with a substituent selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), —CO—O(C1-C4 alkyl), cyano, —NRR, —CONRR, halo, hydroxy, pyridyl, thiophenyl, phenyl, benzyl and phenoxy, each of which ortho substituents is optionally ring-substituted (where a ring is present) with 1, 2 or 3 substituents each independently selected from halogen, C1-C4 alkyl (optionally substituted with 1, 2 or 3 halogen atoms), C1-C4 alkoxy (optionally substituted with 1, 2 or 3 halogen atoms), carboxy, nitro, hydroxy, cyano, —NRR, —CONRR, $SO_2NRR$ and $SO_2R$; and each of which is (in addition to ortho substitution) optionally further substituted with 1 or 2 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), —CO—O(C1-C4 alkyl), cyano, —NRR, —CONRR, halo and hydroxy. More preferably, Ar1 is a phenyl ring or a pyridyl (preferably 2-pyridyl) ring each of which is substituted and optionally further substituted in the manner described in the preceding sentence. More preferably, Ar1 is a group of the formula (a):

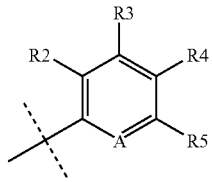

(a)

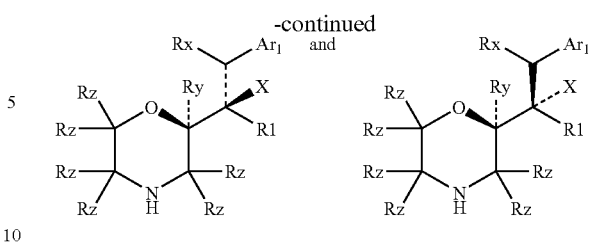

wherein,

A is N or CR6 (preferably CR6); R2 is C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo, hydroxy, pyridyl, thiophenyl, phenyl (optionally substituted with 1, 2 or 3 substituents each independently selected from halogen, C1-C4 alkyl (optionally substituted with 1, 2 or 3 halogen atoms), or C1-C4 alkoxy (optionally substituted with 1, 2 or 3 halogen atoms)) or phenoxy (optionally substituted with 1, 2 or 3 halogen atoms); R3 is H; R4 is H; R5 is H, C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo or hydroxy; and R6 (if present) is H or halo (preferably H). More preferably, Ar1 is a group of the formula (a) wherein, A is CR6; R2 is C1-C4 alkyl (optionally substituted with 1, 2 or 3 fluorine atoms), C1-C4 alkoxy (optionally substituted with 1, 2 or 3 fluorine atoms), halo or phenyl (optionally substituted with 1, 2 or 3 fluorine atoms); R3 is H; R4 is H; R5 is H or F; and R6 is H or halo. More preferably, Ar1 is a group of the formula (a) wherein, A is CR6; R2 is C1-C4 alkyl (optionally substituted with 1, 2 or 3 fluorine atoms), C1-C4 alkoxy (optionally substituted with 1, 2 or 3 fluorine atoms) or phenyl (optionally substituted with 1, 2 or 3 fluorine atoms); R3 is H; R4 is H; R5 is H or F; and R6 is H. Examples of specific identities for Ar1 include 2-methoxy-phenyl, 2-ethoxy-phenyl, 2-trifluoromethoxy-phenyl, 2-phenyl-phenyl, 2-(3-fluoro-phenyl)-phenyl, 2-chloro-phenyl, 2-methoxy-5-fluoro-phenyl, 2-chloro-6-fluoro-phenyl and 2-phenyl-5-fluoro-phenyl.

It will be appreciated that a compound of formula (I) above will possess at least two asymmetric carbon atoms. In the present specification, where a structural formula does not specify the stereochemistry at one or more chiral centres, it encompasses all possible stereoisomers and all possible mixtures of stereoisomers (including, but not limited to, racemic mixtures), which may result from stereoisomerism at each of the one or more chiral centers.

Thus, compounds defined by formula (I) above include each of the individual stereoisomers

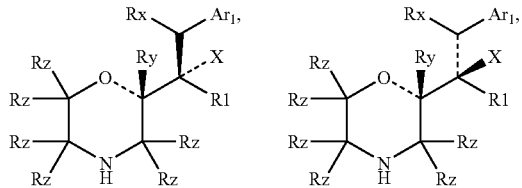

-continued

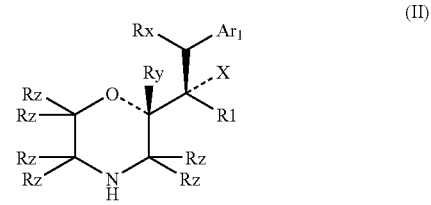

and all possible mixtures thereof. While all stereoisomers and mixtures thereof, are contemplated by the present invention, preferred embodiments include enantiomerically and diastereomerically pure compounds of formula I. As used herein the term "enantiomerically pure" refers to an enantiomeric excess which is greater than 90%, preferably greater than 95%, more preferably greater than 99%. As used herein the term "diastereomerically pure" refers to a diastereomeric excess which is greater than 90%, preferably greater than 95%, more preferably greater than 99%.

In a preferred embodiment of the present invention, there is provided a compound of formula (II)

(II)

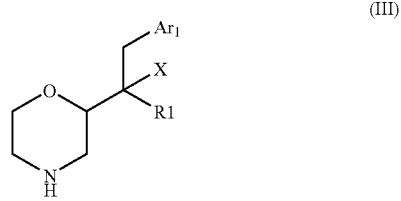

wherein, X, Rx, Ry, Rz, R1 and Ar1 are as defined for formula (I) above; or a pharmaceutically acceptable salt thereof. Preferably said compound of formula (II) is both enantiomerically pure and diastereomerically pure.

In a preferred embodiment of the present invention, there is provided a compound of formula (III)

(III)

wherein, X, R1 and Ar1 are as defined for formula (I) above; or a pharmaceutically acceptable salt thereof.

In a preferred embodiment of the present invention, there is provided a compound of formula (III) wherein X is OH or $NH_2$;

R1 is C1-C6 alkyl (optionally substituted with 1, 2 or 3 halogen atoms and/or with 1 substituent selected from C1-C4 alkylthio (optionally substituted with 1, 2 or 3 fluorine atoms), C1-C4 alkoxy (optionally substituted with 1, 2 or 3 fluorine atoms), C3-C6 cycloalkoxy, C1-C4 alkylsulfonyl, cyano, —CO—O(C1-C2 alkyl), —O—CO—(C1-C2 alkyl) and hydroxy); C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C, S—C or C═C bond; or CH₂Ar2 wherein Ar2 is a phenyl ring or a pyridyl (preferably 2-pyridyl) ring each of which may be substituted with 1, 2 or 3 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo and hydroxy; and Ar1 is a phenyl ring or a 5- or 6-membered heteroaryl ring; each of which is substituted in the ortho position with a substituent selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), —CO—O(C1-C4 alkyl), cyano, —NRR, —CONRR, halo, hydroxy, pyridyl, thiophenyl, phenyl, benzyl and phenoxy, each of which ortho substituents is optionally ring-substituted (where a ring is present) with 1, 2 or 3 substituents each independently selected from halogen, C1-C4 alkyl (optionally substituted with 1, 2 or 3 halogen atoms), C1-C4 alkoxy (optionally substituted with 1, 2 or 3 halogen atoms), carboxy, nitro, hydroxy, cyano, —NRR, —CONRR, SO₂NRR and SO₂R; and each of which is (in addition to ortho substitution) optionally further substituted with 1 or 2 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), —CO—O(C1-C4 alkyl), cyano, —NRR, —CONRR, halo and hydroxy, or a pharmaceutically acceptable salt thereof.

In a preferred embodiment of the present invention, there is provided a compound of formula (IV)

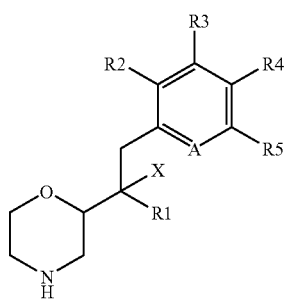

(IV)

wherein,

X is OH or NH₂;

R1 is C1-C6 alkyl (optionally substituted with 1, 2 or 3 halogen atoms and/or with 1 substituent selected from C1-C4 alkoxy (optionally substituted with 1, 2 or 3 fluorine atoms), cyano, and hydroxy); C3-C6 cycloalkyl (optionally substituted with 1, 2 or 3 halogen atoms and/or with 1 substituent selected from C1-C4 alkoxy and hydroxy) wherein one C—C bond within the cycloalkyl moiety is optionally substituted by an O—C bond; or CH₂Ar2 wherein Ar2 is a phenyl ring optionally substituted with 1, 2 or 3 substituents each independently selected from C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo and hydroxy, A is N or CR6 preferably CR6; R2 is C1-C4 alkyl (optionally substituted with 1, 2 or 3 halogen atoms), C1-C4 alkoxy (optionally substituted with 1, 2 or 3 halogen atoms), C₁-C4 alkylthio (optionally substituted with 1, 2 or 3 halogen atoms), halo, hydroxy, pyridyl, thiophenyl, phenyl (optionally substituted with 1, 2 or 3 substituents each independently selected from halogen, C1-C4 alkyl (optionally substituted with 1, 2 or 3 halogen atoms), or C1-C4 alkoxy (optionally substituted with 1, 2 or 3 halogen atoms)) or phenoxy (optionally substituted with 1, 2 or 3 halogen atoms); R3 is H; R4 is H; R5 is H, C1-C4 alkyl (optionally substituted with 1, 2 or 3 halogen atoms), C1-C4 alkoxy (optionally substituted with 1, 2 or 3 halogen atoms), C1-C4 alkylthio (optionally substituted with 1, 2 or 3 halogen atoms), halo or hydroxy; and R6 (if present) is H; or a pharmaceutically acceptable salt thereof.

In a preferred embodiment of the present invention, there is provided a compound of formula (V)

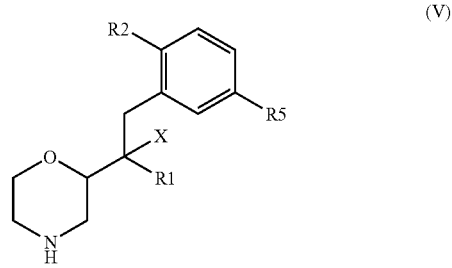

(V)

wherein,

X is OH or NH₂;

R1 is C1-C6 alkyl (optionally substituted with 1, 2 or 3 fluorine atoms), C3-C6 cycloalkyl wherein one C—C bond within the cycloalkyl moiety is optionally substituted by an O—C bond or CH₂Ar2 wherein Ar2 is a phenyl ring optionally substituted with 1 or 2 substituents each independently selected from C1-C4 alkyl (optionally substituted with 1, 2 or 3 halogen atoms), C1-C4 alkoxy (optionally substituted with 1, 2 or 3 halogen atoms), halo and hydroxy;

R2 is C1-C4 alkyl (optionally substituted with 1, 2 or 3 fluorine atoms), C1-C4 alkoxy (optionally substituted with 1, 2 or 3 fluorine atoms) or phenyl (optionally substituted with 1, 2 or 3 fluorine atoms); and R5 is H or F; or a pharmaceutically acceptable salt thereof.

In a preferred embodiment of the present invention, there is provided a compound of formula (VI)

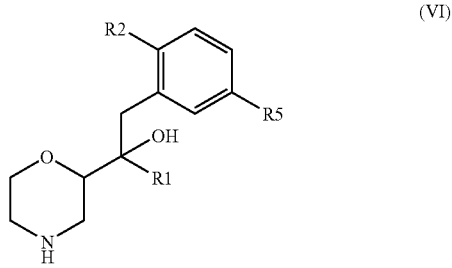

(VI)

wherein,

R1 is C1-C6 alkyl (optionally substituted with 1, 2 or 3 fluorine atoms) or C3-C6 cycloalkyl wherein one C—C bond within the cycloalkyl moiety is optionally substituted by an O—C bond;

R2 is C1-C4 alkyl (optionally substituted with 1, 2 or 3 fluorine atoms), C1-C4 alkoxy (optionally substituted with 1, 2 or 3 fluorine atoms) or phenyl (optionally substituted with 1, 2 or 3 fluorine atoms); and R5 is H or F; or a pharmaceutically acceptable salt thereof.

Specific embodiments of the present invention include the compounds
1-[1,1'-biphenyl]-2-yl-2-morpholin-2-ylpropan-2-ol,
1-[5-fluoro-2-(methyloxy)phenyl]-2-morpholin-2-ylbutan-2-ol,
2-morpholin-2-yl-1-{2-[(trifluoromethyl)oxy]phenyl}butan-2-ol,
1-[1,1'-biphenyl]-2-yl-2-morpholin-2-ylbutan-2-ol,
1-[5-fluoro-2-(methyloxy)phenyl]-3-methyl-2-morpholin-2-ylbutan-2-ol,
3-methyl-1-[(2-methyloxy)phenyl]-2-morpholin-2-ylbutan-2-ol,
1-[(2-ethyloxy)phenyl]-3-methyl-2-morpholin-2-ylbutan-2-ol,
3-methyl-2-morpholin-2-yl-1-{2-[(trifluoromethyl)oxy]butan-2-ol,
1-[1,1'-biphenyl]-2-yl-3-methyl-2-morpholin-2-ylbutan-2-ol,
1-(4-fluoro[1,1'-biphenyl]-2-yl)-3-methyl-2-morpholin-2-ylbutan-2-ol,
1-[5-fluoro-2-(methyloxy)phenyl]-4-methyl-2-morpholin-2-yl-pentan-2-ol,
1-[2-(ethyloxy)phenyl]-4-methyl-2-morpholin-2-ylpentan-2-ol,
4-methyl-2-morpholin-2-yl-1-{2[trifluoromethyl)oxy]phenyl}pentan-2-ol,
1-[1,1'-biphenyl]-2-yl-4-methyl-2-morpholin-2-ylpentan-2-ol,
1-(4-fluoro[1,1'-biphenyl]-2-yl)-4-methyl-2-morpholin-2-ylpentan-2-ol,
1-cyclopentyl-2-[5-fluoro-2-(methyloxy)phenyl]-1-morpholin-2-ylethanol,
1-cyclopentyl-2-[2-(ethyloxy)phenyl]-1-morpholin-2-ylethanol,
1-cyclopentyl-1-morpholin-2-yl-2-{2-[(trifluoromethyl)oxy]phenyl}ethanol,
2-[1,1'-biphenyl]-2-yl-1-cyclopentyl-1-morpholin-2-ylethanol,
1-cyclopentyl-2-(4-fluoro[1,1'-biphenyl]-2-yl)-1-morpholin-2-ylethanol,
2-[5-fluoro-2-(methyloxy)phenyl]-1-morpholin-2-yl-1-tetrahydro-2H-pyran-4-ylethanol,
1-morpholin-2-yl-1-tetrahydro-2H-pyran-4-yl-2-{2-[(trifluoromethyl)oxy]phenyl}ethanol,
2-[1,1'-biphenyl]-2-yl-1-morpholin-2-yl-1-tetrahydro-2H-pyran-4-ylethanol,
2-(3'-fluoro-biphenyl-2-yl)-1-morpholin-2-yl-1-(tetrahydro-pyran-4-yl)-ethanol,
5,5,5-trifluoro-1-(5-fluoro-2-methoxy-phenyl)-2-morpholin-2-yl-pentan-2-ol,
5,5,5-trifluoro-2-morpholin-2-yl-1-(2-trifluoromethoxy-phenyl)-pentan-2-ol,
1-[1,1'-biphenyl]-2-yl-5,5,5-trifluoro-2-morpholin-2-ylpentan-2-ol,
6,6,6-trifluoro-1-[5-fluoro-2-(methyloxy)phenyl]-2-morpholin-2-ylhexan-2-ol,
1-[1,1'-biphenyl]-2-yl-6,6,6-trifluoro-2-morpholin-2-yl]hexan-2-ol,
1-cyclopropyl-2-[-2-(methyloxy)phenyl]-1-morpholin-2-ylethanol,
1-cyclopropyl-2-[-2-(ethyloxy)phenyl]-1-morpholin-2-ylethanol,
2-[1,1'-biphenyl]-2-yl-1-cyclopropyl-1-morpholin-2-ylethanol,
1,3-bis-(2-methoxy-phenyl)-2-morpholin-2-yl-propan-2-ol,
1-(2-methoxy-benzyl)-2-(2-methoxy-phenyl)-1-morpholin-2-yl-ethylamine,
2-morpholin-2-yl-1,3-diphenyl-propan-2-ol,
1-(2-methoxy-phenyl)-2-morpholin-2-yl-hexan-2-ol,
2-morpholinyl-1-biphenyl-2-yl-hexan-2-ol,
1-(2-chloro-6-fluoro-phenyl)-4-methyl-2-morpholin-2-yl-pentan-2-ol and
1-(2-chloro-phenyl)-4-methyl-2-morpholin-2-yl-pentan-2-ol and pharmaceutically acceptable salts thereof.

The compounds of the present invention are inhibitors of norepinephrine reuptake. Biogenic amine transporters control the amount of biogenic amine neurotransmitters in the synaptic cleft. Inhibition of the respective transporter leads to a rise in the concentration of that neurotransmitter within the synaptic cleft. Compounds of formula (I) and their pharmaceutically acceptable salts preferably exhibit a $K_i$ value less than 600 nM at the norepinephrine transporter as determined using the scintillation proximity assay described below. More preferred compounds of formula (I) and their pharmaceutically acceptable salts exhibit a $K_i$ value less than 100 nM at the norepinephrine transporter. Still more preferred compounds of formula (I) and their pharmaceutically acceptable salts exhibit a $K_i$ value less than 50 nM at the norepinephrine transporter. Especially preferred compounds of formula (I) and their pharmaceutically acceptable salts exhibit a $K_i$ value less than 20 nM at the norepinephrine transporter. Preferably, compounds of the present invention selectively inhibit the norepinephrine transporter relative to the serotonin and dopamine transporters by a factor of at least five, more preferably by a factor of at least ten using the scintillation proximity assays described below.

In addition, the compounds of the present invention are preferably acid stable. Advantageously, they have a reduced interaction (both as substrate and inhibitor) with the liver enzyme Cytochrome P450 (CYP2D6). That is to say, they preferably exhibit less than 75% metabolism via the CYP2D6 pathway according to the CYP2D6 substrate assay described below and they preferably exhibit an IC50 of >6 μM according to the CYP2D6 inhibitor assay described below.

In view of their pharmacological activity, the compounds of the present invention are indicated for the treatment of disorders of the central and/or peripheral nervous system, in particular, disorders associated with norepinephrine dysfunction in mammals, especially humans, including children, adolescents and adults.

The term "norepinephrine dysfunction" as used herein refers to a reduction in the amount of norepinephrine neurotransmitter within the synaptic cleft below that which would be considered to be normal or desirable for a species, or an individual within that species. Thus the phrase "disorders associated with norepinephrine dysfunction in mammals" refers to disorders which are associated with a reduction in the amount of norepinephrine neurotransmitter within the synaptic cleft below that which would be considered to be normal or desirable for the mammalian species, or an individual within the species, in question. Disorders associated with norepinephrine dysfunction in mammals include, for example, nervous system conditions selected from the group consisting of an addictive disorder and withdrawal syndrome, an adjustment disorder (including depressed mood, anxiety, mixed anxiety and depressed mood, disturbance of conduct, and mixed disturbance of conduct and mood), an age-associated learning and mental disorder (including Alzheimer's disease), alcohol addiction, allergies (in particular allergic rhinitis), anorexia nervosa, apathy, asthma, an attention-deficit disorder (ADD) due to general medical conditions, attention-deficit hyperactivity disorder (ADHD) including the predominantly inattentive type of ADHD and the predominantly hyperactive-impulsive type of ADHD (and optionally by way of combination therapy with one or more stimulants such as methylphenidate, amphetamine and dextroamphetamine), bipolar disorder, bulimia nervosa, chronic fatigue syndrome, chronic or acute stress, cognitive disorders (discussed in more detail below but including delusions, dementias, amnestic disorders, mild cognitive impairment (MCI), cognitive impairment associated with schizophrenia (CIAS) and cognitive disorders not otherwise specified), communication disorders (including stuttering, expressive language disorder, mixed receptive-expressive language disorder, phonological disorder and communication disorder not otherwise specified), conduct disorder, cyclothymic disorder, dementia of the Alzheimers type (DAT), depression (including adolescent depression and minor depression), dysthymic disorder, emotional dysregulation (including emotional dysregulation associated with ADHD, borderline personality disorder, bipolar disorder, schizophrenia, schizoaffective disorder and intermittent explosive disorder), fibromyalgia and other somatoform disorders (including somatization disorder, conversion disorder, pain disorder, hypochondriasis, body dysmorphic disorder, undifferentiated somatoform disorder, and somatoform disorder NOS), generalized anxiety disorder, hot flashes or vasomotor symptoms, hypotensive states including orthostatic hypotension, impulse control disorders (including intermittent explosive disorder, kleptomania, pyromania, pathological gambling, trichotillomania and impulse-control disorder not otherwise specified), incontinence (i.e. bedwetting, stress incontinence, genuine stress incontinence, and mixed incontinence), an inhalation disorder, an intoxication disorder, learning disabilities (including developmental speech and language disorders (such as developmental articulation disorder, developmental expressive language disorder and developmental receptive language disorder), learning disorders (such as reading disorder, mathematics disorder, disorder of written expression and learning disorder not otherwise specified) and motor skills disorders (such as developmental coordination disorder)), mania, migraine headaches, neuropathic pain, nicotine addiction, obesity (i.e., reducing the weight of obese or overweight patients), obsessive compulsive disorders and related spectrum disorders, oppositional defiant disorder, pain including chronic pain, neuropathic pain and antinociceptive pain, panic disorder, Parkinson's disease (in particular to improve dyskinesia, oscilations, balance, coordination, depression, and motivation), peripheral neuropathy, personality change due to a general medical condition (including labile type, disinhibited type, aggressive type, apathetic type, paranoid type, combined type and unspecified type), pervasive developmental disorders (including autistic disorder, Asperger's disorder, Rett's disorder, childhood disintegrative disorder, and pervasive developmental disorder not otherwise specified), post-traumatic stress disorder, premenstrual dysphoric disorder (i.e., premenstrual syndrome and late luteal phase dysphoric disorder), psoriasis, psychoactive substance use disorders, a psychotic disorder (including schizophrenia, schizoaffective and schizophreniform disorders), seasonal affective disorder, a sleep disorder (such as narcolepsy and enuresis), social phobia (including social anxiety disorder), a specific developmental disorder, selective serotonin reuptake inhibition (SSRI) "poop out" syndrome (i.e., wherein a patient who fails to maintain a satisfactory response to SSRI therapy after an initial period of satisfactory response), TIC disorders (e.g., Tourette's Disease), tobacco addiction and vascular dementia. The compounds of the present invention are particularly suitable for the treatment of attention deficit hyperactivity disorder, ADHD. The compounds of the present invention are also particularly suitable for the treatment of schizophrenia.

The term "cognitive disorders" (also variously referred to as "cognitive failure," "cognitive insufficiency," "cognitive deficit," "cognitive impairment," "cognitive dysfunction," and the like) refers to the dysfunction, diminution, or loss of one or more cognitive functions, the processes by which knowledge is acquired, retained, and used. Cognitive dysfunction includes cognitive changes associated with aging ("age-associated memory impairment"), as well as changes due to other causes. Cognitive impairment is most commonly due to a delirium or dementia, but can also occur in association with a number of other medical or neuropsychiatric disorders. More focal cognitive deficits are diagnosed using the criteria disclosed in the *Diagnostic and Statistical Manual of Mental Disorders*, Fourth Edition, Text Revision (DSM-IV-TR™, 2000), American Psychiatric Association, Washington, D.C., as either amnestic disorders (affecting memory) or cognitive disorder not otherwise specified (NOS), which includes executive dysfunction, visuospatial/visuocontructional impairment, attentional deficits, disorientation, etc. These more focal cognitive disorders also have a wide variety of causes, some of which are of unknown etiology.

A delirium is characterized by a disturbance of consciousness with a reduced ability to focus, sustain, or shift attention and a change in cognition that develops over a short period of time. Delirium is very common, and occurs on average in about a fifth of general hospital inpatients, and is even more common in nursing home patients and those with terminal illnesses. The disorders included in the "Delirium" section of the DSM-IV-TR™ are listed according to presumed etiology: Delirium Due to a General Medical Condition, Substance-Induced Delirium (i.e., due to a drug of abuse, a medication, or toxin exposure), Delirium Due to Multiple Etiologies, or Delirium Not Otherwise Specified (if the etiology is indeterminate). As disclosed by Wise et al. ((2002) Delirium (Confusional States), In Wise and Rundell, Eds., *The American Psychiatric Publishing Textbook of Consultation-Liaison Psychiatry, Psychiatry in the Medically Ill*, Second Edition, American Psychiatric Publishing, Inc., Washington, D.C., Chapter 15, pp. 257-272, Table 15-4), exemplary etiological bases of delirium include, but are not limited to, infection, withdrawal from alcohol and drugs, acute metabolic conditions, trauma of various types, CNS pathologies, hypoxia, vitamin deficiencies, endocrinopathies, acute vascular conditions, toxins or drugs, and heavy metals.

A dementia is a chronic condition, usually with a more gradual deterioration of memory and other intellectual functioning and other cognitive skills severe enough to interfere with the ability to perform activities of daily living. Although dementia may occur at any age, it primarily affects the elderly, presenting in more than 15% of persons over 65 years of age and in as many as 40% of persons over 80 years old. Dementia due to Alzheimer's disease is particularly common. Non-Alzheimer's cognitive impairments and/or dementias include, for example, those caused by or associated with: vascular diseases; Parkinson's disease; Lewy body disease (diffuse Lewy body disease); HIV/AIDS; mild cognitive impairments; mild neurocognitive disorders; age-associated memory impairments; neurologic and/or psychiatric conditions including epilepsy and epilepsy treatments; brain tumors, cysts, lesions, or other inflammatory brain diseases; multiple sclerosis; Down's syndrome; Rett's syndrome; progressive supranuclear palsy; frontal lobe dementia syndromes; schizophrenia and related psychiatric disorders; antipsychotic medications; traumatic brain injury (closed head injury), dementia pugilistica, and other head traumas; normal-pressure hydrocephalus; surgery (including coronary artery by-pass graft surgery) and anaesthesia, electroconvulsive shock therapy, and cancer and cancer therapies.

The dementias are also listed in the "Dementia" section of the DSM-IV-TR™ according to presumed etiology: Dementia of the Alzheimer's Type, Vascular Dementia, Dementia Due to Other General Medical Conditions (e.g., human immunodeficiency virus [HIV] disease, head trauma, Parkinson's disease, Huntington's disease), Substance-Induced Persisting Dementia (i.e., due to a drag of abuse, a medication, or toxin exposure), Dementia Due to Multiple Etiologies, or Dementia Not Otherwise Specified (if the etiology is indeterminate). As disclosed by Gray and Cummings ((2002) Dementia, In Wise and Rundell, Eds., *The American Psychiatric Publishing Textbook of Consultation-Liaison Psychiatry, Psychiatry in the Medically Ill*, Second Edition, American Psychiatric Publishing, Inc., Washington, D.C., Chapter 16, pp. 273-306, Table 16-1), exemplary etiological bases of principal dementia syndromes include, but are not limited to, degenerative disorders (cortical and subcortical), vascular disorders, myelinoclastic disorders, traumatic conditions, neoplastic disorders, hydrocephalic disorders, inflammatory conditions, infections, toxic conditions, metabolic disorders, and psychiatric disorders.

An amnestic disorder is characterized by memory impairment in the absence of other significant accompanying cognitive impairments. The disorders in the "Amnestic Disorders" section of the DSM-IV-TR™ are also listed according to presumed etiology: Amnestic Disorder Due to a General Medical Condition, Substance-Induced Persisting Amnestic Disorder, or Amnestic Disorder Not Otherwise Specified.

Cognitive Disorder Not Otherwise Specified in the DSM-IV-TR™ covers presentations that are characterized by cognitive dysfunction presumed to be due to either a general medical condition or substance use that do not meet criteria for any of the disorders listed elsewhere in the section of the DSM-IV-TR™ entitled "Delirium, Dementia, and Amnestic and Other Cognitive Disorders."

Dementia, amnestic disorders, and cognitive disorders NOS occur in patients with a wide variety of other disorders including, but not limited to, Huntington's disease (chorea); Pick's disease; spinocerebellar ataxias (types 1-11); corticobasalganglionic degeneration; neuroacanthocytosis; dentatorubropallidoluysian atropy (DRPLA); systemic lupus erythematosus; heavy metal intoxication; alcoholic dementia (Wernicke's encephalopathy); fetal alcohol syndrome; single or multiples strokes, including small vessels (Binswanger's dementia: subcortical arteriosclerotic encephalopathy) and large vessels (multi-infarct dementia); anoxic encephalopathy, tumors; birth anoxia; premature birth; inborn errors of metabolism; neurofibromatosis (Type I); tuberous sclerosis; Hallervorden Spatz disease; Wilson's disease; post-infectious sequelae (e.g., tuberculosis, viral encephalitis, bacterial meningitis); subdural hematoma; subcortical dementia; Creutzfeldt-Jakob disease; Gerstmann-Sträussler-Scheinker disease; general paresis; and syphilis.

As discussed in detail above, cognitive failure may present in patients suffering from a number of disorders, including dementia or delirium, or due to a wide variety of other causes. The compounds of the present invention are useful for the treatment or prevention of cognitive failure associated with, or due to, the disorders or etiologies discussed above, including disorders formally classified in the DSM-IV-TR™. For the convenience of the reader, the DSM-IV-TR™ code numbers or descriptions are supplied below. "ICD-9-CM codes" refers to codes for, e.g., selected general medical conditions and medication-induced disorders contained in the *International Classification of Diseases, 9th Revision, Clinical Modification*.

| | |
|---|---|
| Delirium Due to a General Medical Condition | 293.0 |

Substance-Induced Delirium, including:
    Substance Intoxication Delirium:
    Code [Specific Substance] Intoxication Delirium:
    (291.0 Alcohol; 292.81 Amphetamine [or Amphetamine-Like Substance]; 292.81 Cannabis; 292.81 Cocaine; 292.81 Hallucinogen; 292.81 Inhalant; 292.81 Opioid; 292.81 Phencyclidine [or Phencyclidine-Like Substance]; 292.81 Sedative, Hypnotic, or Anxiolytic; 292.81 Other [or Unknown] Substance [e.g., cimetidine, digitalis, benztropine])
    Substance Withdrawal Delirium:
    Code [Specific Substance] Withdrawal Delirium:
    (291.0 Alcohol; 292.81 Sedative, Hypnotic, or Anxiolytic; 292.81 Other [or Unknown] Substance)

Delirium Due to Multiple Etiologies:
    Multiple codes are used, reflecting the specific delirium and specific etiologies, e.g., 293.0 Delirium Due to Viral Encephalitis; 291.0 Alcohol Withdrawal Delirium

| | |
|---|---|
| Delirium Not Otherwise Specified | 780.09 |
| Dementia of the Alzheimer's Type | 294.1x* (*ICD-9-CM code) |
| Subtypes: | |
| With Early Onset (onset of the dementia is age 65 years or under) | |
| With Late Onset (onset of the dementia is after age 65 years) | |
| Without Behavioral Disturbance | 294.10 |
| With Behavorial Disturbance | 294.11 |
| Vascular Dementia | 290.4x |
| Subtypes: | |
| With Delirium | 290.41 |
| With Delusions | 290.42 |
| With Depressed Mood | 290.43 |
| With Behavioral Disturbance | Uncoded |
| Uncomplicated | 290.40 |
| Dementia Due to HIV Disease | 294.1x* (*ICD-9-CM code) |
| Dementia Due to Head Trauma | 294.1x* (*ICD-9-CM code) |
| Dementia Due to Parkinson's Disease | 294.1x* (*ICD-9-CM code) |
| Dementia Due to Huntington's Disease | 294.1x* (*ICD-9-CM code) |
| Dementia Due to Pick's Disease | 290.1x* (*ICD-9-CM code) |
| Dementia Due to Creutzfeldt-Jakob Disease | 290.1x* (*ICD-9-CM code) |
| Dementia Due to Other General Medical Conditions | 294.1x* (*ICD-9-CM code) |

Code based on presence or absence of a clinically significant behavioral disturbance:

| | |
|---|---|
| Without Behavioral Disturbance | 294.10 |
| With Behavioral Disturbance | 294.11 |

Substance-Induced Persisting Dementia
    Code [Specific Substance]-Induced Persisting Dementia:
    (291.2 Alcohol; 292.82 Inhalant; 292.82 Sedative, Hypnotic, or Anxiolytic; 292.82 Other [or Unknown] Substance)

Dementia Due to Multiple Etiologies
   Coding note: Use multiple codes based on specific dementias and specific etiologies, e.g., 294.10 Dementia of the Alzheimer's Type, With Late Onset, Without Behavioral Disturbance; 290.40 Vascular Dementia, Uncomplicated.

| | |
|---|---|
| Dementia Not Otherwise Specified | 294.8 |
| Amnestic Disorder Due to a General Medical Condition Transient or Chronic | 294.0 |

Substance-Induced Persisting Amnestic Disorder
   Code [Specific Substance]-Induced Persisting Amnestic Disorder:
   291.1 Alcohol; 292.83 Sedative, Hypnotic, or Anxiolytic; 292.83 Other [or Unknown] Substance

| | |
|---|---|
| Amnestic Disorder Not Otherwise Specified | 294.8 |
| Cognitive Disorder Not Otherwise Specified | 294.9 |
| Age-Related Cognitive Decline | 780.9 |

Examples of cognitive disorders due to various etiologies, or associated with various disorders, of particular interest that can be prevented or treated using the compounds of the present invention include: enhancing cognitive functions and executive functioning (ability to plan, initiate, organize, carry out, monitor, and correct one's own behavior) in normal subjects or in subjects exhibiting cognitive dysfunction; treatment of cognitive and attentional deficits associated with prenatal exposure to substances of abuse including, but not limited to, nicotine, alcohol, methamphetamine, cocaine, and heroin; treatment of cognitive impairment caused by chronic alcohol and drug abuse (substance-induced persisting dementia), medicament side effects, and treatment of drug craving and withdrawal; treatment of cognitive deficits in Down's Syndrome patients; treatment of deficits in normal memory functioning comorbid with major depressive and bipolar disorders; treatment of cognitive impairment associated with depression, mental retardation, bipolar disorder, or schizophrenia; treatment of dementia syndromes associated with mania, conversion disorder, and malingering; treatment of problems of attention, prefrontal executive function, or memory due to head trauma or stroke; treatment of cognitive dysfunction in menopausal and post-menopausal women and in women undergoing hormone replacement therapy; treatment of cognitive deficits and fatigue due to, or associated with, cancer and cancer therapies (cognitive deficits are associated with a variety of cancer treatments, including cranial radiation, conventional (standard-dose) chemotherapy, high-dose chemotherapy and hematopoietic (bone-marrow) transplantation, and biologic agents).

Compounds of the present invention are also useful in a method for treating a patient suffering from or susceptible to psychosis, comprising administering to said patient an effective amount of a first component which is an antipsychotic, in combination with an effective amount of a second component which is a compound of formula (I). The invention also provides a pharmaceutical composition which comprises a first component that is an antipsychotic, and a second component that is a compound of formula (I). In the general expressions of this aspect of the present invention, the first component is a compound that acts as an antipsychotic. The antipsychotic may be either a typical antipsychotic or an atypical antipsychotic. Although both typical and atypical antipsychotics are useful for these methods and formulations of the present invention, it is preferred that the first component compound is an atypical antipsychotic.

Typical antipsychotics include, but are not limited to: Chlorpromazine, 2-chloro-10-(3-dimethylaminoprop-yl) phenothiazine, is described in U.S. Pat. No. 2,645,640. Its pharmacology has been reviewed (Crismon, *Psychopharmacol. Bul.,* 4, 151 (October 1967): Droperidol, 1-(1-[3-(p-fluorobenzoyl)propyl]-1,2,3,6-tetrahydro-4-pyridyl)-2-benzimidazolinone, is described in U.S. Pat. No. 3,141,823; Haloperidol, 4-[4-(4-chlorophenyl)-4-hydroxy-1-piperidinyl]-1-(4-fluorophenyl)-1-butanone, is described in U.S. Pat. No. 3,438,991. Its therapeutic efficacy in psychosis has been reported (Beresford and Ward, *Drugs* 33, 31-49 (1987); Thioridazine, 1-hydroxy-10-[2-(1-methyl-2-pyridinyl) ethyl]-2-(methylthio)phenothiazine hydrochloride, was described by Bourquin, et al. (*Helv. Chim. Acta,* 41, 1072 (1958)). Its use as an antipsychotic has been reported (Axelsson, et al., *Curr. Ther. Res.,* 21, 587 (1977)); and Trifluoperazine, 10-[3-(4-methyl-1-piperazinyl)-propyl]-2-trifluoromethylphenthiazine hydrochloride, is described in U.S. Pat. No. 2,921,069.

Atypical antipsychotics include, but are not limited to: Olanzapine, 2-methyl-4-(4-methyl-1-piperazinyl)-10H-thieno[2,3-b][1,5]benzodiazepine, is a known compound and is described in U.S. Pat. No. 5,229,382 as being useful for the treatment of schizophrenia, schizophreniform disorder, acute mania, mild anxiety states, and psychosis; Clozapine, 8-chloro-11-(4-methyl-1-piperazinyl)-5H-dibenzo[b,e][1,4] diazepine, is described in U.S. Pat. No. 3,539,573. Clinical efficacy in the treatment of schizophrenia is described (Hanes, et al., *Psychopharmacol. Bull.,* 24, 62 (1988)); Risperidone, 3-[2-[4-(6-fluoro-1,2-benzisoxazol-3-yl)piperidino]ethyl]-2-methyl-6,7,8,9-tetrahydro-4H-pyrido[1,2-a] pyrimidin-4-one, and its use in the treatment of psychotic diseases are described in U.S. Pat. No. 4,804,663; Sertindole, 1-[2-[4-[5-chloro-1-(4-fluorophenyl)-1H-indol-3-yl]-1-piperidinyl]ethyl]imidazolidin-2-one, is described in U.S. Pat. No. 4,710,500. Its use in the treatment of schizophrenia is described in U.S. Pat. Nos. 5,112,838 and 5,238,945; Quetiapine, 5-[2-(4-dibenzo[b,f][1,4]thiazepin-11-yl-1-piperazinyl)ethoxy]ethanol, and its activity in assays which demonstrate utility in the treatment of schizophrenia are described in U.S. Pat. No. 4,879,288. Quetiapine is typically administered as its (E)-2-butenedioate (2:1) salt; Ziprasidone, 5-[2-[4-(1, 2-benzoisothiazol-3-yl)-1-piperazinyl]ethyl]-6-chloro-1,3-dihydro-2H-indol-2-one, is typically administered as the hydrochloride monohydrate. The compound is described in U.S. Pat. Nos. 4,831,031 and 5,312,925. Its activity in assays which demonstrate utility in the treatment of schizophrenia are described in U.S. Pat. No. 4,831,031; and Aripiprazole (Abilify™), 7-[4-[4-(2,3-dichlorophenyl)-1-piperazinyl]butoxy]-3,4-dihydrocarbostyril (U.S. Pat. Nos. 4,734,416 and 5,006,528) is a new antipsychotic indicated for the treatment of schizophrenia It will be understood that while the use of a single antipsychotic as a first component compound is preferred, combinations of two or more antipsychotics may be used as a first component if necessary or desired. Similarly, while the use of a single compound of formula (I) as a second component compound is preferred, combinations of two or more compounds of formula (I) may be used as a second component if necessary or desired.

While all combinations of first and second component compounds are useful and valuable, certain combinations are particularly valued and are preferred, as follows:

olanzapine/compound of formula (I)
clozapine/compound of formula (I)
risperidone/compound of formula (I)
sertindole/compound of formula (I)
quetiapine/compound of formula (I)
ziprasidone/compound of formula (I)
aripiprazole/compound of formula (I)

In general, combinations and methods of treatment using olanzapine as the first component are preferred. It is especially preferred that when the first component is olanzapine, it will be the Form II olanzapine as described in U.S. Pat. No. 5,736,541. Although Form II olanzapine is preferred it will be understood that as used herein, the term "olanzapine" embraces all solvate and polymorphic forms unless specifically indicated.

Conditions that can be treated by the adjunctive therapy aspect of the present invention include schizophrenia, schizophreniform diseases, bipolar disorder, acute mania, and schizoaffective disorders. The titles given these conditions represent multiple disease states. The following list illustrates a number of these disease states, many of which are classified in the DSM-IV-TR™. The DSM-IV-TR™ code numbers for these disease states are supplied below, when available, for the convenience of the reader.

| | |
|---|---|
| Paranoid Type Schizophrenia | 295.30 |
| Disorganized Type Schizophrenia | 295.10 |
| Catatonic Type Schizophrenia | 295.20 |
| Undifferentiated Type Schizophrenia | 295.90 |
| Residual Type Schizophrenia | 295.60 |
| Schizophreniform Disorder | 295.40 |
| Schizoaffective Disorder | 295.70 |

The present invention also encompasses the use of one or more compounds of formula (I) in combination with one or more conventional Alzheimer's agents for the prevention or treatment of cognitive dysfunction in patients suffering from Alzheimer's disease. The invention also provides a pharmaceutical composition which comprises a first component that is a conventional Alzheimer's agent and a second component that is a compound of formula (I). Conventional Alzheimer's agents include inhibitors of acetylcholine degradation (i.e., cholinesterase or acetylcholinesterase inhibitors) within synapses, e.g., donepezil (Aricept®), rivastigmine (Exelon®), galantamine (Reminyl®), and tacrine (Cognex®); the selective monoamine oxidase inhibitor selegiline (Eldepryl®); and memantine (Namenda™), a newly FDA-approved NMDA receptor antagonist for the treatment of moderate to severe Alzheimer's disease. Modafinil (Provigil®) is also used in the treatment of Alzheimer's disease.

The present invention also encompasses the use of one or more compounds of formula (I) in combination with one or more conventional Parkinson's agents for the treatment of cognitive dysfunction in Parkinson's disease. The invention also provides a pharmaceutical composition which comprises a first component that is a conventional Parkinson's agent and a second component that is a compound of formula (I). Conventional Parkinson's agents include levodopa; levodopa/carbidopa (Sinemet®); Stalevo (carbidopa/levodopa/entacapone); dopamine agonists, e.g., bromocriptine; Mirapex® (pramipexole), Permax® (pergolide), and Requip® (ropinirole); COMT inhibitors, e.g., tolcapone, and entacapone; Selegiline (Deprenyl®; Eldepryl®); propranolol; primidone; anticholinergics, e.g., Cogentin®, Artane®, Akineton®, Disipal®, and Kemadrin®; and amantadine.

In each of the combination treatments mentioned above, said first and second components may be administered simultaneously, separately or sequentially. Similarly, said compositions encompass combined preparations for simultaneous, separate or sequential use.

The term "teatment" as used herein refers to both curative and prophylactic treatment of disorders associated with norepinephrine dysfunction. Thus, the term "treatment" is intended to refer to all processes wherein there may be a slowing, interrupting, arresting, controlling, or stopping of the progression of the disorders described herein, but does not necessarily indicate a total elimination of all symptoms, and is intended to include prophylactic and therapeutic treatment of such disorders.

The compounds of the present invention are also indicated for the treatment of disorders which are ameliorated by an increase in the amount of norepinephrine neurotransmitter within the synaptic cleft of a mammal above that which would be considered to be normal or desirable for the mammalian species, or an individual within the species, in question.

In another embodiment of the present invention, there is provided a pharmaceutical composition comprising a compound of formula (I) or a pharmaceutically acceptable salt thereof together with a pharmaceutically acceptable diluent, excipient or carrier.

In another embodiment of the present invention, there is provided a compound of formula (I) or a pharmaceutically acceptable salt thereof for use in therapy.

In another embodiment of the present invention, there is provided a compound of formula (I) or a pharmaceutically acceptable salt thereof for use as an inhibitor of the reuptake of norepinephrine. Preferably such inhibition occurs within mammalian cells (including mammalian cell membrane preparations), especially those found within the central and/or peripheral nervous system. More preferably such inhibition occurs within the cells of the central nervous system of a mammal, especially a human, in need thereof.

In another embodiment of the present invention there is provided a compound of formula (I) or a pharmaceutically acceptable salt thereof for treating disorders associated with norepinephrine dysfunction in mammals.

In another embodiment of the present invention, there is provided the use of a compound of formula (I) or a pharmaceutically acceptable salt thereof for the manufacture of a medicament for inhibiting the reuptake of norepinephrine.

In another embodiment of the present invention, there is provided the use of a compound of formula (I) or a pharmaceutically acceptable salt thereof for the manufacture of a medicament for the treatment of disorders associated with norepinephrine dysfunction in mammals.

In another embodiment of the present invention, there is provided a method for inhibiting the reuptake of norepinephrine in mammals comprising administering to a patient in need thereof an effective amount of a compound of formula (I) or a pharmaceutically acceptable salt thereof.

In another embodiment of the present invention, there is provided a method for treating disorders associated with norepinephrine dysfunction in mammals comprising administering to a patient in need thereof an effective amount of a compound of formula (I) or a pharmaceutically acceptable salt thereof.

The present invention includes the pharmaceutically acceptable salts of the compounds of formula (I). Suitable salts include acid addition salts, including salts formed with inorganic acids, for example hydrochloric, hydrobromic, nitric, sulphuric or phosphoric acids, or with organic acids, such as organic carboxylic or organic sulphonic acids, for example, acetoxybenzoic, citric, glycolic, mandelic-l, mandelic-dl, mandelic-d, maleic, mesotartaric monohydrate, hydroxymaleic, fumaric, lactobionic, malic, methanesulphonic, napsylic, naphthalenedisulfonic, naphtoic, oxalic, palmitic, phenylacetic, propionic, pyridyl hydroxy pyruvic, salicylic, stearic, succinic, sulfanilic, tartaric-l, tartaric-dl, tartaric-d, 2-hydroxyethane sulphonic, toluene-p-sulphonic, and xinafoic acids.

The compounds of the present invention may be used as medicaments in human or veterinary medicine. The compounds may be administered by various routes, for example, by oral or rectal routes, topically or parenterally, for example by injection, and are usually employed in the form of a pharmaceutical composition.

Such compositions may be prepared by methods well known in the pharmaceutical art and normally comprise at least one active compound in association with a pharmaceutically acceptable diluent, excipient or carrier. In making the compositions of the present invention, the active ingredient will usually be mixed with a carrier or diluted by a carrier, and/or enclosed within a carrier which may, for example, be in the form of a capsule, sachet, paper or other container. Where the carrier serves as a diluent, it may be solid, semisolid, or liquid material which acts as a vehicle, excipient or medium for the active ingredient. Thus, the composition may be in the form of tablets, lozenges, sachets, cachets, elixirs, suspensions, solutions, syrups, aerosols (as a solid or in a liquid medium), ointments containing, for example, up to 10% by weight of the active compound, soft and hard gelatin capsules, suppositories, injection solutions and suspensions and sterile packaged powders.

Some examples of suitable carriers are lactose, dextrose, vegetable oils, benzyl alcohols, alkylene glycols, polyethylene glycols, glycerol triacetate, gelatin, carbohydrates such as starch and petroleum jelly, sucrose sorbitol, mannitol, starches, gum acacia, calcium phosphate, alginates, tragacanth, gelatin, syrup, methyl cellulose, methyl- and propylhydrobenzoate, talc, magnesium stearate and mineral oil. The compounds of formula (I) can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins. Compositions of the invention may be formulated so as to provide, quick, sustained or delayed release of the active ingredient after administration to the patient by employing procedures well known in the art.

The compositions are preferably formulated in a dosage unit form, each dosage unit containing from about 5 to about 500 mg, more usually about 25 to about 300 mg, of the active ingredient. The term "dosage unit form" refers to physically discrete units suitable as unitary doses for human subjects and other mammals, each unit containing a predetermined quantity of active material calculated to produce the desired therapeutic effect, in association with a suitable pharmaceutical carrier.

Compounds of the present invention may be prepared by conventional organic chemistry techniques. General schemes outlining the synthetic routes to compounds of the present invention are described below. For clarity, Rx, Ry and Rz are shown as H, however, it will be appreciated that analogous methods could be applied for other possible identities of Rx, Ry and Rz.

The intermediates of formulae (X), (XI), (XII), (XV) and (XVI) may be prepared as shown below (where P represents a N-protecting group and R7 and R8, which may be the same or different, each represent C1-C4 alkyl (optionally substituted with one OMe group), or, taken together with the N atom to which they are attached, form a pyrrolidine, piperidine or morpholine ring):

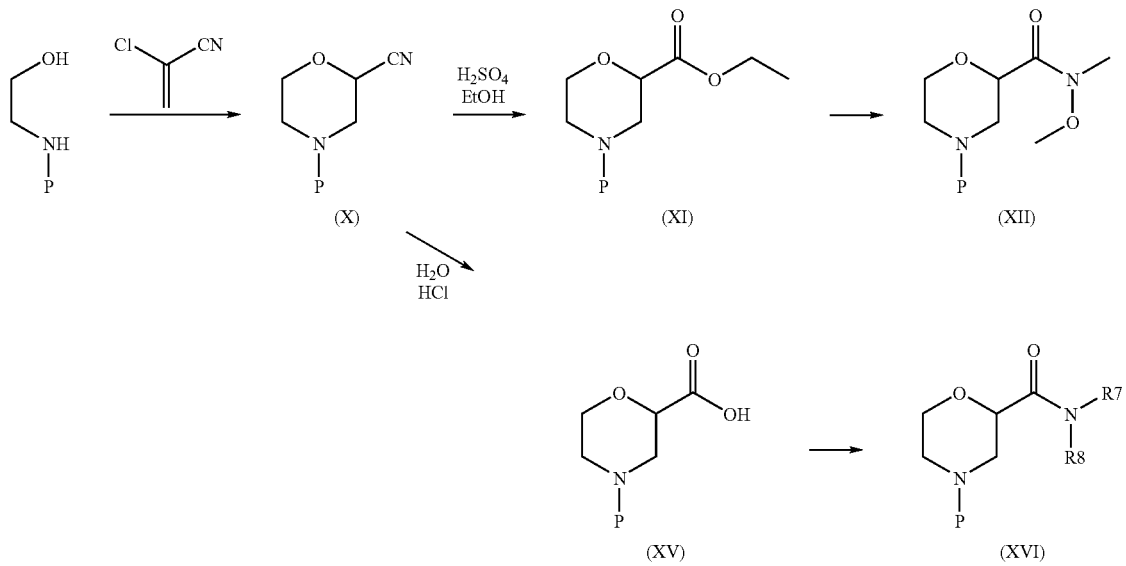

N-protected ethanolamine is reacted with 2-chloroacrylonitrile to give a Michael adduct which is then treated in situ with a base, such as potassium t-butoxide, to give a compound of formula (X). The compound of formula (X) may then be hydrolysed in $H_2SO_4$/ethanol to give the ester of formula (XI). This in turn may be converted into the Weinreb amide of formula (XII) by adding a solution of (XI) to a premixed solution of N,N'-dimethylhydroxylamine and trimethylaluminium. Alternatively, the compound of formula (X) may be hydrolysed in H₂O/HCl to give the acid of formula (XV). This in turn may be converted into the amide of formula (XVI) by reacting a solution of (XV) with oxalyl chloride or SOCl₂ to provide an acyl chloride which is then reacted with an amine of the formula R7R8NH such as dimethylamine or morpholine. The preferred enantiomers of the amides (XII) and (XVI) shown below may be obtained by chiral chromatography.

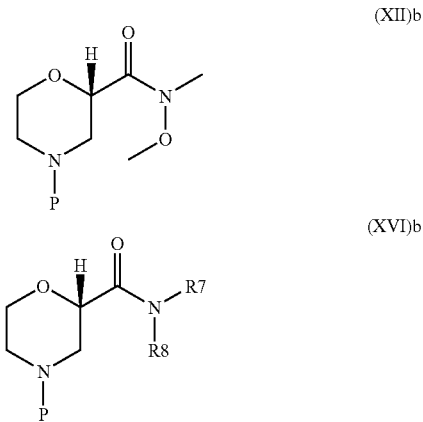

Suitable N-protecting groups will be known to the person skilled in the art. Further information on suitable N-protecting groups is contained in the well known text "Protective Groups in Organic Synthesis", Theodora W. Greene and Peter G. M. Wuts, John Wiley & Sons, Inc., New York, 1999, pp. 494-653. Benzyl is an especially preferred N-protecting group.

N-protected compounds of formula (I) wherein X is NH₂ may be prepared from compounds of formula (X) as shown below:

In route A the intermediate (X) is treated with an excess of the Grignard reagent Ar1CH₂MgBr to provide an N-protected compound of formula (I) wherein X is NH₂ and R1 is CH₂Ar2 wherein Ar2=Ar1. In route B the intermediate (X) is treated with one equivalent of the Grignard reagent R1MgBr followed by one equivalent of the Grignard reagent Ar1CH₂MgBr to provide an N-protected compound of formula (I) wherein X is NH₂. Alternatively, the Grignard reagent Ar1CH₂MgBr may be added first followed by R1MgBr. Preferably, a Lewis acid such as titanium isopropoxide is added to the reaction mixture in between addition of the Grignard reagents (see Charette, A. B.; Gagnon, A; Janes, M; Mellon, C; Tetrahedron Lett, 1998, 39(29), 5147-5150 and Charette, A. B.; Gagnon, A; Tetrahedron: Asymmetry, 1999, 10(10), 1961-1968).

N-protected compounds of formula (I) wherein X is OH and R1 is CH₂Ar2 wherein Ar2=Ar1 may be prepared from compounds of formula (XI) as shown below:

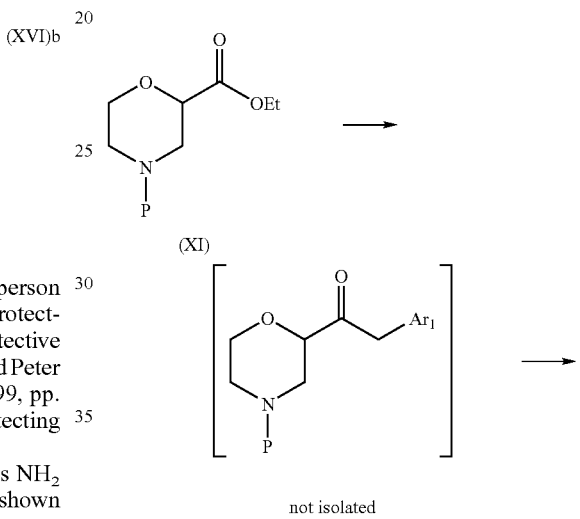

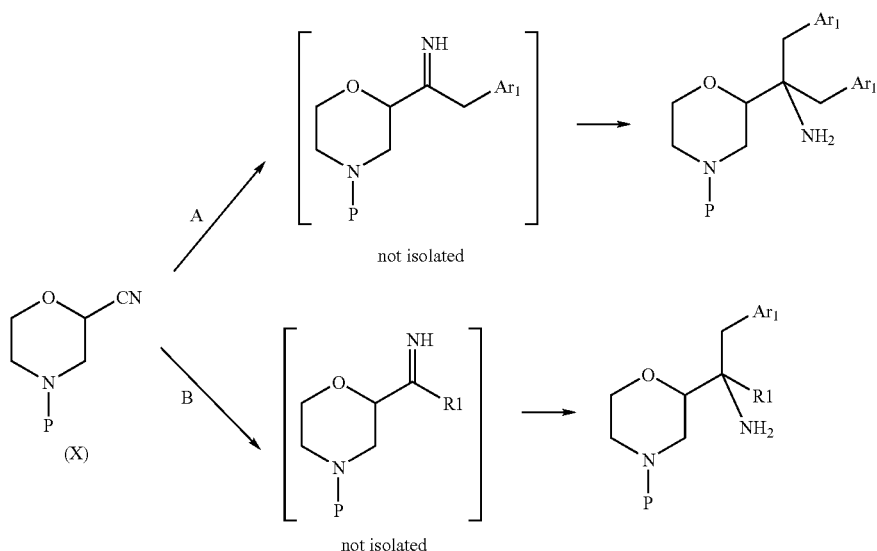

-continued

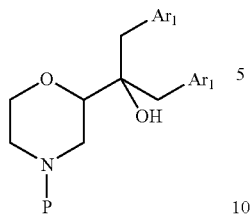

Intermediate (XI) is treated with an excess of the Grignard reagent Ar1CH$_2$MgBr to provide an N-protected compound of formula (I) wherein X is OH and R1 is CH$_2$Ar2 wherein Ar2=Ar1.

N-protected compounds of formula (I) wherein X is OH may be prepared from the Weinreb amide of formula (XII) or the amide of formula (XVI) as shown below:

omer (XIII)b the reaction proceeds stereoselectively to provide an N-protected compound of formula (II) wherein X is OH.

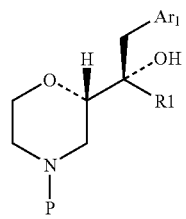

The ketones of formula (XIII) may also be obtained via a different route as shown below:

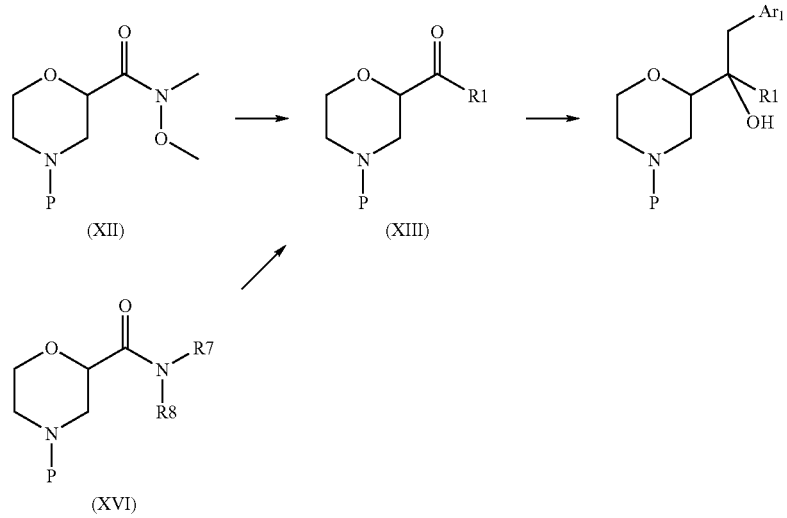

To a solution of (XII) or (XVI) is added a solution of the requisite Grignard reagent R1MgBr to provide, on work up, a compound of formula (XI). When the reaction is conducted using the preferred enantiomers (XII)b or (XVI)b it proceeds with retention of stereochemistry to provide (XIII)b.

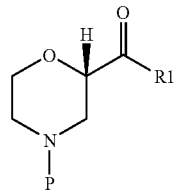

(XIII)b

To a solution of the ketone of formula (XIII) is added a solution of the Grignard reagent Ar1CH$_2$MgBr to provide an N-protected compound of formula (I) wherein X is OH. When the reaction is conducted using the preferred enanti-

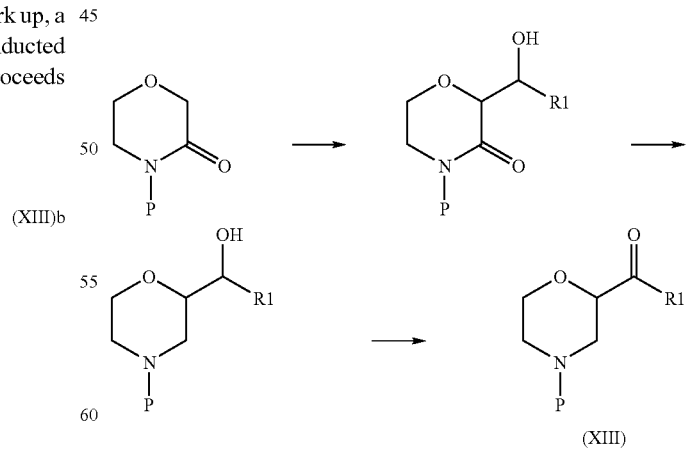

A solution of N-protected morpholinone is treated with a strong base such as lithium diisopropylamide. To this solution is added an aldehyde R1CHO. Reduction of the morpholine carbonyl group using, for example, borane-THF complex followed by oxidation of the alcohol using, for example, Swern oxidation conditions, provides a compound of formula (XII) which can be reacted onward as described in the previous scheme to provide a N-protected compound of formula (I) wherein X is OH.

N-protected compounds of the present invention wherein X is C1-C4 alkoxy, may be synthesized by standard alkylation of the N-protected compounds of formula (I) wherein X=OH as shown below:

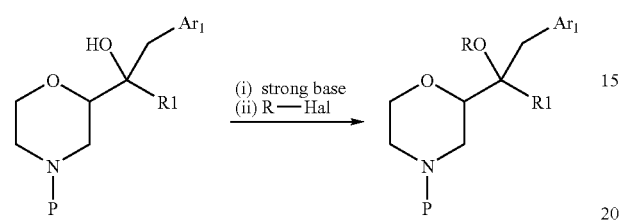

Suitable strong bases will be known to the person skilled in the art and include, for example, sodium hydride. Similarly, suitable alkylating agents will be known to the person skilled in the art and include, for example, $C_1$-$C_4$ alkyl halides such as methyl iodide.

N-protected compounds of the present invention wherein X is NH(C1-C4 allyl), may be synthesized by treatment of a compound of formula (I) wherein X=NH$_2$ under reductive alkylating conditions or using suitable alkylating agents known to the person skilled in the art including, for example, C1-C4 alkyl halides such as methyl iodide.

N-protected compounds of the present invention may be elaborated upon using standard organic chemistry to provide further N-protected compounds of the present invention. For example, organometallic type couplings between an Ar1-Br derivative and a phenylboronic acid as shown below can provide Ar1-phenyl derivatives.

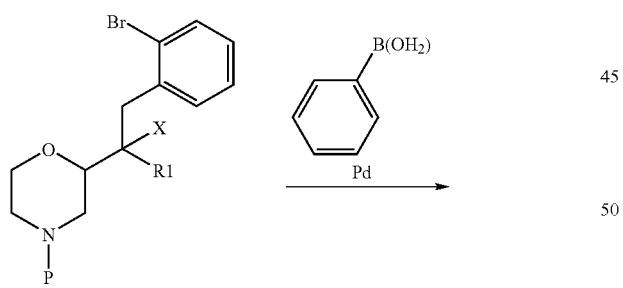

Compounds of formula (I) may be obtained by deprotection of the N-protected intermediates as shown below:

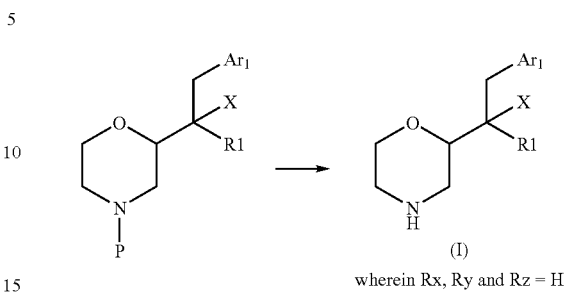

Further information on suitable deprotection methods is contained in the well known text "Protective Groups in Organic Synthesis" referenced above.

Thus, in another embodiment of the present invention there is provided a process for the preparation of compounds of formula (I) comprising the step of deprotecting a compound of the formula (XIV)

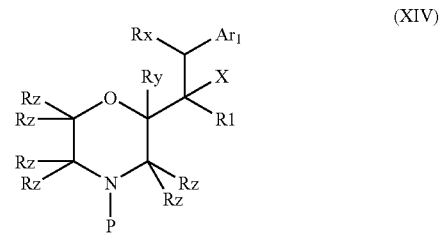

wherein P represents a N-protecting group and all other variables are as defined for formula (I) above, to provide a compound of formula (I), optionally followed by the step of forming a pharmaceutically acceptable salt.

Examples of compounds of the present invention may be prepared by conventional organic chemistry techniques from N-benzyl-morpholine-2-carboxylic acid ethyl ester 1 or N-benzylmorpholinone as outlined in Schemes 1-4.

Scheme 1

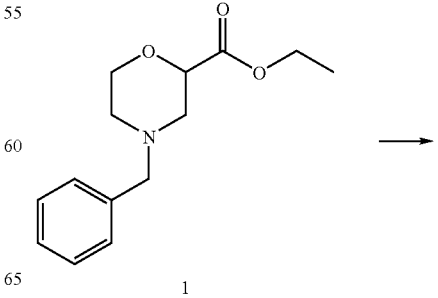

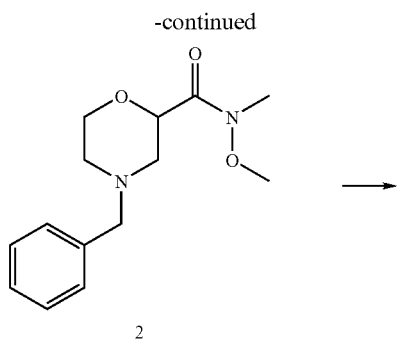

2

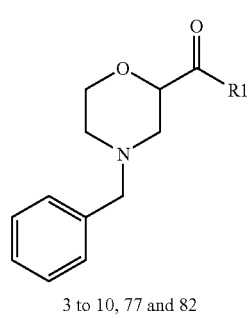

3 to 10, 77 and 82

Conversion of 1 into Weinreb amide 2 followed by treatment with a suitable Grignard reagent leads to ketones of formula (XII) wherein P is benzyl as listed in Table 1.

TABLE 1

| R1 | Compound# (Ketone) |
| --- | --- |
| methyl | 3 |
| ethyl | 4 |
| isopropyl | 5 |
| isobutyl | 6 |
| cyclopentyl | 7 |
| tetrahydropyranyl | 8 |
| 3,3,3-trifluoropropyl | 9 |
| 4,4,4-trifluorobutyl | 10 |
| cyclopropyl | 77 |
| n-butyl | 82 |

Cyclopropyl-substituted ketone 77 may alternatively be obtained from N-benzyl morpholinone as outlined in Scheme 2.

Scheme 2

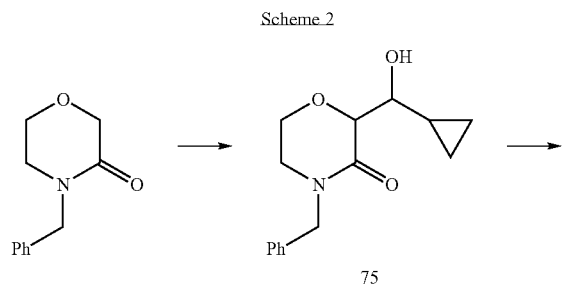

75

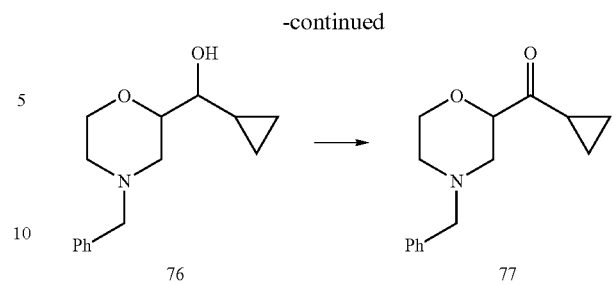

76                                77

Treatment of the N-benzyl-morpholinone with a strong base such as lithium diisopropylamide followed by addition of cyclopropyl methylaldehyde gives 75. Reduction of 75 with, for example, borane-THF complex gives 76. Addition of a solution of 76 to a pre-mixed solution of dimethylsulfoxide and oxalyl chloride provides 77.

Reaction of ketones listed in Table 1 with a suitably substituted benzyl Grignard reagent gives N-benzyl substituted tertiary alcohols listed in Table 2 (wherein R2, R5 and R6 are H unless otherwise indicated) as outlined in Scheme 3.

Scheme 3

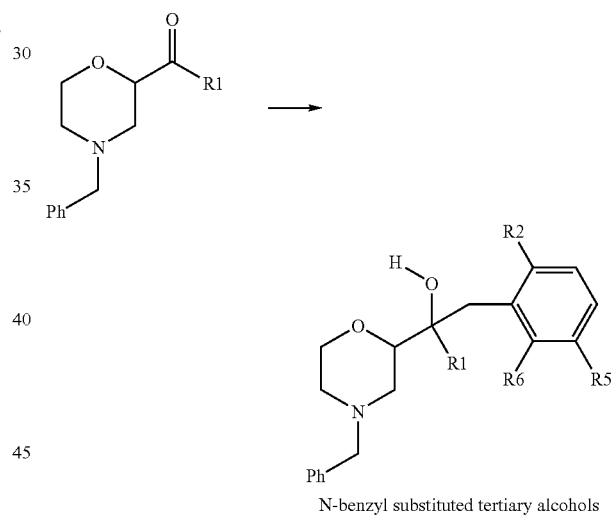

N-benzyl substituted tertiary alcohols

Debenzylation and salt formation as detailed in Scheme 4 leads to the tertiary alcohol salts listed in Table 2 (wherein R2, R5 and R6 are H unless otherwise indicated).

Scheme 4

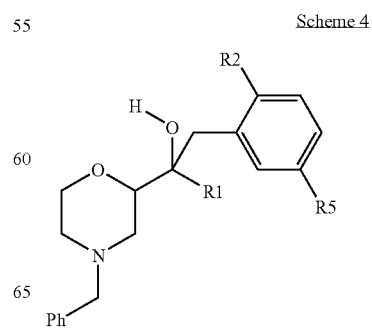

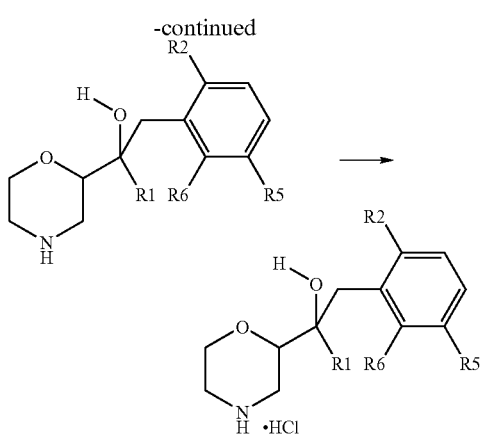

TABLE 2

| Example | R1 | R2, R5, R6 | Compound# (N-Benzyl intermediate) | Compound# (HCl Salt) |
|---|---|---|---|---|
| 1 | methyl | 2-Ph | 11 | 12 |
| 2 | ethyl | 2-OMe, 5-F | 13 | 14 |
| 3 | ethyl | 2-OCF₃ | 15 | 16 |
| 4 | ethyl | 2-Ph | 17 | 18 |
| 5 | isopropyl | 2-OMe, 5-F | 19 | 20 |
| 6 | isopropyl | 2-OMe | 21 | 22 |
| 7 | isopropyl | 2-OEt | 23 | 24 |
| 8 | isopropyl | 2-OCF₃ | 25 | 26 |
| 9 | isopropyl | 2-Ph | 27 | 28 |
| 10 | isopropyl | 2-Ph, 5-F | 29 | 30 |
| 11 | isobutyl | 2-OMe, 5-F | 31 | 32 |
| 12 | isobutyl | 2-OEt | 33 | 34 |
| 13 | isobutyl | 2-OCF₃ | 35 | 36 |
| 14 | isobutyl | 2-Ph | 37 | 38 |
| 15 | isobutyl | 2-Ph, 5-F | 39 | 40 |
| 16 | cyclopentyl | 2-OMe, 5-F | 41 | 42 |
| 17 | cyclopentyl | 2-OEt | 43 | 44 |
| 18 | cyclopentyl | 2-OCF₃ | 45 | 46 |
| 19 | cyclopentyl | 2-Ph | 47 | 48 |
| 20 | cyclopentyl | 2-Ph, 5-F | 49 | 50 |
| 21 | tetrahydropyranyl | 2-OMe, 5-F | 51 | 52 |
| 22 | tetrahydropyranyl | 2-OCF₃ | 53 | 54 |
| 23 | tetrahydropyranyl | 2-Ph | 55 | 56 |
| 24 | tetrahydropyranyl | 2-(3-F-Ph) | 57 | 58 |
| 25 | 3,3,3-trifluoropropyl | 2-OMe, 5-F | 59 | 60 |
| 26 | 3,3,3-trifluoropropyl | 2-OCF₃ | 61 | 62 |
| 27 | 3,3,3-trifluoropropyl | 2-Ph | 63 | 64 |
| 28 | 4,4,4-trifluorobutyl | 2-OMe, 5-F | 65 | 66 |
| 29 | 4,4,4-trifluorobutyl | 2-Ph | 67 | 68 |
| 30 | cyclopropyl | 2-OMe | 69 | 70 |
| 31 | cyclopropyl | 2-OEt | 71 | 72 |
| 32 | cyclopropyl | 2-Ph | 73 | 74 |
| 35 | n-butyl | 2-OMe | 83 | 84 |
| 36 | n-butyl | 2-Ph | 85 | 86 |
| 37 | isobutyl | 2-Cl, 6-F | 87 | 88 |
| 38 | isobutyl | 2-Cl | 89 | 90 |

The compounds of Examples 1 to 32 and 35 to 38 can be obtained in enantiomerically pure form via this route using chirally pure ester 1. Resolution of 1 into its enantiomers can be achieved through chiral HPLC. Conversion of the ester to the Weinreb amide does not disturb the chiral center thus providing chirally pure amide 2. Conversion of the Weinreb amide to the ketone also does not disturb the chiral center thus providing chirally pure ketones 3 to 10, 77 and 82. Alternatively, chiral separation may conducted on the amide 2 through chiral HPLC to provide its enantiomers. Alternatively, chiral separation may conducted on the ketones 3 to 10, 77 and 82 through chiral HPLC to provide their enantiomers. Chiral separation of the ester, amide or ketones may also be achieved by other techniques known to those skilled in the art, such as fractional crystallization of diasteromeric salts formed with chiral acids. Addition of the benzyl Grignard reagent (Scheme 3) is a stereoselective process and gives predominantly one diastereomer with only small amounts of the second diastereomer. No epimerisation is observed during removal of the benzyl group. Alternatively, enantiomerically pure products are obtained through conversion to an N-protected analogue such as butyloxycarbonyl or carbobenzyloxy followed by separation by chiral HPLC. Removal of the N-protecting group leads to enantiomerically highly enriched products.

In the experimental procedures described below the following abbreviations are used:
HPLC=high performance liquid chromatography
THF=tetrahydrofuran
2-MeTHF=2-methyltetrahydrofuran
DIBALH=diisobutyl aluminium hydride
DCM=dichloromethane
FIA⁺ (or FIA-MS)=fast-ionisation-analysis mass spectrometry
LCMS=liquid chromatography mass spectroscopy
NMR=nuclear magnetic resonance
MW=molecular weight
MeOH=methanol
EtOAc or AcOEt=ethyl acetate
PS-DIEA=polymer-supported diisopropylethylamine
DEA=diethylamine
$R_T$=retention time
cbz=carbobenzyloxy
h, hr or hrs=hour or hours
min or mins=minute or minutes
ee=enantiomeric excess
de=diastereomeric excess
eq or equiv.=equivalent
ACN=acetonitrile
DMF=dimethylformamide
DMEA=N,N-dimethylethanolamine
NH₃aq=25 wt % aqueous ammonia
Tmass=temperature of the reaction mixture The analytical LCMS data reported refers either to:

(i) a 6 minute run, performed on a column (C18 50×3 mm 5 µm) using a gradient [90% H₂O (+0.04% formic acid) to 90% ACN (+0.04% formic acid)] over 4 minutes and then hold for 2 minutes; or (ii) a 12 minute run, performed on a column (C18 100×3 mm 5 µm) using a gradient [90% H₂O (+0.04% formic acid) to 90% ACN (+0.04% formic acid)] over 9 minutes and then hold for 3 minutes.

GENERAL SYNTHETIC PROCEDURES FOR THE PREPARATION OF EXAMPLES 1 TO 32 AND 35 TO 38

General Procedure 1: Preparation of N-Benzyl Morpholine Alkyl Ketones

To a solution of the carboxamide 2 in anhydrous THF at 0° C. is added a solution of the requisite Grignard reagent (1.2-3 eq in one or two aliquots). The reaction mixture is allowed to warm up to room temperature and left stirring for 45 minutes to 2 hours before quenching either with 1M hydrochloric acid or saturated ammonium chloride solution and extracting either in DCM or ethyl acetate. The combined organic layers are dried over magnesium sulphate, filtered and concentrated in vacuo to give the corresponding alkyl ketones 3-10, 77 and 82.

General Procedure 2: Preparation of N-Benzyl Tertiary Alcohols

To a solution of the ketones 3-10, 77 and 82 in anhydrous THF at 0° C. is added a solution of the requisite benzyl Grignard reagent (1.1-1.5 eq). The reaction mixture is allowed to warm up to room temperature and left stirring for 1-2 hours before quenching by addition of cold water. After extraction of the aqueous layer in DCM, the combined organic layers are washed with brine, dried over magnesium sulphate, filtered and concentrated in vacuo to give the title N-benzyl tertiary alcohols. Purification details are listed for individual compounds.

General Procedure 3: Debenzylation of N-Benzyl Tertiary Alcohols

To a solution of the requisite N-benzyl tertiary alcohol in anhydrous DCM is added solid supported Hünig's base (Argonaut, 3.56 mmol/g, 24 eq) and α-chloroethyl chloroformate (3 to 10 eq) at room temperature under nitrogen. The reaction mixture is heated to 40° C. and the reaction is monitored by FIA$^+$ and LCMS analysis. After completion the reaction mixture is filtered, and the resin washed with DCM. The combined organic phases are concentrated in vacuo. Methanol is added and the solution heated to 60° C. for 1.5 to 8 hours. After complete consumption of starting material the methanol solution is evaporated to give a product, which is flirter purified as detailed for individual compounds.

General Procedure 4: Conversion of Amines into Hydrochloride Salts

To a solution of the requisite amine in dry diethyl ether (5-10 mL) is added hydrochloric acid (1.2 eq, 1M solution in diethyl ether). Ether is blown off with a stream of nitrogen or removed in vacuo and the samples were either dried under high vacuum for several hours or freeze-dried (acetonitrile/water 1/1 [v/v]) to give the hydrochloride salts in near quantitative yield.

General Procedure 5: Preparation of Grignard Reagents and Benzyl Grignard Reagents Such reagents were prepared from the requisite halide or benzyl halide using methods known to those skilled in the art (see for example Fieser, L. F. and Fieser, M. F. "Reagents for Organic Synthesis", John Wiley and Sons Inc., Vol. 1, pp. 415-424 or March, J. "Advanced Organic Chemistry", John Wiley and Sons Inc., 3$^{rd}$ Ed., pp. 558-561). The requisite halides or benzyl halides were either commercially available or prepared using previously published literature methods.

PREPARATION OF INTERMEDIATES FOR THE SYNTHESIS OF EXAMPLES 1-32

4-Benzyl-morpholine-2-carbonitrile

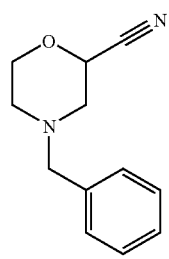

A one-litre reactor with mechanical stirring, cooled by an ice bath, is charged with N-benzylethanolamine (172.2 g; 1 equiv. available from Aldrich Chemical Company). 2-Chloroacrylonitrile (100 g; 1 equiv. available from Aldrich Chemical Company) is added dropwise over 2 minutes. The temperature is maintained between 23° C. and 29° C. by means of the ice bath and subsequently a water bath at 15° C. After one night stirring at room temperature (water bath), the mixture is dissolved in tetrahydrofuran and transferred to a 2 L reactor which is cooled to −5° C. by ice/NaCl bath. The total volume of tetrahydrofuran is 1.35 L. Potassium tert-butoxide (148 g; 1.1 equiv.) is added by portions over 1 hour, keeping the reaction temperature at 0±2° C. After 1 hour post-stirring at 0° C., the mixture is quenched with saturated NaHCO$_3$ (500 mL). The aqueous layer is extracted with diethyl ether (500 mL). Organic layers are dried over MgSO$_4$ and evaporated to dryness. The title compound (149.8 g; 65%) is obtained after percolation of the 250 g dry residue on 1 kg of SiO$_2$, eluting with the following gradient:

| | |
|---|---|
| 5% AcOEt-95% n-heptane | 2.5 L |
| 10% AcOEt-90% n-heptane | 2 L |
| 15% AcOEt-85% n-heptane | 2 L |
| 20% AcOEt-80% n-heptane | 5 L |

Alternatively, this intermediate may be prepared as follows:

A 1600 L glass-lined reactor under N$_2$ is successively loaded with 2-chloroacrylonitrile (33.2 kg, 379 moles) and toluene (114 L) at 21° C. Then, N-benzylethanolamine (57 kg, 377 moles) is added and the reaction mixture is post-agitated at room temperature for about 17 h. Then, the mixture is diluted with toluene (336 L), cooled down to about −12° C. and potassium t-butoxide (42.3 kg, 377 moles) is added in portions (10) maintaining about −13° C.≦Tmass≦about −2° C. The mixture is post-agitated at about 0° C. for 2.5 h, then quenched by adding water (142.5 L) maintaining about 2° C.≦Tmass≦about 8° C. The aqueous layer is separated after 35 minutes of post-stirring allowing the mixture to reach 15° C. and the toluene layer is washed with water (142.5 L) and the aqueous layer is separated. The organic layer is then concentrated under reduced pressure (150 mbars) maintaining Tmass≦60° C. in order to distill 162 kg of toluene. The filtrates are then diluted with toluene (114 L) and treated with SiO$_2$ (Merck silica gel 60, 0.063-0.1 mm, 74.1 kg) under agitation at room temperature for 1.25 h. SiO$_2$ is filtered and rinsed with toluene (2×114 L). Then, the filtrates are concentrated under reduced pressure (150 mbars) maintaining Tmass≦60° C. in order to distill 351.8 kg of toluene.

4-Benzyl-morpholine-2-carboxylic acid hydrochloride (91)

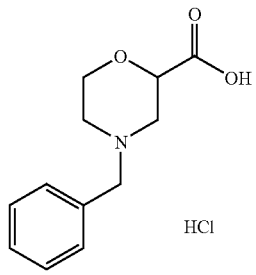

A 500 mL reactor under N₂ is successively loaded with toluene (36.72 mL) and 2-chloroacrylonitrile (10.7 g, 122.23 mmol) at room temperature. Then, N-benzyl ethanolamine (18.36 g, 121.14 mmol) is added over 5 min and the reaction mixture is post-agitated at room temperature for 16 h. Then, the mixture is diluted with toluene (110.16 mL), cooled to −5° C. and 2M potassium tert-butoxide solution in THF (121.14 mmol) is slowly added over 30 min, maintaining the temperature at −5° C. to 0° C. The mixture is post-agitated at about −5° C. to 0° C. for 1 h, then quenched by adding water (45.9 mL). The aqueous layer is separated and the toluene layer is washed with water (45.9 mL) and then the mixture is allowed to warm to room temperature. The organic layer is then concentrated under reduced pressure at 40° C. Then, the mixture is diluted with toluene (100 mL) and extracted with 6N HClaq (162 mL). This aqueous layer is heated up to the reflux for 1 h 30, then the mixture is allowed to stir at room temperature overnight. After crystallization of 91, the solid is filtered, rinsed with 6N HClaq (40 mL) and dried under reduce pressure at 40° C. (19 g, yield=61%).

N-benzyl-2-(morpholin-4-carbonyl)-morpholine hydrochloride (92)

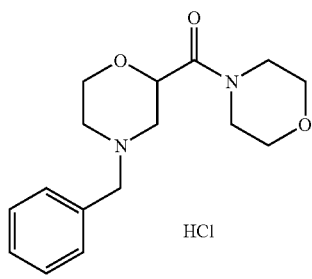

A 250 mL reactor under N₂ is successively loaded with 91 (5 g, 19.41 mmol), dichloroethane (50 mL), DMF (0.014 mL, 1% mol) and oxalyl chloride (1.86 mL, 21.35 mmol). The mixture is heated up to 60-65° C. for 2 h, before being cooled to 0° C. Then, morpholine (6.93 g, 79.60 mmol) in dichloroethane (20 mL) is added over 15 min keeping the temperature below 10° C. The heterogeneous solution is post-agitated for 1 h 30 min at room temperature and quenched with water (30 mL). The biphasic mixture is filtered on a Hyflo Super Cel® (10 g), then after separation, the organic layer is concentrated under reduce pressure. The mixture is taken up with isopropanol (80 mL) and 12N HClaq (1.61 mL, 19.41 mmol), stirred for 10 min and concentrated under reduce pressure. The mixture is taken up with isopropanol (13 mL), heated to reflux until a homogeneous solution is formed, then it is cooled to room temperature. The precipitate is filtered, rinsed with isopropanol (10 mL) and dried under vacuum at 40° C. overnight to obtain 92 as an off-white powder with 79% overall yield.

4-Benzyl-morpholine-2-carboxylic acid ethyl ester (1)

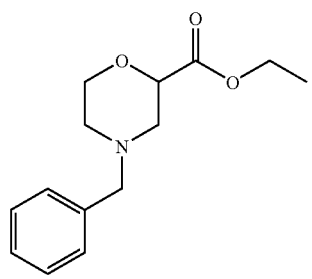

A stirred solution of 4-benzyl-morpholine-2-carbonitrile (113.0 g, 0.56 mol) in ethanol (1030 mL) is treated with concentrated sulphuric acid (165 mL) added in portions. (exothermic, internal temperature rises from ambient to 65° C.). The mixture is then warmed under reflux for 66 hrs. The solution is cooled and then concentrated in vacuo to half volume, basified with aqueous potassium carbonate (beware frothing) and the product extracted into diethyl ether. The organic phase is dried over magnesium sulphate, filtered and evaporated to dryness in vacuo to yield an oil. This material is evacuated further under high vacuum. Yield=121.3 g (87%).

Alternatively, compound 1 may be synthesised as follows:

A 100 L reactor attached to a scrubber filled with 1N NaOH (60 L) is charged under nitrogen atmosphere with 4-benzyl-morpholine-2-carbonitrile (1867 g, 9.23 mol) and ethanol (20 L). At Tmass=15-20° C., concentrated sulfuric acid (2.76 L, 50 mol) is added to the solution over 20 min (highly exothermic). The solution is heated to reflux for 2.5 days. Then, 10 L of solvent is distilled off under vacuum and the reaction mixture is cooled to Tmass=20-25° C. Water (40 L) is added over 25 min followed by Na₂CO₃ solution (1/2 saturated, 18 L) and NaHCO₃ (1/2 saturated, 7 L) to reach a pH 7. Ethyl acetate is added (15 L) and the phases are mixed for 15 min. The organic phase is separated and the aqueous phase is extracted with ethyl acetate (2×10 L). The combined organic layers are evaporated to dryness under vacuum to give 1 as a yellow to brown oil (1992 g, 87%)

4-Benzyl-morpholine-2-carboxylic acid ethyl ester (1b)

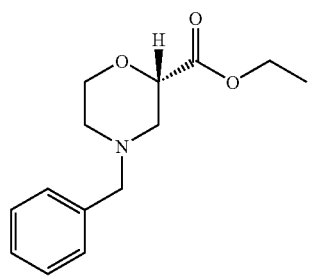

Compound 1 may be separated into its enantiomers by chiral HPLC under the following conditions: Daicel Chiralpak OJ 20 μm; 25 cm; 100% EtOH+0.3% DMEA; 0.4 mL/min; detection at 260 nm. The desired enantiomer 1b is the peak eluting at $R_T$=20.25 min.

4-Benzyl-morpholine-2-carboxylic acid methoxy-methyl-amide (2)

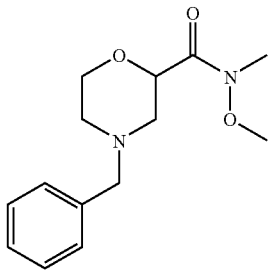

To a stirred suspension of N,N-dimethylhydroxylamine (6.6 g, 67.6 mmol) in anhydrous DCM (200 mL) under nitrogen at 0° C. is added dropwise a solution of trimethylaluminium (2M solution in hexane, 34 mL, 67.6 mmol) over 30 minutes. The reaction mixture is allowed to warm up to room temperature and left stirring for 1 hour. A solution of the ester 1 (6.74 g, 27 mmol) in anhydrous DCM (100 mL) is then added dropwise over 30 minutes and the reaction mixture is left stirring overnight before quenching by cautious addition of phosphate buffer (disodium hydrogen phosphate, pH 8) solution. The precipitate is removed by filtration through a celite pad and the residue washed with chloroform. The organic phase is then concentrated in vacuo and washed with water. The aqueous layer is re-extracted with chloroform and the organic phases are combined, washed with brine, dried over magnesium sulphate and the solvent evaporated in vacuo to give 2 as a yellow oil. Alternatively, the reaction could be worked up as follows: upon addition of a solution of the ester 1 (1 eq) the reaction mixture is left stirring for 1 hour before quenching by addition of phosphate buffer (disodium hydrogen phosphate, pH 8) solution, followed by addition of water. The aqueous layer is re-extracted with DCM and the organic phases are combined, dried over magnesium sulphate and the DCM evaporated in vacuo to give 2 as a yellow oil (3.36 g, 47%). MW 264.33; $C_{14}H_{20}N_2O_3$; $^1$H NMR (CDCl$_3$): 7.47-7.22 (5H, m), 4.55 (1H, d, 1.5 Hz), 4.00 (1H, dd, 11.5 Hz, 1.7 Hz), 3.75 (1H, dt, 11.5 Hz, 2.2 Hz), 3.65 (3H, s), 3.56 (2H, m), 3.17 (3H, s), 2.93 (1H, d, 11.3 Hz), 2.68 (1H, d, 11.3 Hz), 2.30 (2H, 11.3 Hz); LCMS: (6 min method) m/z 265 [M+H]$^+$, $R_T$ 0.65 min.

4-Benzyl-morpholine-2-carboxylic acid methoxy-methyl-amide (2b)

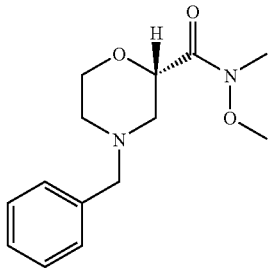

Compound 2 may be separated into its enantiomers by chiral HPLC under the following conditions: Daicel Chiralpak OJ 20 μm; 25 cm; n-heptane/isopropanol 80:20 v:v; 0.4 mL/min; detection at 220 nm. Alternatively, compound 2b may be synthesized substantially as described above for compound 2 using compound 1b in place of compound 1.

2-Phenyl-5-fluoro benzyl bromide

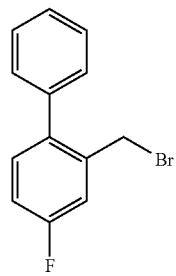

The title compound is prepared in 5 steps from commercially available (Aldrich) 5-fluorosalicylic acid following literature procedures (JACS, 2000, 122, 4020-4028). MW 265.13; $C_{13}H_{10}BrF$; $^1$H NMR (CDCl$_3$): 7.48-7.38 (5H, m), 7.26-7.19 (1H, m), 7.05 (1H, td, 8.3 Hz, 2.8 Hz), 4.39 (2H, s); $^{19}$F NMR (CDCl$_3$): -114.72.

(5-Fluoro-2-methoxy-phenyl)-methanol

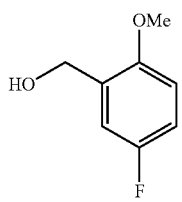

To a solution of 2-methoxy-5-fluorobenzaldehyde (11.093 g, 1 eq, available from Aldrich Chemical Company) in methanol at −10° C. under nitrogen atmosphere is added NaBH$_4$ (7.515 g, 2.7 equiv.) portionwise. The solution is allowed to warm to room temperature and after 30 minutes the reaction solvent is removed under reduced pressure and replaced with dichloromethane. This solution is poured onto ice water and further extracted with dichloromethane. The organic fractions are collected and dried (MgSO$_4$) and the solvent removed under reduced pressure to give the title compound as an oil (9.794 g, 87%). MW 156.16; $C_8H_9FO_2$; $^1$H NMR (CDCl$_3$): 2.58 (m, 1H), 3.81 (s, 3H), 4.63 (d, 2H, 6.3 Hz), 6.78 (dd, 1H, 8.9 Hz and 4.3 Hz), 6.94 (td, 1H, 8.5 Hz and 3.1 Hz), 7.04 (dd, 1H, 8.7 Hz and 3.1 Hz).

5-fluoro-2-methoxybenzyl chloride

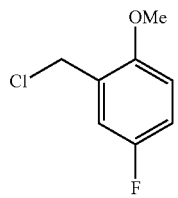

Neat (5-Fluoro-2-methoxy-phenyl)-methanol (19.587 g, 1 equiv.) is added to neat $SOCl_2$ (42.2 mL, 4.6 equiv.) at −78° C. under a nitrogen atmosphere and the solution is then allowed to warm to room temperature and stirred until evolution of gas ceases. An equivalent volume of anhydrous toluene is added to the flask and the solution heated to 60° C. On cooling, the reaction solution is poured onto ice water. The toluene layer is separated and dried ($MgSO_4$) and the solvent removed under reduced pressure. The crude material is sublimed (60-80° C./0.05 mBarr) to give the title compound as a white solid (13.40 g, 61%). MW 174.60; $C_8H_8ClFO$; $^1H$ NMR ($CDCl_3$): 3.87 (s, 3H), 4.60 (s, 2H), 6.79-7.20 (m, 3H).

2-methoxy-5-fluorobenzyl magnesium chloride

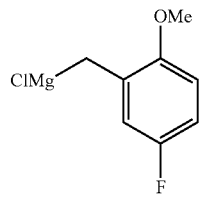

Magnesium turnings (21.6 g, 0.888 mole, 2 eq.) and diethyl ether (300 mL) are loaded in a reactor under $N_2$. A solution of 5-fluoro-2-methoxybenzyl chloride (116 g, 0.664 mol, 1.5 eq.) in diethyl ether (200 mL) is loaded in an addition funnel. Iodine crystals and a small amount of the 5-fluoro-2-methoxybenzyl chloride solution are added and the reaction mixture is stirred to initiate the reaction. The remainder of the 5-fluoro-2 methoxybenzyl chloride solution is then added drop-wise maintaining the temperature of the reaction mixture below 28° C. The mixture is stirred for another 5 minutes at 19° C. and after completion of the addition a white suspension is formed.

1-[4-(Phenylmethyl)morpholin-2-yl]ethan-1-one (3)

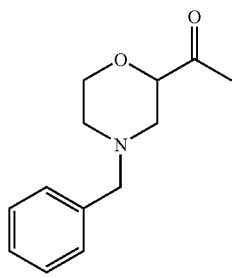

Compound 3 is obtained from 2 (0.730 g, 2.8 mmol) and commercially available (Aldrich) methyl magnesium bromide (1M solution in THF, 3 mL, 3 mmol, 1.1 eq) in anhydrous THF (25 mL) following General Procedure 1 after purification by automated column chromatography (eluent EtOAc/n-heptane 14/86-100/0 [v/v]) (0.3 g, 49%). MW 235.33; $C_{14}H_{21}NO_2$. LCMS (6 minute method) m/z 220.1 $[M+H]^+$, $R_T$ 1.55 min.

1-[4-(Phenylmethyl)morpholin-2-yl]propan-1-one (4)

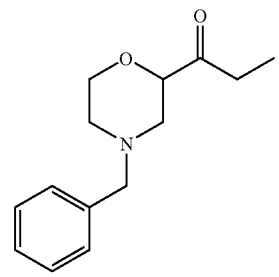

Compound 4 is obtained from 2 (0.70 g, 2.65 mmol) and commercially available (Aldrich) ethyl magnesium bromide (2.65 mL, 7.94 mmol, 3 eq) in anhydrous THF (25 mL) following General Procedure 1 as a yellow oil (583 mg, 89%). MW 249.36; $C_{15}H_{23}NO_2$. LCMS (6 minute method) m/z 234.4 $[M+H]^+$, $R_T$ 1.78 min.

2-Methyl-1-[4-(phenylmethyl)morpholin-2-yl]propan-1-one (5)

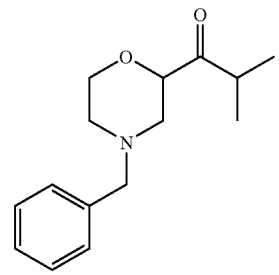

Compound 5 is obtained from 2 (3.018 g, 11.4 mmol) and commercially available (Aldrich) isopropyl magnesium chloride (2M solution in THF, 17.1 mL, 34.3 mmol, 3 eq) in THF (100 mL), following General Procedure 1 as a yellow oil (2.68 g, 89%); MW 263.38; $C_{16}H_{25}NO_2$; LCMS (6 minute method): m/z 248.2 $[M+H]^+$, $R_T$ 2.41 mm.

3-Methyl-1-[4-phenylmethyl)morpholin-2-yl]butan-1-one (6)

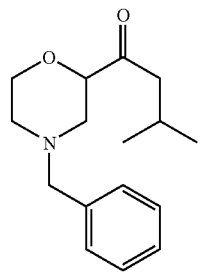

Compound 6 is prepared from 2 (10 g, 37 mmol) in anhydrous tetrahydrofuran (50 mL) and commercially available (Aldrich) isobutyl magnesium bromide (2M solution in diethyl ether, 56 mmol, 28 mL, 1.5 eq) following General Procedure 1. After stirring for 1 hour the reaction is quenched by addition of aqueous hydrochloric acid (150 mL). THF is removed in vacuo and diethyl ether is added after pH adjustment by addition of a saturated sodium bicarbonate solution. The organic phases are combined, dried over magnesium sulphate and the solvent is removed in vacuo. 6 is isolated in 80% purity (8.7 g, 67% with respect to pure product). MW 261.37; $C_{16}H_{23}NO_2$; LCMS: (6 min method) m/z 262.2 $[M+H]^+$, $R_T$ 2.753 min.

Cyclopentyl[4-phenylmethyl)morpholin-2-yl]methanone (7)

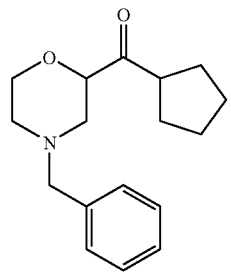

Compound 7 is prepared from 2 (3.36 g, 12.7 mmol) in anhydrous tetrahydrofuran (120 mL) and commercially available (Aldrich) cyclopentyl magnesium bromide (2M solution in diethyl ether, 19.1 mL, 38.2 mmol, 3 eq) following General Procedure 1 in quantitative yield as yellow oil. MW 273.38; $C_{17}H_{23}NO_2$; LCMS (6 min method) m/z 274 $[M+H]^+$, $R_T$ 2.24 min.

[4-(Phenylmethyl)morpholin-2-yl](tetrahydro-2H-pyran-4-yl)methanone (8)

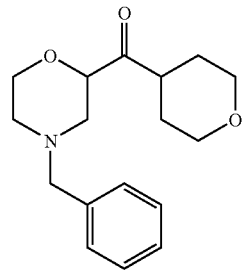

Compound 8 is obtained from 2 (2.84 g, 10.74 mmol) in anhydrous tetrahydrofuran (30 mL) and 4-tetrahydropyranyl magnesium chloride (Chem. Ber. 98, 1965, 3757) (2M solution in tetrahydrofuran, 6.5 mL, 13 mmol, 1.2 eq) following General Procedure 1. After 30 minutes further 4-tetrahydropyranyl magnesium chloride is added (2M solution in diethyl ether, 6.5 mL, 13 mmol, 1 eq.). After stirring for 2 hours the reaction mixture is quenched by addition of ammonium chloride solution (30 mL) and ethyl acetate (30 mL). The aqueous layer is re-extracted with ethylacetate (30 mL) and the organic phases are combined, dried over magnesium sulphate and the solvents are removed in vacuo. The resulting residue is purified by ion exchange chromatography to give 8 as a yellow oil (2.98 g, 96%). MW 289.38; $C_{17}H_{23}NO_3$; LCMS (6 min method) m/z 290 $[M+H]^+$, $R_T$ 2.20 min.

Alternatively compound 8 may be prepared as follows:

a) Neutralization of 92

92 (97 g) is suspended in toluene (485 mL) under mechanical stirring and sodium carbonate (3.68 N, 97 mL, 1.2 equiv) is added. Then, the mixture is diluted with water (194 mL) and stirred for 45 mins at room temperature. Then, the biphasic mixture is filtered on Hyflo Super Cel® and transferred to a separatory funnel. The aqueous layer is discarded and the organic layer (594.3 g) is concentrated under reduced pressure at 40° C. to a mass of 348 g. Toluene is added (150 mL) and the organic layer is concentrated under the same conditions to a mass of 347 g. The free base of compound 92 as a toluene solution is then diluted with anhydrous THF (300 g) and the solution is ready to be added to the Grignard reagent.

b) Formation of the Grignard Reagent

An inerted 3 L 3-necked flask is charged with THF (50 mL) and magnesium turnings (9 g, 0.370 mol, 1.25 equiv.). The mixture is heated to Tmass=60° C. and iodine (0.150 g) and 4-chlorotetrahydropyran (1 mL) are added. Initiation is observed within 5 minutes. Then, the mixture is heated to Tmass=63-68° C. and addition of remaining 4-chlorotetrahydropyran (39.19 mL diluted with 188 mL of THF) is performed over 1 hour keeping T mass constant at about 68° C. After 40 minutes of post-agitation, the reaction mixture is allowed to cool to room temperature.

C) Grignard Reaction

The toluene/THF solution of neutralized 92 is added to the Grignard reagent at 20-25° C. over 45 min. The mixture is post-agitated at room temperature for 1 h. Then, the reaction mixture is quenched by addition at 0-5° C. to an acetic acid/$H_2O$ mixture (44.3 mL acetic acid and 245 mL $H_2O$). The aqueous layer is separated and discarded and the organic layer is washed with $H_2O$ (60 mL). The aqueous layer is separated and discarded and the organic layer is washed with 2N NaOH (100 mL). The aqueous layer is separated and discarded and the organic layer is concentrated under reduced pressure at 40° C. to 230 g. The residue is taken up with IPA (1 L) and concentrated as described above to yield 230 g of 8 as the free base.

[4-(Phenylmethyl)morpholin-2-yl](tetrahydro-2H-pyran-4-yl)methanone (8b)

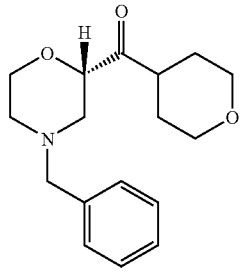

An inerted 6 L reactor is charged with THF (242.5 mL), magnesium (54.47 g, 2240 mmol) and 5% of the total amount of 4-chlorotetrahydropyran (12.28 mL, 112 mmol). Then, a small amount of methyl iodide (0.5 mL) and one iodine crystal is added. The reaction mixture is stirred and heated up to 64-66° C. After initiation, the remaining 4-chlorotetrahydropyran (233.22 mL, 2127 mmol) diluted in THF (890 mL) is slowly added over 135 mins. The mixture is heated up for 30 additional minutes before being cooled to 0° C. Then, the Weinreb amide 2b (370 g, 1400 mmol) diluted in THF (2777 mL) is added over 180 mins between 0-4° C. and the mixture is stirred for a further 60 mins. Then, acetic acid (48 mL, 0.83 mmol) is added to the mixture followed by a 55/45:v/v:saturated $NH_4Cl/H_2O$ mixture (2590 mL) keeping the temperature below 9° C. The organic layer is washed with a 60/40:v/v:saturated $NH_4Cl/H_2O$ mixture (500 mL) and, after separation, toluene (1800 mL) and water (1800 mL) is added to the organic solution. Then after extraction, water (1100 mL) is added to the toluene mixture which is basified with 3.68 M $Na_2CO_3$aq (148 mL). The organic layer is dried over $MgSO_4$, filtered and concentrated under reduced pressure to dryness to yield compound 8b as the free base (400.8 g, 98.6% yield).

Alternatively compound 8b may be prepared as follows:

R-(−)-Mandelic acid (1.65 g, 10.8 mmol) is added to a solution of 8 (3.15 g, 10.8 mmol) in isopropanol (20 mL). After 2 min of post-agitation, an homogenous solution is obtained at room temperature. Crystallization begins after 5 min of post-agitation to form an easily stirable suspension. This suspension is post-stirred for 21 hours at room temperature. The solid is filtered and washed with isopropanol (2 mL). The white crystals are dried under vacuum at 40° C. over 5 hours to give 1.8 g of 8b R-mandelate with 37.5% yield and 99.2% ee. 0.5N of $K_2CO_3$ (2.4 mL, 1.2 mmol) is added dropwise to a stirred suspension of 8b R-mandelate (500 mg, 1.13 mmol) in toluene (5 mL). A biphasic solution is obtained. The free base 8b is entirely present in the organic layer, which is separated, concentrated on a rotovap and dried under vacuum at 40° C. affording 8b as an oil with 98% yield.

5,5,5-Trifluoro-1-[4-(phenylmethyl)morpholin-2-yl]butan-1-one (9)

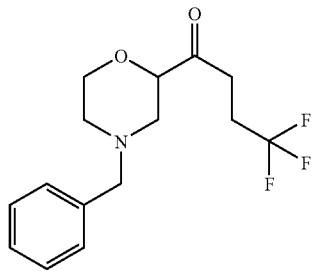

Compound 9 is obtained from 2 (1.38 g, 5.23 mmol) and 3,3,3-trifluoropropyl magnesium bromide (20.9 mL, 10.50 mmol, 2 eq) in dry THF (45 mL) following General procedure 1. 3,3,3-Trifluoropropyl magnesium bromide is obtained from commercially available (Aldrich) 3,3,3-trifluoropropyl bromide following General Procedure 5. Purification by ion exchange chromatography gives 9 as an oil (1.24 g, 78.7%). MW 301.31; $C_{15}H_{18}F_3NO_2$; LCMS (6 minute method): m/z 302.4 $[M+H]^+$, $R_T$ 2.66 min.

5,5,5-Trifluoro-1-[4-(phenylmethyl)morpholin-2-yl]pentan-1-one (10)

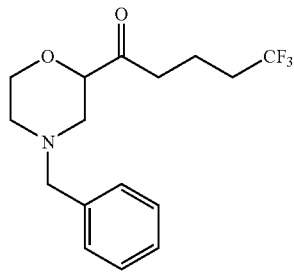

Compound 10 is prepared from a solution of 2 (0.717 g, 2.71 mmol) in anhydrous tetrahydrofuran (20 mL) and 4,4,4-trifluorobutyl magnesium bromide (0.5M solution in diethyl ether, 6.5 mL, 3.25 mmol, 1.2 eq). 4,4,4-Trifluorobutyl magnesium bromide is obtained from commercially available (Aldrich) 4,4,4-trifluorobutyl bromide following General Procedure 5. After 30 minutes another 0.3 eq of 4,4,4-trifluorobutyl magnesium bromide are added (0.5M solution in diethyl ether, 2.5 mL). After stirring for 2 hours the solvents are removed in vacuo and water (20 mL) and ethyl acetate (30 mL) are added to the residue. The organic phase is washed with brine, dried over magnesium sulphate and the solvent is removed in vacuo to give 10 as clear oil (0.985 g). 10 is taken onto the next step without further purification. MW 315.34; $C_{16}H_{20}NO_2F_3$; LCMS: (6 min method) m/z 316 $[M+H]^+$, $R_T$ 2.9 min.

4-Benzylmorpholin-3-one

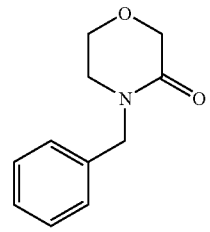

A solution of N-benzyl-N-(2-hydroxyethyl)chloroacetamide (627.7 g, 2.76 mol) in tert-butanol (0.9 L) is stirred under nitrogen while warming to 25-30° C. Potassium tert-butoxide (2.897 L of a 1M solution in tert-butanol, 2.90 mol, 1.05 eq) is added over 2 hours. The reaction mixture is then stirred at room temperature for 90 minutes. Ice-cold water (6 L) is added and the resultant cloudy solution extracted with ethyl acetate. The combined organic layers are washed with brine, dried over magnesium sulphate and evaporated in vacuo to give a light brown oil (441 g, 84%), which is used in the next stage without further purification; MW 191.23; $C_{11}H_{13}NO_2$; $^1$H NMR (CDCl$_3$): 7.29-7.40 (5H, m), 4.67 (2H, s), 4.28 (2H, s), 3.87 (2H, t, 5 Hz), 3.31 (2H, t, 5 Hz); LCMS: (12 min method) m/z 192 $[M+H]^+R_T$ 1.00 min.

45

4-Benzyl-2-(cyclopropyl-hydroxy-methyl)-morpholin-3-one (75)

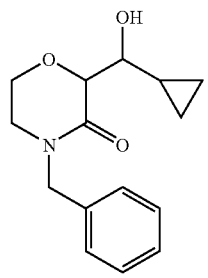

To a solution of 4-benzyl-morpholin-3-one (9.5 g, 50 mmol) in THF (200 mL) is added lithium diisopropylamide (2M solution in THF, 27 mL, 54 mmol, 1.1 eq) dropwise over 20 minutes at −78° C. followed by slow addition of cyclopropyl methylaldehyde (3.85 mL, 55 mmol, 1.1 eq). After stirring at −78° C. for one hour the reaction mixture is allowed to warm to room temperature and stirred for another 6 hours. The reaction is quenched by addition of EtOAc and brine. The aqueous layer is extracted with EtOAc, the combined organic layers are dried over magnesium sulphate and reduced in vacuo. Purification using automated column chromatography (DCM/MeOH, 100/0 to 85/15 [v/v]) gives 75 in 70% purity with 4-benzyl-morpholin-3-one as the major impurity. This product is directly used in the next step. MW 261.32; $C_{15}H_{19}NO_3$; LCMS (6 min method) m/z 261.32 [M+H]$^+$, $R_T$ 2.23

(4-Benzyl-morpholin-2-yl)-cyclopropyl-methanol (76)

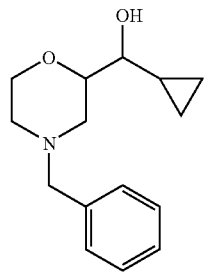

Borane-THF complex (1M solution in THF, 30 mL, 30 mmol, 4.1 eq) is added slowly to a solution of 75 (1.9 g, 7.3 mmol) in THF (100 mL). The reaction is heated to 60° C. After 24 hours MeOH and hydrochloric acid (2M, excess) are added and the resulting mixture heated for one hour at the same temperature. After careful addition of saturated NaHCO$_3$ solution and EtOAc the aqueous layer is extracted with EtOAc. The combined organic layers are washed with brine, dried over magnesium sulphate and the solvent is removed in vacuo. Purification by ion exchange chromatography gives 76 (1.1 g, 61%). MW 247.34; $C_{15}H_{21}NO_2$; LCMS (6 min method) m/z 248 [M+H]$^+$, $R_T$ 2.48 min

46

Cyclopropyl[4-(phenylmethyl)morpholin-2-yl]methanone (77)

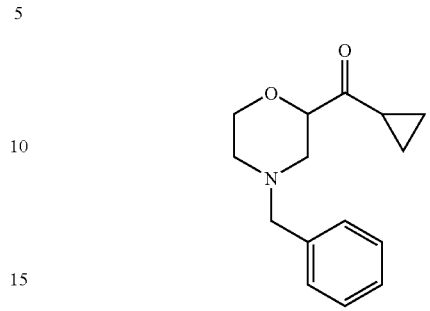

A solution of dimethylsulphoxide (0.69 mL, 9.7 mmol, 2.2 eq) in DCM (4.5 mL) is slowly added to a solution of oxalyl chloride (2.43 mL, 4.85 mmol, 1.1 eq) in DCM (2.5 mL) followed by a solution of 76 (1.09 g, 4.41 mmol) in DCM (0.7 mL) under nitrogen at −60° C. After stirring for 15 minutes, triethylamine (3.14 mL, 22.1 mmol, 5 eq) is added and stirring continues for 15 minutes. After addition of water, the layers are separated.

The aqueous layer is washed with DCM. The combined organic layers are washed with brine, dried over magnesium sulphate and the solvent is removed in vacuo. Purification using automated column chromatography (EtOAc/n-hexane, 20/80 to −50/50 [v/v]) gives 77 as a yellow oil (0.69 g, 64%). MW 245.32; $C_{15}H_{19}NO_2$; LCMS (6 min method) m/z 246.3 [M+H]$^+$, $R_T$ 1.095 min.

1-(4-Benzyl-morpholin-2-yl)-pentan-1-one (82)

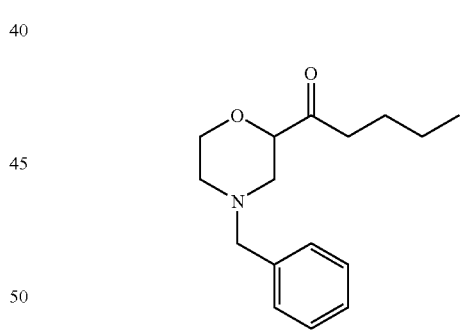

Compound 82 is prepared from 2 (0.87 g, 3.28 mmol) in anhydrous tetrahydrofuran (30 mL) and commercially available (Aldrich) n-butyl magnesium bromide (2M solution in THF, 5 mmol, 2.5 mL, 1.5 eq) following General Procedure 1. After stirring for 1 hour further n-butyl magnesium bromide (2M solution in THF, 1.6 mmol, 0.8 mL) is added and stirring continued for 30 minutes. The reaction is quenched by addition of ammonium chloride solution (30 mL) followed by EtOAc. The organic phases are combined, dried over magnesium sulphate and the solvent is removed in vacuo to give 82 (0.82 g, 96%). MW 261.37; $C_{16}H_{23}NO_2$; LCMS (6 minute method): m/z 262.4 [M+H]$^+$, $R_T$ 2.34 mm.

Example 1

Preparation of 1-[1,1'-biphenyl]-2-yl-2-morpholin-2-ylpropan-2-ol hydrochloride (12)

1-[1,1'-Biphenyl]-2-yl-2-[4-(phenylmethyl)morpholin-2-yl]propan-2-ol (11)

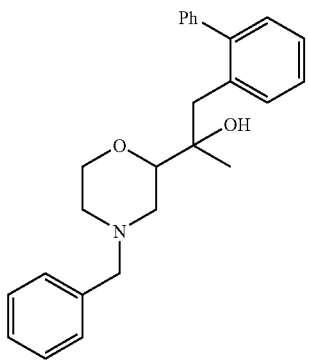

Compound 11 is prepared from 2-phenylbenzyl magnesium bromide (0.25M solution in diethyl ether, 5.5 mL, 1.38 mmol) and 3 (275 mg, 1.25 mmol) in anhydrous THF (7 mL) following General Procedure 2. 2-Phenylbenzyl magnesium bromide is obtained from commercially available (Aldrich) 2-phenylbenzyl bromide following General Procedure 5. Further equivalents of 2-phenylbenzyl magnesium bromide (10 mL, 2.5 mmol) are added before quenching the reaction with ice water (7 mL). 11 is obtained as an oil in 75% purity after ion exchange (5 g column) chromatography and automated column chromatography (EtOAc/n-heptane 0/100 to 50/50 [v/v]) and taken onto the next step without further purification (0.23 g isolated material). MW 387.53; $C_{26}H_{29}NO_2$; LCMS (6 minute method): m/z 388.2 $[M+H]^+$, $R_T$ 3.37 min.

1-[1,1'-Biphenyl]-2-yl-2-morpholin-2-ylpropan-2-ol hydrochloride (12)

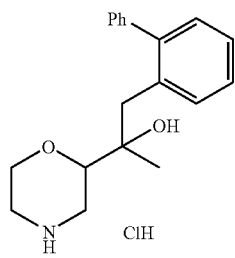

12 is obtained from 11 (204 mg, 0.53 mmol), α-chloroethyl chloroformate (0.23 mL, 2.11 mmol) and polymer-supported Hünig's base (296 mg, 1.05 mmol) in DCM (5 mL) following General Procedure 3. Purification using ion exchange chromatography, followed by preparative LCMS and conversion into the hydrochloride salt following General Procedure 4 gives 12 as a foam (102 mg, 65%). MW 297.36; $C_{19}H_{23}NO_2$·HCl; $^1$H NMR (CD$_3$OD) δ 7.15-7.39 (8H, m), 7.07-7.11 (1H, m), 3.97 (1H, dd, 3.0 Hz, 13.0 Hz), 3.56-3.65 (1H, m), 3.20-3.25 (1H, m), 3.08 (2H, t, 12.5 Hz), 2.82-2.99 (4H, m), 0.60 (3H, s); LCMS (12 minute method): m/z 298.2 $[M-HCl+H]^+$, $R_T$ 4.38 min.

Example 2

Preparation of 1-[5-fluoro-2-(methyloxy)phenyl]-2-morpholin-2-ylbutan-2-ol hydrochloride (14)

1-[5-Fluoro-2-(methyloxy)phenyl]-2-[4-(phenylmethyl)morpholin-2-yl]butan-2-ol (13)

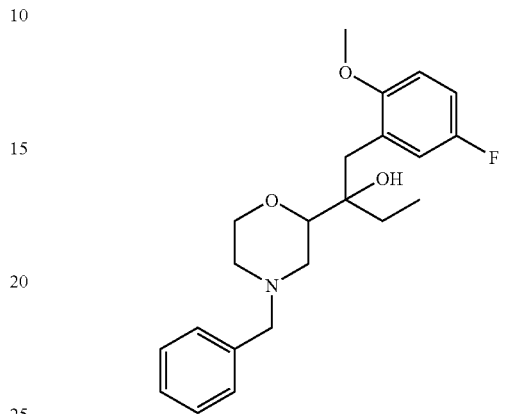

Compound 13 is obtained from 4 (583 mg, 2.5 mmol) and 2-methoxy-5-fluorobenzyl magnesium bromide (5.5 mL, 2.75 mmol, 1.1 eq) in anhydrous THF (15 mL) following General Procedure 2. Further equivalents of 2-methoxy-5-fluorobenzyl magnesium bromide (2M solution in diethyl ether, 10 mL, 5.0 mmol) are added after 30 min and the mixture is warned to room temperature and left to stir over night. After purification by ion exchange chromatography 13 is obtained as a yellow oil in 67% purity (702 mg). The compound is taken over to the next step without further purification. MW 373.47; $C_{22}H_{28}FNO_3$; LCMS (6 minute method) m/z 374.2 $[M+H]^+$, $R_T$ 3.17 min.

1-[5-Fluoro-2-(methyloxy)phenyl]-2-morpholin-2-ylbutan-2-ol hydrochloride (14)

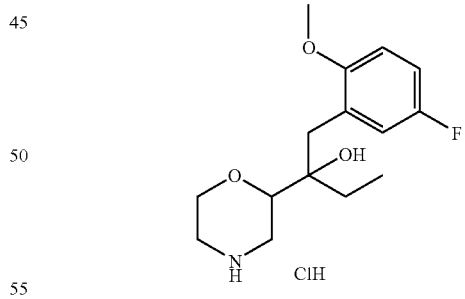

14 is obtained from 13 (717 mg, 1.92 mmol), α-chloroethyl chloroformate (0.83 mL, 3.84 mmol, 4 eq) and polymer-supported Hünig's base (1.08 g, 3.84 mmol, 2 eq) in DCM (17 mL) following General Procedure 3. Purification by ion exchange chromatography followed by preparative LCMS and conversion into the hydrochloride salt following General Procedure 4 gives 14 as a solid (185 mg, 30%). MW 319.81; $C_{15}H_{22}FNO_3$·HCl; $^1$H NMR (CD$_3$OD) δ 6.94 (1H, dt, 1.5 Hz, 9 Hz), 6.81-6.84 (2H, m), 4.07 (1H, dd, 3.5, 13 Hz), 3.67-3.76 (4H, m), 3.56 (1H, dd, 2.5 Hz, 11 Hz), 3.33 (1H, m), 3.14-3.25 (1H, m), 3.00-3.08 (2H, m), 2.84 (2H, 14 Hz), 1.37-1.51 (1H, m), 1.05-1.19 (1H, m), 0.82 (3H, t, 7.5 Hz); LCMS (12 minute method): m/z 284.1 [M−HCl+H]+, $R_T$ 3.76 min.

Example 3

Preparation of 2-morpholin-2-yl-1-{2-[(trifluoromethyl)oxy]phenyl}butan-2-ol hydrochloride (16)

2-[4-(Phenylmethyl)morpholin-2-yl]-1-{2-[(trifluoromethyl)oxy]phenyl}butan-2-ol (15)

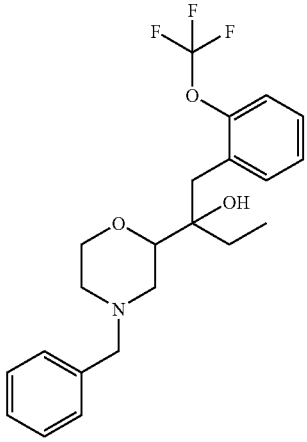

Compound 15 is obtained from 4 (1.1 g, 4.71 mmol) and commercially available (Fluorochem) 2-trifluoromethoxy benzyl magnesium bromide (10.4 mL 1, 5.19 mmol, 1.1 eq) in anhydrous THF (31 mL) following General Procedure 2. After 30 minutes further equivalents of 2-trifluoromethoxy benzyl magnesium bromide are added (0.5M solution in diethyl ether, 4.71 mL, 2.36 mmol). Purification by ion exchange chromatography gives 15 as an oil (1.88 g, 98%). MW 409.45; $C_{22}H_{26}F_3NO_3$; LCMS (6 minute method): m/z 410.4 [M+H]+, $R_T$ 3.28 min.

2-Morpholin-2-yl-1-{2-[(trifluoromethyl)oxy]phenyl}butan-2-ol hydrochloride (16)

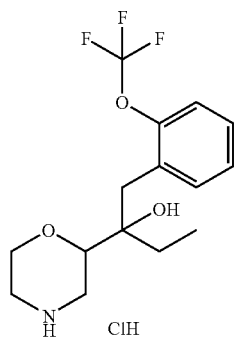

16 is obtained from 15 (1.88 g, 4.59 mmol), α-chloroethyl chloroformate (1.98 mL L, 18.4 mmol) and polymer-supported Hünig's base (2.58 g, 9.18 mmol) in DCM (40 mL) following General Procedure 3. Purification using ion exchange chromatography followed by automated column chromatography (eluent, MeOH/DCM 0/100 to 20/80 [v/v]) and conversion to the hydrochloride salt following General Procedure 4 gives 16 (258.5 mg, 17%) as a white solid. MW 319.33; $C_{15}H_{20}F_3NO_3$.HCl; 1H NMR (CD3OD)-δ 7.53 (1H, dd, 2 Hz, 7.5 Hz), 7.27-7.38 (3H, m), 4.20 (1H, dd, 3.5 Hz, 13 Hz), 3.85 (1H, td, 3 Hz, 13 Hz), 3.70 (1H, dd, 2 Hz, 11 Hz), 3.44 (1H, d, 13 Hz), 3.27-3.34 (1H, m), 3.12-3.22 (2H, m), 3.07 (1H, d, 14 Hz), 2.96 (1H, d, 14 Hz), 1.55 (1H, sextet, 7.5 Hz), 1.26 (1H, sextet, 7.5 Hz), 0.93 (3H, t, 7.5 Hz). LCMS (12 minute method): m/z 320.4 [M−HCl+H]+, $R_T$ 2.77 min.

Example 4

Preparation of 1-[1,1'-biphenyl]-2-yl-2-morpholin-2-ylbutan-2-ol hydrochloride (18)

1-[1,1'-Biphenyl]-2-yl-2-[4-phenylmethyl)morpholin-2-ylbutan-2-ol (17)

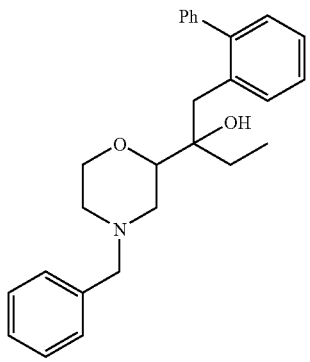

Compound 17 is obtained from 3 (601 mg, 2.58 mmol) and 2-phenylbenzyl magnesium bromide (0.25M solution in diethyl ether, 11.5 mL, 2.84 mmol) in anhydrous THF (15 mL) following General Procedure 2. 2-Phenylbenzyl magnesium bromide is prepared from commercially available (Aldrich) 2-phenylbenzyl bromide following General Procedure 5. Further equivalents of 2-phenylbenzyl magnesium bromide (10.32 mL, 2.58 mmol) are added. Purification by ion exchange chromatography followed by automated column chromatography (eluent, EtOAc/n-heptane 0/100 to 50/50 [v/v]) gives 17 (705 mg, 68%) as a colourless oil in 91% purity which is directly used in the next step. MW 401.55; $C_{27}H_{31}NO_2$; LCMS (6 minute method): m/z 402.2 [M+H]+, $R_T$ 3.56 min 1-[1,1'-Biphenyl]-2-yl-2-morpholin-2-ylbutan-2-ol hydrochloride (18)

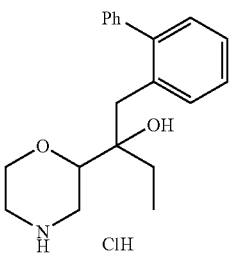

18 is obtained from 17 (705 mg, 1.76 mmol), α-chloroethyl chloroformate (0.76 mL, 7.02 mmol) and polymer-supported Hünig's base (988 g, 3.52 mmol) in DCM (15 mL) following General Procedure 3. Purification by ion exchange chromatography followed by automated column chromatography (eluent, MeOH/DCM 5/95 to 20/80 [v/v]) and conversion into the hydrochloride salt following General Procedure 4 gives 18 (0.37 g, 62%) as a yellow foam. MW 347.82; $C_{20}H_{25}NO_2 \cdot HCl$; $^1H$ NMR ($CD_3OD$) δ 7.43-7.46 (1H, m), 7.29-7.34 (3H, m), 7.14-7.25 (5H, m), 7.06-7.11 (1H, m), 3.94 (1H, dd, 3.5 Hz, 13 Hz), 3.55-3.64 (1H, m), 3.37 (1H, dd, 1.5 Hz, 11 Hz), 3.09 (2H, d, 12.5 Hz), 2.80-2.99 (4H, m), 1.11-1.23 (1H, m), 0.91 (1H, m), 0.38 (3H, t, 7.5 Hz). LCMS (12 minute method): m/z 312.1 [M−HCl+H]$^+$, $R_T$ 4.67 min.

Example 5

Preparation of 1-[5-fluoro-2-(methyloxy)phenyl]-3-methyl-2-morpholin-2-ylbutan-2-ol hydrochloride (20)

1-[5-Fluoro-2-(methyloxy)phenyl]-3-methyl-2-[4-(phenylmethyl)morpholin-2-yl]butan-2-ol (19)

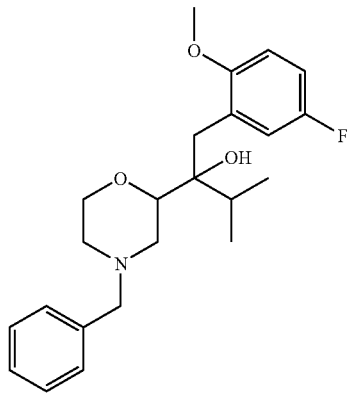

Compound 19 is obtained from 5 (0.7 g, 2.83 mmol) and 2-methoxy-5-fluoro-benzyl magnesium bromide (6.2 mL, 3.11 mmol, 1.1 eq) in anhydrous THF (15 mL 1) following General Procedure 2. Further equivalents of 2-methoxy-5-fluoro-benzyl magnesium bromide (8.49 mL, 4.25 mmol) are added and mixture is warmed to room temperature and left stirring overnight. Purification using automated column chromatography (eluent, n-heptane/EtOAc 100/0 to 75/25 [v/v]) gives 19 (0.53 g, 48%). MW 387.5; $C_{23}H_{30}FNO_3$; LCMS (6 minute method): m/z 388.2 [M+H]$^+$, $R_T$ 3.21 min.

1-[5-fluoro-2-(methyloxy)phenyl]-3-methyl-2-morpholin-2-ylbutan-2-ol hydrochloride (20)

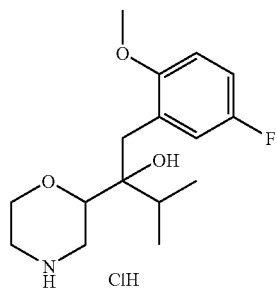

20 is obtained from 19 (523 mg, 1.35 mmol), α-chloroethyl chloroformate (0.58 mL, 5.40 mmol, 4 eq) and PS-DIEA (0.76 g, 2.70 mmol, 2 eq) in DCM (10 mL) following General Procedure 4. Purification by ion exchange chromatography and conversion to the hydrochloride salt following General Procedure 4 gives 20 as an off-white solid (0.26 g, 58%). MW 333.83; $C_{16}H_{24}FNO_3 \cdot HCl$; $^1H$ NMR ($CD_3OD$) δ 7.10 (1H, d, 9.5 Hz), 6.94 (2H, d, 6 Hz), 4.07 (1H, dd, 3.5 Hz, 13 Hz), 3.71-3.88 (5H, m), 3.21-3.47 (2H, m), 2.99-3.11 (4H, m), 1.8 (1H, septet, 7 Hz), 1.04 (3H, d, 7 Hz), 0.94 (3H, d, 7.0 Hz); LCMS (12 minute method): m/z 298 [M−HCl+H]+, $R_T$ 4.29 min.

Example 6

Preparation of 3-methyl-1-[2-methyloxy)phenyl]-2-morpholin-2-ylbutan-2-ol hydrochloride (22)

2-(4-Benzyl-morpholin-2-yl)-1-(2-methoxy-phenyl)-3-methyl-butan-2-ol (21)

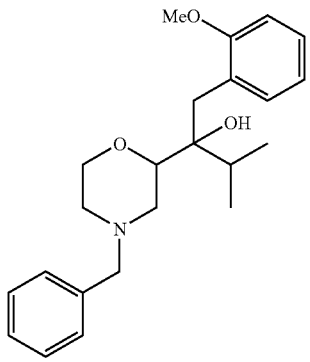

Compound 21 is obtained from 5 (1.5 g, 6.06 mmol) and 2-methoxy benzyl magnesium bromide (available from Rieke-Metals) (0.25M solution in THF, 33.9 mL, 8.49 mmol) in anhydrous THF (30 mL) following General Procedure 1. Purification by column chromatography (eluent, EtOAc/n-heptane 0/100 to 40/60 [v/v]) gives 21 as colourless oil (1.45 g, 84%). MW 369.51; $C_{23}H_{31}NO_3 \cdot HCl$; LCMS (6 minute method): m/z 370.2 [M−HCl+H]$^+$, $R_T$ 2.77 min.

3-Methyl-1-[2-methyloxy)phenyl]-2-morpholin-2-ylbutan-2-ol hydrochloride (22)

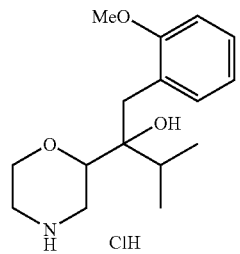

22 is obtained from 21 (1.24 g, 3.37 mmol), α-chloroethyl chloroformate (3.63 mL, 33.7 mmol) and polymer-supported Hünig's base (4.72 g, 16.8 mmol) in DCM (45 mL) following General Procedure 3. Purification using ion exchange chromatography followed by chiral preparative HPLC (n-Heptane EtOH:DEA 85:15:0.2 gradient, chiralcel-OD) gives two enantiomers the first eluting enantiomer ($R_T$ 9.5 min), and the second eluting enantiomer ($R_T$ 11.41 min). The two enantiomers are converted to their respective hydrochloride salts 22a (146 mg) and 22b (138 mg) and obtained as white solids (28% overall combined yield). MW 315.84; $C_{16}H_{25}NO_3 \cdot HCl$; $^1H$ NMR ($CD_3OD$) δ 7.22-7.34 (2H, m), 6.85-6.95 (2H, m), 4.08 (1H, dd, 3.6 Hz, 12.8 Hz), 3.86-3.9 (4H, m), 3.77 (1H, td, 2.45 Hz, 12.4 Hz), 3.22-3.28 (1H, m), 3.24 (1H, d, 12.8 Hz), 2.95-3.11 (4H, m), 1.83 (1H, septet, 6.8 Hz), 1.16 (3H, d, 7.0 Hz), 0.95 (3H, d, 7.0 Hz); LCMS (12 minute method): m/z 280.2 [M−HCl+H]$^+$, $R_T$ 4.05 min.

Example 7

Preparation of 1-[2-(ethyloxy)phenyl]-3-methyl-2-morpholin-2-ylbutan-2-ol hydrochloride (24)

1-[2-(Ethyloxy)phenyl]-3-methyl-2-[4-phenylmethyl)morpholin-2-ylbutan-2-ol (23)

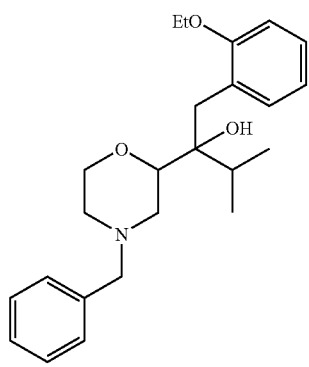

Compound 23 is obtained from 5 (1.5 g, 6.06 mmol) and 2-ethoxybenzyl magnesium chloride (available from Rieke-Metals) (0.25M solution in THF, 34 mL, 8.49 mmol) in anhydrous THF (30 mL) following General Procedure 2. After repeated purification by automated column chromatography (1 eluent MeOH/DCM 0/100 to 10/90 [v/v] followed by EtOAc/DCM 0/100 to 50/50 [v/v]) 23 is obtained as colourless oil (0.8 g, 35%). MW 383.54, $C_{24}H_{33}NO_3$; LCMS (6 minute method): m/z 384.4 [M+H]$^+$, $R_T$ 3.04 min.

1-[2-(Ethyloxy)phenyl]-3-methyl-2-morpholin-2-ylbutan-2-ol hydrochloride (24)

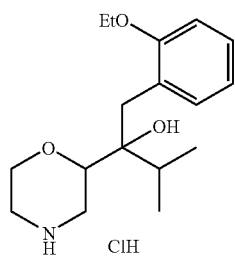

24 is obtained from 23 (766 mg, 2.0 mmol), α-chloroethyl chloroformate (0.86 mL, 8.0 mmol) and polymer-supported Hünig's base (1.12 g, 4.0 mmol) in DCM (30 mL) following General Procedure 3. Purification using ion exchange chromatography followed by automated column chromatography (eluent, MeOH/DCM 0/100 to 20/80 [v/v]) and chiral preparative chromatography (n-Heptane:EtOH:DEA 95:5:0.2 gradient, chiracel AD) gives the first eluting enantiomer ($R_T$ 13.40 min) and the second eluting enantiomer ($R_T$ 15.63 min). After conversion to their respective hydrochloride salts, 24a (85 mg) and 24b (79 mg) are obtained as brown solids (28% combined yield). MW 293.36; $C_{17}H_{27}NO_3 \cdot HCl$; $^1H$ NMR (CD$_3$OD) δ 7.06-7.09 (1H, m), 6.95-7.01 (1H, m), 6.66-6.75 (2H, m), 3.80-3.92 (3H, m), 3.46-3.63 (2H, m), 2.96-3.15 (2H, m), 2.66-2.86 (4H, m), 1.54-1.63 (1H, m), 1.22 (3H, t, 7.0 Hz), 0.82 (3H, d, 7.0 Hz), 0.71 (3H, d, 7.0 Hz); LCMS (12 minute method): m/z 294.2 [M–HCl+H]$^+$, $R_T$ 4.60 min.

Example 8

3-Methyl-2-morpholin-2-yl-1-{2-[(trifluoromethyl)oxy]butan-2-ol hydrochloride (26)

3-Methyl-2-[4-(phenylmethyl)morpholin-2-yl]-1-{2-[(trifluoromethyl)oxy]-phenyl}butan-2-ol (25)

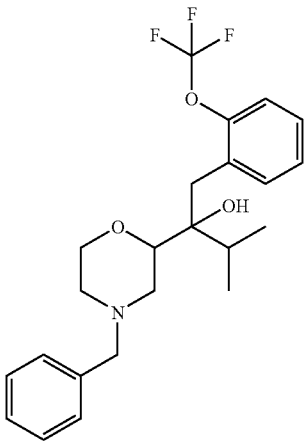

Compound 25 is obtained from 5 (953 mg, 3.85 mmol) and commercially available (Fluorochem) 2-trifluoromethoxy benzyl magnesium bromide (8.48 mL, 4.24 mmol, 1.1 eq) in anhydrous THF (25 mL) following General Procedure 3 and addition of further 2-trifluoromethoxy benzyl magnesium bromide (3.85 mL, 1.93 mmol). Purification by ion exchange chromatography gives 25 as a yellow oil in 86% purity which is used in the next step without further purification (1.53 g of isolated material). MW 423.38; $C_{23}H_{28}F_3NO_3$; LCMS (6 minute method) m/z 424.1 [M+H]$^+$, $R_T$ 3.53 min.

3-Methyl-2-morpholin-2-yl-1-{2-[(trifluoromethyl)oxy]phenyl}butan-2-ol hydrochloride (26)

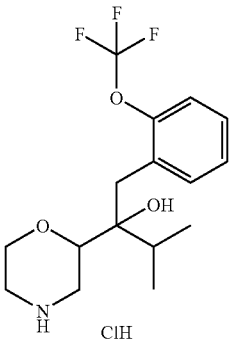

26 is obtained from 25 (1.53 g, 3.61 mmol), α-chloroethyl chloroformate (1.55 mL, 14.5 mmol, 4 equiv.) and polymer-supported Hünig's base (2.03 g, 7.23 mmol, 2 eq) in DCM (30 mL) following General Procedure 3. Purification by ion exchange chromatography, followed by automated column chromatography eluent, MeOH/DCM 0/100 to 20/80 [v/v])

and conversion to its hydrochloride salt following General Procedure 4 gives 26 as a yellow solid (0.4 g, 29%). MW 379.82; $C_{16}H_{22}F_3NO_3 \cdot HCl$; $^1H$ NMR (CD$_3$OD) δ 7.46 (1H, dd, 1.5 Hz, 7.5 Hz), 7.14-7.24 (3H, m), 3.94 (1H, dd, 3.5 Hz, 13 Hz), 3.80 (1H, dd, 2.5 Hz, 11.5 Hz) 3.69 (1H, td, 2.5 Hz, 13 Hz), 3.27 (1H, d, 13 Hz), 3.13 (1H, d, 12.5 Hz), 2.72-3.02 (4H, m), 1.70 (1H, septet, 7 Hz), 0.94 (3H, d, 7 Hz), 0.84 (3H, d, 7.0 Hz). LCMS (12 minute method): m/z 334.4 [M−HCl+H]$^+$, R$_T$ 2.94 min.

Example 9

Preparation of 1-[1,1'-biphenyl]-2-yl-3-methyl-2-morpholin-2-ylbutan-2-ol hydrochloride (28)

1-[1,1'-Biphenyl]-2-yl-3-methyl-2-[4-(phenylmethyl)morpholin-2-ylbutan-2-ol (27)

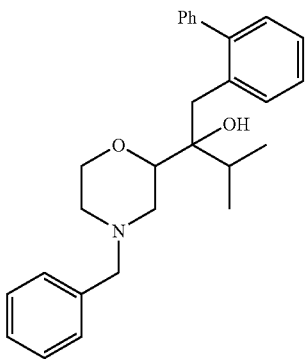

Compound 27 is obtained from 5 (0.7 g, 2.83 mmol) and 2-phenylbenzyl magnesium bromide (12.5 mL, 3.11 mmol) in anhydrous THF (15 mL) following General Procedure 2 and further equivalents of 2-phenylbenzyl magnesium bromide reagent (11.3 mL, 5.66 mmol). 2-Phenylbenzyl magnesium bromide is prepared from commercially available (Aldrich) 2-phenylbenzyl bromide following General Procedure 5. Purification using ion exchange chromatography, followed by automated column chromatography (eluent, EtOAc/n-heptane 0/100 to 20/80 [v/v]) gives 27 as oil (0.46 g, 40%). MW 415.58; $C_{28}H_{33}NO_2$; LCMS (6 minute method): m/z 416.2 [M+H]$^+$, R$_T$ 3.45 min.

1-[1,1'-Biphenyl]-2-yl-3-methyl-2-morpholin-2-ylbutan-2-ol hydrochloride (28)

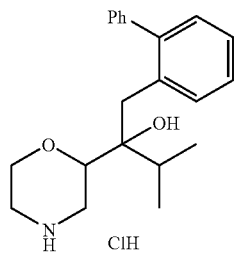

28 is obtained from 27 (405 mg, 0.976 mmol), α-chloroethyl chloroformate (0.42 mL, 3.9 mmol) and polymer-supported Hünig's base (0.55 g, 1.95 mmol) in DCM (7 mL) following General Procedure 3. The crude product is purified using ion exchange chromatography, and then converted to its hydrochloride salt following General Procedure 4 to give 28 as a white solid (0.23 g, 71%). MW 361.91; $C_{21}H_{27}NO_2 \cdot HCl$; $^1H$ NMR (CD$_3$OD) δ 7.61-7.64 (1H, m), 7.19-7.47 (8H, m), 3.95 (1H, dd, 4 Hz, 13 Hz), 3.61-3.71 (2H, m), 3.04-3.19 (4H, m), 2.96 (1H, td, 4 Hz, 12.6 Hz), 2.70 (1H, dd, 13, 11.5 Hz), 1.67 (1H, septet, 7 Hz), 0.75 (3H, d, 7 Hz), 0.63 (3H, d, 7 Hz); LCMS (12 minute method): m/z 326.2 [M−HCl+H]$^+$, R$_T$ 5.02 min.

Example 10

Preparation of 1-(4-Fluoro[1,1'-biphenyl]-2-yl)-3-methyl-2-morpholin-2-ylbutan-2-ol hydrochloride (30)

1-(4-Fluoro[1,1'-biphenyl]-2-yl)-3-methyl-2-[4-(phenylmethyl)morpholin-2-ylbutan-2-ol hydrochloride (29)

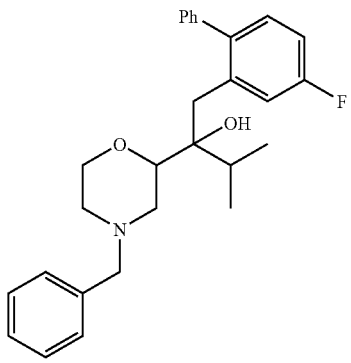

Compound 29 is obtained from 5 (1.13 g, 4.57 mmol) and 2-phenyl-5-fluorobenzyl magnesium bromide (0.5M in THF, 10.5 mL, 5.03 mmol) in anhydrous THF (30 mL) following General Procedure 2 (further 2-phenyl-5-fluorobenzyl magnesium bromide (0.33 eq, 3 mL, 1.51 mmol) is added after 30 min). 2-Phenyl-5-fluorobenzyl magnesium bromide is obtained from 2-phenyl-5-fluorobenzyl bromide following General Procedure 5. Purification by ion exchange chromatography followed by automated column chromatography (eluent, EtOAc/n-heptane 0/100 to 20/80 [v/v]) gives 29 as a yellow oil in 86% purity which is directly used in the next step (1.58 g recovered material). MW 415.58; $C_{28}H_{33}NO_2$; LCMS (6 minute method): m/z 434.5 [M+H]$^+$, R$_T$ 3.71 min.

1-(4-Fluoro[1,1'-biphenyl]-2yl)-3-methyl-2-morpholin-2-ylbutan-2-ol hydrochloride (30)

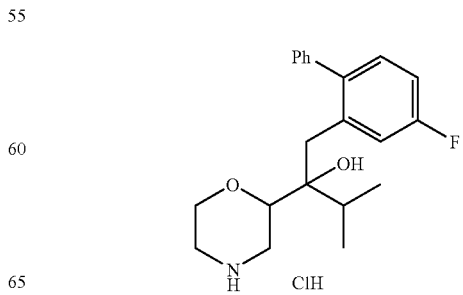

30 is obtained from 29 (1.58 g, 3.63 mmol), α-chloroethyl chloroformate (1.57 mL, 3.63 mmol) and polymer-supported Hünig's base (2.04 g, 7.26 mmol) in DCM (30 mL) following General Procedure 3. The crude product is purified using ion exchange chromatography, automated column chromatography (eluent, MeOH/DCM 0/100 to 20/80 [v/v]), and preparative LCMS. Conversion to the hydrochloride salt following General Procedure 4 gives 30 as a yellow solid (0.3 g, 22%). MW 379.91; $C_{21}H_{26}FNO_2 \cdot HCl$ $^1H$ NMR ($CD_3OD$) δ7.20-7.35 (6H, m), 7.07-7.14 (1H, m), 6.90 (1H, td, 2.5 Hz, 8.5 Hz), 3.83 (1H, d, br, 10 Hz), 3.56 (2H, t, 10 Hz), 3.03-3.12 (2H, m), 2.79-2.98 (3H, m), 2.63 (1H, t, 11.5 Hz), 1.55 (1H, quintet, 7H), 0.64 (3H, d, 7 Hz), 0.51 (3H, d, 7 Hz); LCMS (12 minute method): m/z 344.1 [M−HCl+H]+, $R_T$ 5.14 min.

Example 11

Preparation of 1-[5-fluoro-2-(methyloxy)phenyl]-4-methyl-2-morpholin-2-yl-pentan-2-ol hydrochloride (32)

1-[5-Fluoro-2-(methyloxy)phenyl]-4-methyl-2-[4-phenylmethyl)morpholin-2-yl]pentan-2-ol (31)

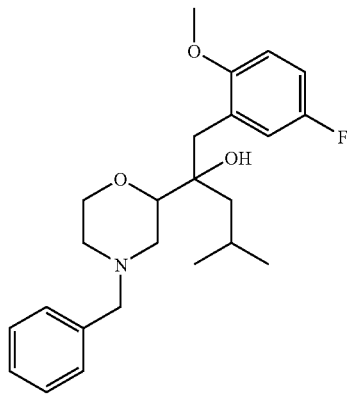

Compound 31 is obtained from 6 (465 mg, 1.78 mmol) and 2-methoxy-5-fluorobenzyl magnesium bromide (3.92 mL, 1.96 mmol, 1.1 equiv.) in dry THF (0 mL) following General Procedure 2. Purification by ion exchange chromatography followed by automated column chromatography (eluent, EtOAc/n-heptane 0/100 to 40/60 [v/v]) gives 31 as an oil (448 mg, 83% purity). MW 401.53; $C_{24}H_{32}FNO_3$; LCMS (6 minute method): m/z 402.2 [M+H]+, $R_T$ 3.40 min.

1-[5-Fluoro-2-(methyloxy)phenyl]-4-methyl-2-morpholin-2-ylpentan-2-ol hydrochloride (32)

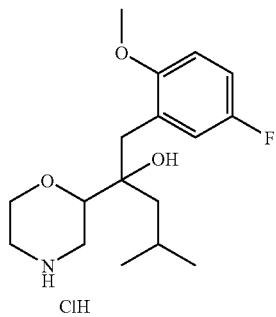

32 is obtained from 31 (448 mg, 1.12 mmol), α-chloroethyl chloroformate (0.48 mL, 4.47 mmol, 4 eq) and polymer-supported Hünig's base (628 g, 2.23 mmol, 2 eq) in DCM (10 mL) following General Procedure 3. Purification by ion exchange chromatography followed by preparative LCMS and conversion to its hydrochloride salt following General Procedure 4 gives 32 as a white solid (0.11 g, 32%). MW 347.72; $C_{17}H_{26}FNO_3 \cdot HCl$; $^1H$ NMR ($CD_3OD$) δ 7.05-7.08 (1H, m), 6.95-6.98 (2H, m), 4.16 (1H, dd, 3 Hz, 12.5 Hz), 3.75-3.86 (4H, m), 3.67 (1H, d, 10.5 Hz), 3.51 (1H, d, 12 Hz), 3.25-3.29 (1H, m), 3.07-3.20 (2H, m), 2.94 (2H, 14 Hz), 1.86-1.9 (1H, m), 1.53 (1H, dd, 5.5 Hz, 14.5 Hz), 1.13 (1H, dd, 14.5 Hz, 5.5 Hz), 0.94 (3H, d, 2.5 Hz), 0.92 (3H, d, 2.5 Hz). LCMS (12 minute method): m/z 312.1 [M−HCl+H]+, $R_T$ 4.61 min.

Example 12

Preparation of 1-[2-(ethyloxy)phenyl]-4-methyl-2-morpholin-2-ylpentan-2-ol (34)

1-[2-(Ethyloxy)phenyl]-4-methyl-2-[4-(phenylmethyl)morpholin-2-ylpentan-2-ol (33)

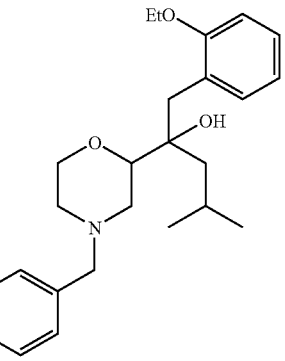

Compound 33 is obtained from 6 (3.0 g, 11.5 mmol) and 2-ethoxybenzyl magnesium chloride (available from Rieke Metals) (0.25M in diethyl ether, 50.5 mL, 12.6 mmol) in anhydrous THF (55 mL) following General Procedure 2. Another two equivalents of 2-ethoxybenzyl magnesium chloride (92 mL 1,23 mmol) are added after 30 min Purification by automated column chromatography (eluent, EtOAc/n-heptane 100 to 25M5 [v/v]) gives 33 (3.21 g) as a colourless oil in 86% purity as a mixture of diastereomers. MW 397.56; $C_{25}H_{35}NO_3$. LCMS (6 minute method): m/Z 398.3 [M+H]+, $R_T$ 3.42 & 3.60 min.

1-[2-(Ethyloxy)phenyl]-4-methyl-2-morpholin-2-ylpentan-2-ol (34)

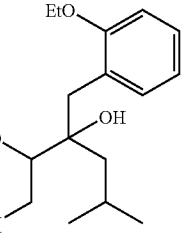

34 is obtained from 33 (3.20 mg, 8.06 mmol), α-chloroethyl chloroformate (3.48 mL, 32.2 mmol) and polymer-supported Hünig's base (4.53 g, 16.1 mmol) in DCM (100 mL) following General Procedure 3. Purification by ion exchange chromatography followed by automated column chromatography (eluent, MeOH/DCM 5/95 to 40/60 [v/v]), and preparative LCMS gives 34. Chiral preparative chromatography (n-heptane:EtOH:DEA 60:40:0.2 gradient, chiralcel-OD) afforded the first eluting enantiomer 34a (13 mg) ($R_T$ 8.25 min), and the second eluting enantiomer 34b ($R_T$ 10.17 min) as colourless oils. MW 307.44; $C_{18}H_{29}NO_3$; $^1$H NMR (CDCl$_3$) δ 7.16-7.22 (2H, m), 6.84-6.93 (2H, m), 3.97-4.17 (2H, m), 3.90 (1H, dd, 3 Hz, 11 Hz), 3.53 (1H, td, 3 Hz, 11 Hz), 3.37 (1H, dd, 2 Hz, 10 Hz), 3.18 (1H, d, 12 Hz), 3.04 (1H, d, 14 Hz), 2.74-2.91 (4H, m), 1.89 (1H, septet, 6 Hz), 1.52 (1H, dd, 5.5 Hz, 14 Hz), 1.44 (3H, t, 7 Hz), 1.11 (1H, dd, 6 Hz, 14 Hz), 0.93 (3H, d, 7 Hz), 0.90 (3H, d, 7 Hz); LCMS (12 minute method): m/z 308.2 [M−HCl+H]$^+$, $R_T$ 40.92 min.

Example 13

Preparation of 4-methyl-2-morpholin-2-yl-1-{2[(trifluoromethyl)-oxy]phenyl}pentan-2-ol hydrochloride (36)

4-Methyl-2-[4-phenylmethyl)morpholin-2-yl]-1-2 [trifluoromethyl)oxy]phenyl}pentan-2-ol (35)

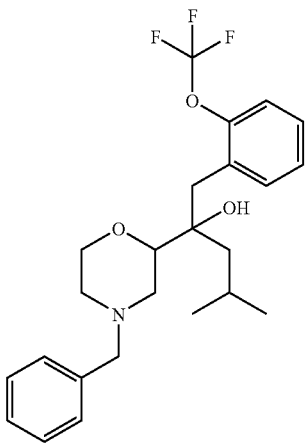

Compound 35 is prepared from 6 (0.83 g, 3.19 mmol) and commercially available (Fluorochem) 2-trifluoromethoxy benzyl magnesium bromide (0.5M solution in THF, 7.02 mL, 3.51 mmol, 1.1 eq) in anhydrous THF (21 mL) following General Procedure 2. Further equivalents (3.19 mL, 1.60 mmol) of 2-trifluoromethoxy benzyl magnesium bromide are added after 30 min. Purification by ion exchange chromatography gives 35 as yellow oil (1.39 g, 99.5%). MW 437.51; $C_{24}H_{30}F_3NO_3$; LCMS (6 minute method): m/z 438.1 [M+H]$^+$, $R_T$ 3.70 min.

4-Methyl-2-morpholin-2-yl-1-{2-[(trifluoromethyl)oxy]phenyl}pentan-2-ol hydrochloride (36)

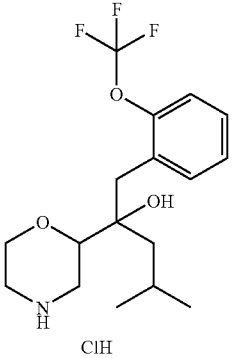

36 is obtained from 35 (1.39 g, 3.18 mmol), α-chloroethyl chloroformate (1.37 mL, 12.7 mmol, 4 eq), and polymer-supported Hünig's base (1.79 g, 6.36 mmol, 2 eq) in DCM (25 mL) following General Procedure 3. Purification by ion exchange chromatography followed by preparative LCMS and conversion into the hydrochloride salt following General Procedure 4 gives 36 (0.16 g, 14%) as foam. MW 383.82; $C_{17}H_{24}F_3NO_3$·HCl; $^1$H NMR (CD$_3$OD) δ 7.43 (1H, d, 7 Hz), 7.16-7.27 (3H, m), 4.05 (1H, dd, 3 Hz, 13 Hz), 3.58-3.74 (2H, m), 3.35-3.40 (1H, m), 3.23-3.14 (1H, m), 2.97-3.10 (3H, m), 2.76 (1H, d, 14 Hz), 1.75 (1H, septet, 6.5 Hz), 1.42 (1H, dd, 6 Hz, 14.5 Hz), 0.98-1.11 (1H, m) 0.83 (3H, d, 6 Hz), 0.81 (3H, d, 6 Hz); LCMS (12 minute method): m/z 348.4 [M−HCl+H]$^+$, $R_T$ 3.15 min.

Example 14

Preparation of 1-[1,1'-Biphenyl]-2-yl-4-methyl-2-morpholin-2-ylpentan-2-ol hydrochloride (38)

2-(4-Benzyl-morpholin-2-yl)-1-biphenyl-2-yl-4-methyl-pentan-2-ol (37)

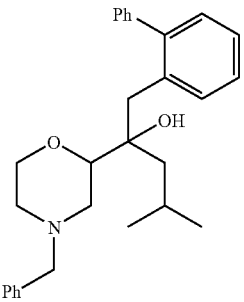

Compound 37 is prepared from 6 (2.5 g, 9.56 mmol) and 2-phenylbenzyl magnesium bromide (0.25M sol., 42.1 mL, 10.5 mmol, 1.1 eq) in anhydrous THF (21 mL) following General Procedure 2. 2-Phenylbenzyl magnesium bromide is prepared from commercially available (Aldrich) 2-phenylbenzyl bromide following General Procedure 5. Another 3 equivalents of 2-phenylbenzyl magnesium bromide are added to drive the reaction to completion. Purification by automated column chromatography eluent, EtOAc/n-heptane 0/100 to 25/75 [v/v],) gives 37 (2.07 g, 50%), which is used in the next step without further purification. MW 429.61; $C_{29}H_{35}NO_2$; FIA$^+$: m/z 430 [M+H]$^+$.

1-[1,1'-Biphenyl]-2-yl-4-methyl-2-morpholin-2-yl-pentan-2-ol (38)

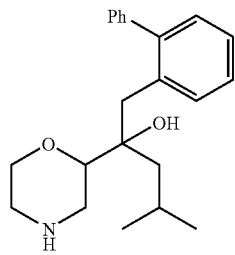

Compound 38 is obtained from 37 (2.07 g, 4.81 mmol), α-chloroethyl chloroformate (2.08 mL, 19.3 mmol) and polymer-supported Hünig's base (2.7 g, 9.6 mmol) in DCM (60 mL) following General Procedure 3. Purification by ion exchange chromatography, crystallization from MeOH/diethyl ether gives 38 as a white solid (738 mg, 45%). MW 339.48; $C_{22}H_{29}NO_2$; $^1$H NMR (CDCl$_3$) δ 7.29-7.46 (8H, m), 7.23-7.28 (1H, m), 3.79-3.91 (2H, m), 3.66 (1H, dd, 10.9 Hz, 1.7 Hz), 3.18 (2H, dd, 12.8 Hz, 25.8 Hz), 2.84-3.04 (3H, m), 2.75 (1H, t, 11.5 Hz), 1.56-1.68 (1H, m), 1.22 (1H, dd, 5.65 Hz, 14.7 Hz), 0.98 (1H, dd, 5.65 Hz, 14.7 Hz), 0.81 (3H, d, 3.2 Hz), 0.78 (3H, d, 3.0 Hz). LCMS (12 minute method): m/z 340.3 [M+H]$^+$, R$_T$ 5.62 min.

Phenylmethyl-2-[1,1'-biphenyl]-2-ylmethyl)-1-hydroxy-3-methylbutyl]morpholine-4-carboxylate (cbz-38)

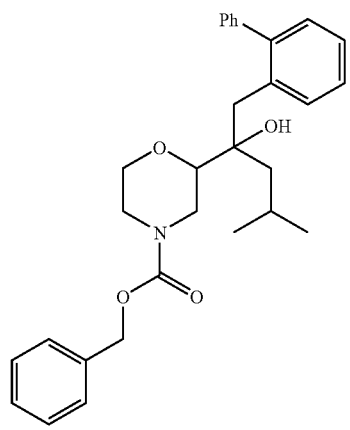

Benzyl chloroformate (0.37 mL, 2.61 mmol) is added to a stirring mixture of 38 (738 mg, 2.17 mmol) with NaHCO$_3$ (0.41 g) in a suspension of diethylether and water (24 mL) under N$_2$ at room temperature. After 1 hour the reaction is quenched with ice water (15 mL) and diluted with DCM. The two phases are separated, the aqueous phase is further extracted DCM, the combined organic fractions are dried over magnesium sulphate, filtered and evaporated in vacuo. The isolated oil is purified using automated column chromatography (eluent, EtOAc/n-heptane 0/100 to 30/70[v/v]) followed by chiral preparative chromatography (Heptane:EtOH:DEA 35:65:0.2 gradient, chiracel AD-H) to give the first eluting enantiomer, cbz-38a (R$_T$ 2.61 min), and the second eluting enantiomer, cbz-38b (R$_T$ 2.99 min), both as a colourless oil. MW 473.62; $C_{30}H_{35}NO_4$: LCMS (6 minute method): m/z 456.3 [M–H$_2$O+H]$^+$ and 496.2 [M+Na]$^+$; R$_T$ 5.34 min.

1-[1,1'-Biphenyl]-2-yl-4-methyl-2-morpholin-2-yl-pentan-2-ol hydrochloride (38a)

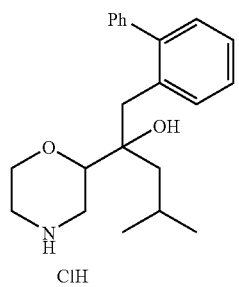

Palladium on carbon (10% weight) (0.4 g) is added to a stirring solution of cbz-38a (0.39 g, 0.84 mmol) with ammonium formate (0.53 g, 8.4 mmol) in ethanol (10 mL) at room temperature under nitrogen. The heterogeneous mixture is heated to reflux for 30 minutes, allowed to cool to room temperature and then filtered through a Celite pad. The filtrate is concentrated in vacuo, purified by ion exchange chromatography and then converted to the hydrochloride salt following General Procedure 4 to give 38a (0.25 g, 79%) as a yellow solid. MW 375.94; $C_{22}H_{29}NO_2$.HCl: $^1$H NMR (CD$_3$OD) δ 7.48 (1H, bs), 7.11-7.33 (8H, m), 3.87 (1H, bs), 3.37-3.57 (2H, m), 3.25 (1H, s), 2.77-3.10 (5H, m), 1.54 (1H, s, br), 1.07-1.19 (1H, m), 0.93-1.00 (1H, m), 0.72 (3H, d, 6 Hz), 0.69 (3H, d, 6 Hz): LCMS (12 minute method): m/z 340.2 [M–HCl+H]$^+$, R$_T$ 5.30 min.

Example 15

Preparation of 1-(4-fluoro[1,1'-biphenyl]-2-yl)-4-methyl-2-morpholin-2-ylpentan-2-ol hydrochloride (40)

1-(4-Fluoro[1,1'-biphenyl]-2-yl-4-methyl-2-[4-(phenylmethyl)morpholin-2-yl]pentan-2-ol (39)

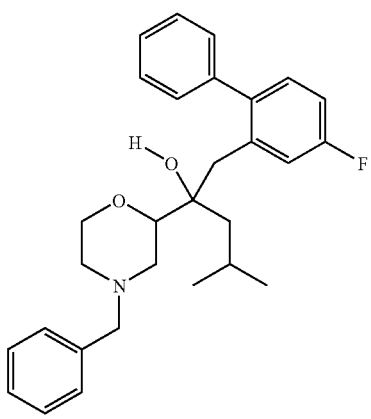

Compound 39 is prepared from 6 (0.95 g, 3.65 mmol) and 2-phenyl-5-fluoro benzyl magnesium bromide (0.5M solution in diethyl ether, 1.2 eq) following General Procedure 2.

2-Phenyl-5-fluorobenzyl magnesium bromide is obtained from 2-phenyl-5-fluorobenzyl bromide following General Procedure 5. Excess 2-phenyl-5-fluoro benzyl magnesium bromide is subsequently added at room temperature and the reaction left stirring for 1 hour. Purification by column chromatography (eluent, EtOAc/cyclohexane 50/50 [v/v]) gives 39 as a viscous oil (1.31 g, 80%). MW 447.60; $C_{29}H_{34}FNO_2$. LCMS: (6 minute method) m/z 448 $[M+H]^+$, $R_T$ 3.88 min.

1-(4-Fluoro[1,1'-biphenyl]-2-yl)-4-methyl-2-morpholin-2-ylpentan-2-ol hydrochloride (40)

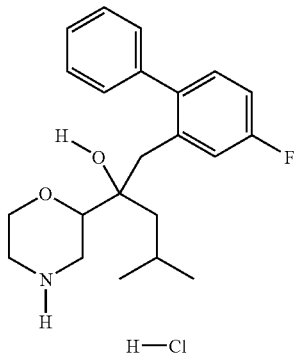

40 is prepared from 39 (1.31 g, 2.92 mmol), α-chloroethyl chloroformate (0.9 mL) and solid supported Hünig's base (1.64 g) in anhydrous DCM (30 mL) following General Procedure 3. Purification by ion exchange chromatography gives the free base of 40 as a viscous oil (0.71 g, 62%). After further purification using UV-guided preparative LCMS, the hydrochloride salt 40 (0.451 g, 39%) is obtained following General Procedure 4. MW 393.95; $C_{22}H_{28}FNO_2$.HCl; $^1$H NMR (DMSO-$d_6$): δ 9.16 (1H, s), 8.98 (1H, s), 7.44-7.32 (4H, m), 7.23-7.06 (4H, m), 3.83 (1H, dd, 12 Hz, 3 Hz), 3.59-3.50 (3H, m), 3.18 (1H, d, 12.5 Hz), 3.08 (1H, d, 12.5 Hz), 2.92-2.67 (4H, m), 1.54-1.40 (1H, m), 1.03 (1H, dd, 14.5 Hz, 5 Hz), 0.88 (1H, dd, 14.5 Hz, 6.5 Hz), 0.74 (3H, d, 6.5 Hz), 0.67 (3H, d, 6.5 Hz); LCMS: (12 minute method) m/z 358 $[M-HCl+H]^+$ $R_T$ 5.47 min.

Example 16

Preparation of 1-cyclopentyl-2-[5-fluoro-2-(methyloxy)phenyl]-1-morpholin-2-ylethanol hydrochloride (42)

1-Cyclopentyl-2-[5-fluoro-2-(methyloxy)phenyl]-1-[4-(phenylmethyl)morpholin-2-yl]ethanol (41)

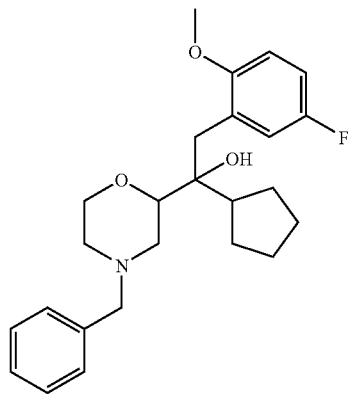

Compound 41 is obtained from 7 (0.7 g, 2.56 mmol) and 2-methoxy-5-fluorobenzyl magnesium bromide (5.63 mL, 2.82 mmol 1.1 eq) in anhydrous THF (15 mL) following General Procedure 2. Further equivalents of 2-methoxy-5-fluorobenzyl magnesium bromide (8.49 mL, 4.25 mmol) are added. Purification by ion exchange chromatography gives 41 as a yellow oil (843 mg, 62% purity). MW 413.54; $C_{25}H_{32}FNO_3$; LCMS (6 minute method): m/z 414.2 $[M+H]^+$. $R_T$ 4.11 min.

1-Cyclopentyl-2-[5-fluoro-2-(methyloxy)phenyl]-1-morpholin-2-ylethanol hydrochloride (42)

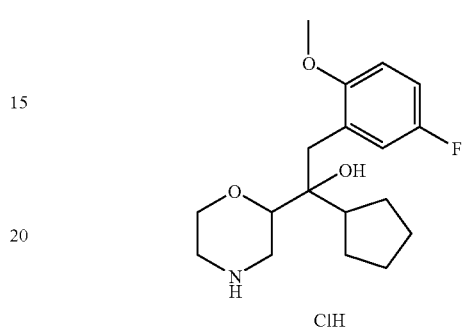

The free base of 42 is obtained from 41 (0.84 g, 2.04 mmol), α-chloroethyl chloroformate (0.88 mL, 8.16 mmol, 4 eq) and polymer-supported Hünig's base (1.15 g, 4.08 mmol, 2 eq) in DCM (15 mL) following General Procedure 3. Purification by ion exchange chromatography, followed by automated chromatography (DCM/MeOH 95/5 to 80/20 [v/v]) and preparative LCMS and conversion into the hydrochloride salt following General Procedure 4 gives 42 as a colourless gum (0.18 g, 14.1%). MW 359.82; $C_{18}H_{26}FNO_3$.HCl; $^1$H NMR (CD$_3$OD) δ 7.11-7.14 (1H, m), 6.95-6.97 (2H, m), 4.07-4.15 (1H, m), 3.67-3.75 (2H, m), 3.43 (1H, d, 12 Hz), 3.23 (3H, s), 3.22 (1H, d, 12 Hz), 2.92-3.10 (4H, m), 2.13-2.19 (1H, m), 1.42-1.73 (8H, m); LCMS (12 minute method): m/z 324.1 $[M-HCl+H]^+$, $R_T$ 4.83 min.

Example 17

Preparation of 1-cyclopentyl-2-[2-(ethyloxy)phenyl]-1-morpholin-2-ylethanol hydrochloride (44)

1-Cyclopentyl-2-[2-(ethyloxy)phenyl]-1-[4-(phenylmethyl)morpholin-2-yl]ethanol (43)

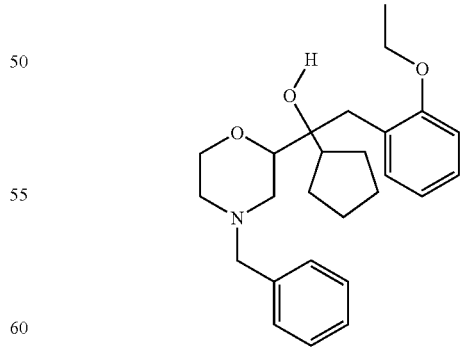

Compound 43 is obtained from 7 (2.09 g, 7.68 mmol) and 2-ethyloxy benzyl magnesium bromide (available from Rieke Metals) (0.25M solution in diethyl ether, 1.1 eq) following General Procedure 2. Purification by preparative LCMS gives 43 as viscous oil (0.691 g, 22%). MW 409.57; $C_{26}H_{35}NO_3$; LCMS: (6 minute method) m/z 410 $[M+H]^+$, $R_T$ 3.8 min.

1-Cyclopentyl-2-[2-(ethyloxy)phenyl]-1-morpholin-2-ylethanol hydrochloride (44)

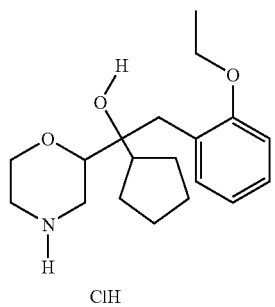

The free base of 44 is obtained from 43 (0.691 g, 1.69 mmol), α-chloroethyl chloroformate (0.80 mL) and solid supported Hünig's base (0.95 g) in anhydrous DCM following General Procedure 3. Purification by ion exchange and conversion into its hydrochloride salt following General Procedure 4 gives 44 (0.39 g, 65%) MW 355.91; $C_{19}H_{29}NO_3 \cdot HCl$; $^1H$ NMR ($CD_3OD$): δ 7.12-7.22 (2H, m), 6.82-6.88 (2H, m), 4.09-4.16 (3H, m), 3.69-3.80 (2H, m), 2.80-3.29 (6H, m), 2.04-2.10 (1H, m), 1.53-1.73 (11H, m); LCMS: (12 minute method) m/z 320 [M–HCl+H]$^+$, $R_T$ 5.03 min.

Example 18

Preparation of 1-Cyclopentyl-1-morpholin-2-yl-2-{2-[(trifluoromethyl) oxy]phenyl}-ethanol hydrochloride (46)

1-Cyclopentyl-2-[5-fluoro-2-(methyloxy)phenyl]-1-[4-(phenylmethyl) morpholin-2-yl]ethanol (45)

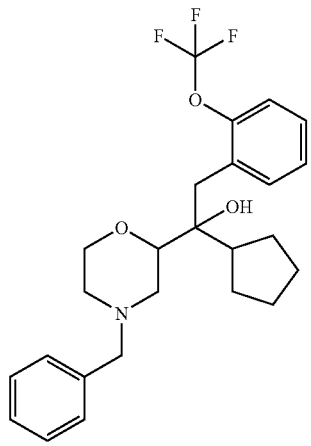

Compound 45 is obtained from 7 (0.6 g, 2.19 mmol) and commercially available (Fluorochem) 2-trifluoromethoxy-benzyl magnesium bromide (0.5M solution in diethylether, 4.8 mL, 2.41, mmol, 1.1 eq) in anhydrous THF (15 mL) following General Procedure 2. After addition of another 2 equivalents of 2-trifluoromethoxy-benzyl magnesium bromide and stirring for 2 hours at 0° C. purification by ion exchange chromatography gives 45 (0.89 g, 90%). MW 449.52; $C_{25}H_{30}F_3NO_3$. LCMS (6 minute method): m/z 450.2 [M+H]$^+$, $R_T$ 4.084 min.

1-Cyclopentyl-1-morpholin-2-yl-2-{2-[(trifluoromethyl)oxy]phenyl}-ethanol hydrochloride (46)

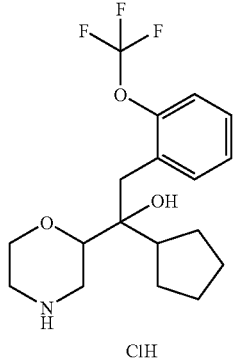

The free base of 46 is obtained from 45 (886 mg, 1.97 mmol), α-chloroethyl chloroformate (0.85 mL, 7.9 mmol, 4 eq) and polymer-supported Hünig's base (1.11 g, 3.94 mmol, 2 eq) in DCM (15 mL) following General Procedure 3. Purification by ion exchange chromatography followed by preparative LCMS and conversion to its hydrochloride salt following General Procedure 4 gives 46 as a gum (140 mg, 20%). MW 395.85; $C_{18}H_{24}F_3NO_3 \cdot HCl$; $^1H$ NMR ($CD_3OD$) δ 7.48-7.50 (1H, m), 7.14-7.25 (3H, m), 3.97 (1H, dd, 2.3 Hz, 12.5 Hz), 3.60-3.68 (2H, m), 3.27-3.31 (1H, m), 3.03 (2H, 12.5 Hz), 2.73-2.97 (3H, m), 2.00-2.11 (1H, m), 1.30-1.63 (8H, m); LCMS (12 minute method): m/z 360.14 [M–HCl+H]$^+$, $R_T$ 5.14 min.

Example 19

Preparation of 2-[1,1'-biphenyl]-2-yl-1-cyclopentyl-1-morpholin-2-ylethanol hydrochloride (48)

2-[1,1'-Biphenyl]-2-yl-1-cyclopentyl-1-[4-(phenylmethyl)morpholin-2-yl]ethanol (47)

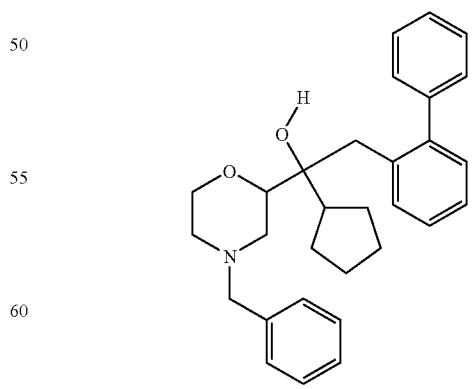

Compound 47 is prepared from 7 (1.27 g, 4.65 mmol) and 2-phenylbenzyl magnesium bromide (0.25 M solution in diethyl ether, 1.1 eq) following General Procedure 2. 2-Phenylbenzyl magnesium bromide is prepared from commercially available (Aldrich) 2-phenylbenzyl bromide following General Procedure 5. Purification by flash column chromatography (eluent, cyclohexane/EtOAc 90/10 [v/v]) gives 47 as viscous oil (1.75 g). 47 is taken onto the next step without further purification. MW 441.62; $C_{30}H_{35}NO_2$; LCMS: (6 minute method) m/z 442 [M+H]$^+$, $R_T$ 3.51 min.

2-[1,1'-Biphenyl]-2-yl-1-cyclopentyl-1-morpholin-2-ylethanol hydrochloride (48)

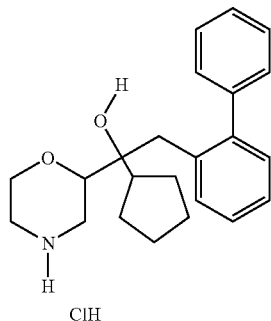

The free base of 48 is prepared from 47 (1.75 g, 3.95 mmol), solid supported Hünig's base (2.22 g) and α-chloroethyl chloroformate (1.62 mL) in anhydrous DCM (30 mL) following General Procedure 3. Purification by ion exchange chromatography followed by flash column chromatography (eluent, MeOH/DCM 1/99 to 20/80 [v/v]) gives the free base as a viscous oil (805 mg, 58%) which is converted into 48 following General Procedure 4. MW 387.95; $C_{23}H_{29}NO_2$.HCl; $^1$H NMR (CD$_3$OD): δ 7.66-7.40 (1H, m) 7.19-7.47 (8H, m), 3.92 (1H, dd, 13 Hz, 3.5 Hz), 3.59-3.67 (2H, m), 3.05-3.16 (4H, m), 2.93 (1H, td, 13 Hz, 3.5 Hz,), 2.59 (1H, t, 12 Hz), 1.98-1.88 (1H, m), 1.55-1.19 (8H, m); LCMS: (12 minute method) m/z 351 [M−HCl+H]$^+$, $R_T$ 5.68 min.

Example 20

Preparation of 1-cyclopentyl-2-(4-fluoro[1,1'-biphenyl]-2-yl)-1-morpholin-2-ylethanol hydrochloride (50)

1-Cyclopentyl-2-(4-fluoro[1,1'-biphenyl]-2-yl)-1-[4-(phenylmethyl)morpholin-2-yl]ethanol hydrochloride (49)

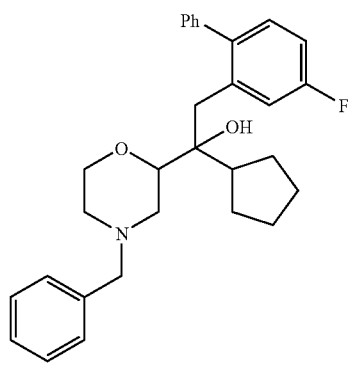

Compound 49 is obtained from 7 (0.9 g, 3.29 mmol) and 2-phenyl-5-fluorobenzyl magnesium bromide (0.5M solution in THF, 7.24 mL, 3.62 mmol) in anhydrous THF (20 mL) following General Procedure 2. 2-Phenyl-5-fluorobenzyl magnesium bromide is prepared from 2-phenyl-5-fluorobenzyl bromide following General Procedure 5. Further 2-phenyl-5-fluorobenzyl magnesium bromide is added after 30 min (0.3 eq, 2 mL, 0.99 mmol). Purification by ion exchange chromatography followed by automated column chromatography eluent, EtOAc/n-heptane 0/100 to 20/80 [v/v]) gives 49 (1.26 g, 83%) as a colourless liquid. MW 459.61; $C_{30}H_{34}FNO_2$; LCMS (6 minute method): m/z 460.5 [M+H]$^+$, $R_T$ 3.98 min.

1-Cyclopentyl-2-(4-fluoro[1,1'-biphenyl]-2-yl)-1-morpholin-2-ylethanol hydrochloride (50)

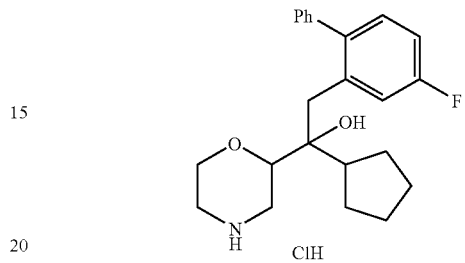

The free base of 50 is obtained from 49 (1.26 mg, 2.73 mmol), α-chloroethyl chloroformate (1.18 mL, 10.9 mmol) and polymer-supported Hünig's base (1.54 g, 5.47 mmol) in DCM (25 mL) following General Procedure 3. Purification by ion exchange chromatography followed by automated column chromatography eluent, MeOH/DCM 100 to 20/80 [v/v]) and conversion to its hydrochloride salt gives 50 as a yellow solid (0.23 g, 23%). MW 405.94; $C_{23}H_{28}FNO_2$.HCl; $^1$H NMR (CD$_3$OD) δ 7.20-7.37 (6H, m), 7.08-7.13 (1H, m), 6.91 (1H, td, 3.5 Hz, 8.5 Hz), 3.80 (1H, dd, 3.5 Hz, 13.0 Hz), 3.42-3.54 (2H, m), 2.99-3.06 (2H, m), 2.93 (2H, s), 2.83 (1H, td, 4.0 Hz, 12.5 Hz), 2.53 (1H, t, 12.0 Hz), 1.73-1.85 (1H, m), 1.12-1.44 (8H, m). LCMS (12 minute method): m/z 370.2 [M−HCl+H]$^+$, $R_T$ 5.46 min.

Example 21

Preparation of 2-[5-fluoro-2-(methyloxy)phenyl]-1-morpholin-2-yl-1-tetrahydro-2H-pyran-4-ylethanol hydrochloride (52)

2-[5-Fluoro-2-(methyloxy)phenyl]-1-[4-(phenylmethyl)morpholin-2-yl]-1-tetrahydro-2H-pyran-4-ylethanol (51)

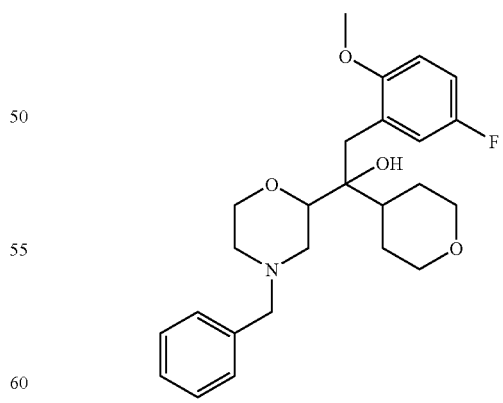

Compound 51 is obtained from 8 (0.6 g, 2.07 mmol) and 2-methoxy-5-fluorobenzyl magnesium bromide (4.6 mL, 2.28 mmol, 1.1 eq) in anhydrous THF (15 mL) following General Procedure 2. Further equivalents of 2-methoxy-5-fluorobenzyl magnesium bromide (8.28 mL, 4.14 mmol) are added and the mixture is warmed to room temperature and left stirring over night. Purification by ion exchange chromatography followed by automated chromatography (eluent, n-heptane/EtOAc 90/10 to 30/70 [v/v]) gives 51 as a colourless oil (375 mg, 42%). MW 429.54; $C_{25}H_{32}FNO_4$; LCMS (6 minute method): m/z 430.2 $[M+H]^+$, $R_T$ 3.12 min.

2-[5-Fluoro-2-(methyloxy)phenyl]-1-morpholin-2-yl-1-tetrahydro-2H-pyran-4-ylethanol hydrochloride (52)

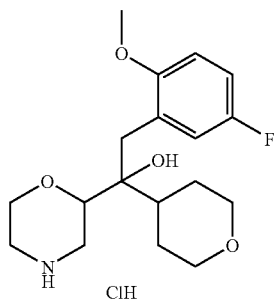

The free base of 52 is obtained from 51 (0.31 g, 0.73 mmol), α-chloroethyl chloroformate (0.31 mL, 2.9 mmol) and polymer-supported Hünig's base (0.41 g, 1.45 mmol) in DCM (7 mL) following General Procedure 3. Purification by ion exchange chromatography and conversion to the hydrochloride salt following General Procedure 4 gives 52 as a white solid (0.19 g, 77%/0). MW 375.82; $C_{18}H_{26}FNO_4$·HCl; $^1$H NMR (CD$_3$OD): δ 6.98-7.01 (1H, m), 6.83-6.86 (2H, m), 3.99 (1H,dd, 3.5 Hz, 13 Hz), 3.82-3.87 (2H, m), 3.63-3.73 (5H, m), 3.12-3.33 (4H, m), 2.91-3.02 (2H, m), 2.81 (2H, 14 Hz), 1.31-1.73 (5H, m); LCMS (12 minute method): m/z 340.2 $[M-HCl+H]^+$, $R_T$ 3.78 min.

Example 21a

Preparation of 2-[5-fluoro-2-(methyloxy)phenyl]-1-morpholin-2-yl-1-tetrahydro-2H-pyran-4-ylethanol hydrochloride (52b)

2-[5-Fluoro-2-(methyloxy)phenyl]-1-[4-(phenylmethyl)morpholin-2-yl]-1-tetrahydro-2H-pyran-4-ylethanol hydrochloride (51b)

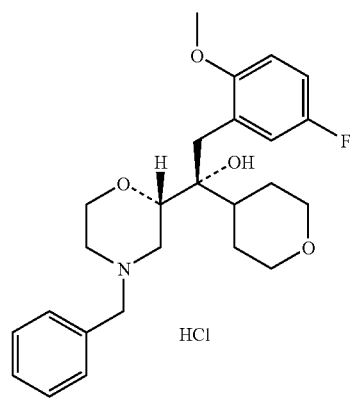

2-Methoxy-5-fluoro-benzylbromide (455.6 g, 2.079 mol) is dissolved in toluene (1592 mL). 8b (400.8 g, 1386 mmol) is dissolved in toluene (400 mL). An inerted 20 L vessel is charged with 2-MeTHF (1202 mL), magnesium (50.59 g, 2.079 mol) and 1.5M DIBALH (16 mL). The benzyl bromide solution is charged in a funnel flask then an initial charge of 5% of the total amount of benzyl bromide is added to the magnesium mixture at 22° C. After 15 mins, the remainder of the benzyl bromide solution is added over 160 mins at room temperature. After an additional 1 h stirring, the 8b solution is slowly added to the mixture over 140 mins at −15° C. After a further 30 mins, the quench is performed by addition of acetic acid (124 mL) keeping the temperature below −5° C., then a 10/1 v/v water/acetic acid mixture (2200 mL) is added keeping the temperature below 10° C. The organic layer is extracted at room temperature, filtered to remove Mg turnings and left overnight. The organic layer is washed with water (500 mL), then basification is performed by addition of water (1600 mL) and NH$_3$aq (311.8 mL). The organic layer is concentrated and i-propanol (2000 mL) is added. The azeotrope toluene/1-propanol is stripped off under reduced pressure, then i-propanol is removed. The brown-orange oil is dissolved in i-propanol (2380 mL) then 12N HClaq (138.6 mL) and water (2380 mL) are added. The apolar impurities are removed with a cyclohexane wash (4760 mL). Then, the aqueous layer is basified with NH$_3$aq and extracted with toluene (4 L). The organic layer is washed with water (500 mL), then the combined aqueous layers are extracted with toluene (4 L) and then this new toluene solution is washed with water (500 mL). The combined organic layers are concentrated under reduced pressure, then i-propanol (2 L) is added and the solution is concentrated again to provide a crude oil of 51b (550 g, 91% yield; 94% ee) and 100 g of i-propanol. This crude oil is diluted with THF (2000 mL) and 8.76M HBraq (153.9 mL) is added. This mixture is allowed to stir overnight and a thin suspension is observed. The precipitate is filtered and washed with THF (150 mL) to give 34 g of racemic 51 as the HBr salt. The mother liquors are concentrated then toluene (1500 mL), water (500 mL) and NH$_3$aq (103.58 mL, 1.386 mol) are added. The organic layer is extracted and washed with water (250 mL). The combined aqueous layers are extracted with toluene (500 mL). The combined organic layers are dried over MgSO$_4$ and concentrated under reduced pressure, then i-propanol (2 L) is added and stripped off again. Then, the oil is dissolved in i-propanol (1 L), 12N HCl (121.3 mL) is added and the mixture is allowed to stir for 15 mins, then the solvent is partially stripped off to provide 51b as the desired diastereoisomer (1021 g; 98.4% ee)

2-[5-Fluoro-2-(methyloxy)phenyl]-1-morpholin-2-yl-1-tetrahydro-2H-pyran-4-ylethanol hydrochloride (52b)

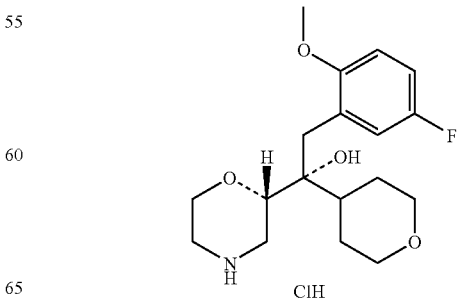

A 6 L Parr bottle is loaded with 51b (1021 g), i-propanol (3630 mL) and water (639 mL). After purging with N₂, 5% Pd—C 52% wet is added (105.6 g) and the mixture is then pressurized with hydrogen (50 psi). The reaction mixture is shaken for 9 h 30 mins, then the mixture is filtered on a Hyflo Super Cel® pad (100 g) pre-imbibed with 80/20 i-propanol/water (500 mL). The catalyst is rinsed with a 80:20: i-propanol:water mixture (500 mL). The solvents are stripped off then i-propanol is added (2000 mL) to be partially removed again. Then i-propanol is re-added (1400 mL) and the heterogeneous mixture is concentrated to provide an off-white solid To this crude alcohol 52b is added i-propanol (4474 mL) and the mixture is heated to reflux until a homogeneous solution is formed. Then, the mixture is cooled slowly and the crystallization starts at 60° C. The powder is filtered at room temperature, rinsed with i-propanol (2×350 mL) and dried under reduced pressure at 40° C. to give highly pure compound 52b with 80% recovery yield (98.4% de, 99.2% ee).

Example 22

Preparation of 1-morpholin-2-yl-1-tetrahydro-2H-pyran-4-yl-2-{2-[(trifluoromethyl)oxy]phenyl}ethanol hydrochloride (54)

1-[4-(Phenylmethyl)morpholin-2-yl]-1-tetrahydro-2H-pyran-4-yl-2-{2-[(trifluoromethyl)oxy]phenyl}ethanol (53)

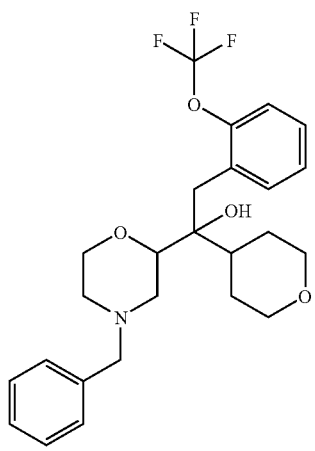

Compound 53 is obtained from 8 (0.61 g, 2.11 mmol) and commercially available (Fluorochem) 2-trifluoromethoxy benzyl magnesium bromide (4.6 mL 2.32 mmol, 1.1 eq) in anhydrous THF (15 mL) following General Procedure 2. Further 2-trifluoromethoxy benzyl magnesium bromide (4.22 mL, 2.11 mmol) is added. Purification by ion exchange chromatography gives 53 as an oil of 88% purity (1.39 g isolated material, ca 88% purity) which is directly used in the next step. MW 465.52; $C_{25}H_{30}F_3NO_4$; LCMS (6 minute method): m/z 466.2 [M+H]⁺, $R_T$ 3.67 min.

1-Morpholin-2-yl-1-tetrahydro-2H-pyran-4-yl-2-{2-[(trifluoromethyl)oxy]-phenyl}ethanol hydrochloride (54)

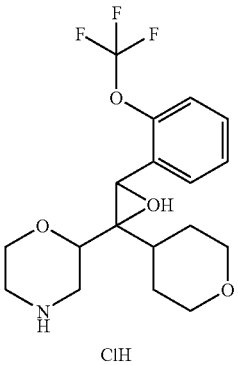

The free base of 54 is obtained from 53 (0.27 g, 0.57 mmol), α-chloroethyl chloroformate (0.25 mL, 2.30 mmol, 4 eq) and polymer-supported Hünig's base (0.32 g, 1.15 mmol, 2 eq) in DCM (5 mL) following General Procedure 3. Purification by ion exchange chromatography followed by preparative LCMS (gradient) and conversion to the hydrochloride salt following General Procedure 4 gives 54 as white solid (82 mg, 17%). MW 411.85; $C_{18}H_{24}F_3NO_4 \cdot HCl$. ¹H NMR (CD₃OD) δ 7.45-7.48 (1H, m), 7.16-7.27 (3H, m), 3.98 (1H, dd, 4.0 Hz, 13 Hz), 3.65-3.88 (4H, m), 3.12-3.31 (4H, m), 2.87-3.01 (4H, m), 1.30-1.68 (5H, m); LCMS (12 minute method): m/z 376.1 [M–HCl+H]⁺, $R_T$ 4.28 min.

Example 23

Preparation of 2-[1,1'-biphenyl]-2-yl-1-morpholin-2-yl-1-tetrahydro-2H-pyran-4-ylethanol hydrochloride (56)

2-[1,1'Biphenyl]-2-yl-1-[4-(phenylmethyl)morpholin-2-yl]-1-tetrahydro-2H-pyran-4-ylethanol (55)

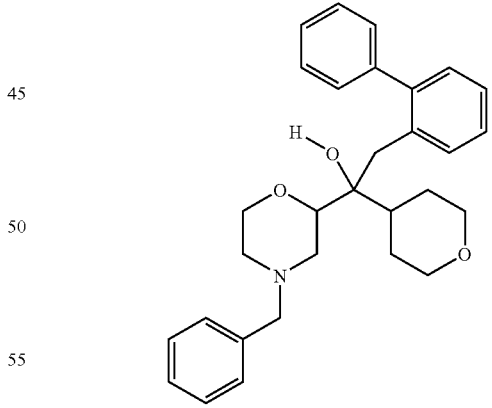

Compound 55 is prepared from 8 (0.56 g, 1.94 mmol) and 2-phenyl benzyl magnesium bromide solution (0.25 M solution in diethyl ether, 9.31 mL, 2,33 mmol, 1.2 eq) following General Procedure 2. 2-Phenylbenzyl magnesium bromide is prepared from commercially available (Aldrich) 2-phenyl-benzyl bromide following General Procedure 5. Further 2-phenyl benzyl magnesium bromide solution (1 mL) is added and the reaction left under stirring overnight. Purification by ion exchange chromatography gives 55 as an off-white foam-like solid (0.37 g, 68%). MW 457.62; C30H35NO3; LCMS. (6 minute method): m/z 458 [M+H]+, RT 3.58 min.

2-[1,1'-Biphenyl]-2-yl-1-morpholin-2-yl-1-tetrahydro-2H-pyran 4-ylethanol hydrochloride (56)

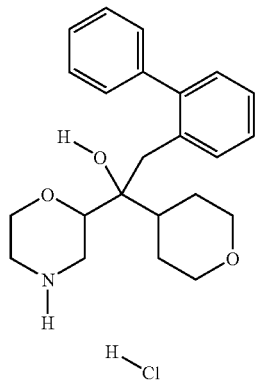

The free base of 56 is obtained from 55 (0.588 g, 1.28 mmol), solid supported Hünig's base (0.72 g) and α-chloroethyl chloroformate (0.53 mL) in anhydrous DCM (20 mL) following General Procedure 3. Purification by ion exchange chromatography gives the free base of 56 as viscous oil (0.483 g), contaminated with a small amount of the N-protected compound 55. The residue is treated with an excess of reagents (1 eq), solid supported Hünig's base (0.36 g) and α-chloroethyl chloroformate (0.26 mL) in anhydrous DCM (20 mL) and methanol (20 mL) and purified by ion exchange chromatography to give the free base of 56 (0.432 g). Purification by preparative LCMS followed by conversion to its hydrochloride salt following General Procedure 4 gives 56 (0.280 g, 54%). MW 403.95; C23H29NO3.HCl; 1H NMR (CD3OD): δ 7.45-7.59 (1H, m), 7.10-7.35 (8H, m), 3.85 (1H, dd, 13 Hz, 3.5 Hz), 3.75 (1H, dd, 11.5 Hz, 3.5 Hz), 3.51-3.59 (3H, m), 2.83-3.12 (7H, m), 2.64 (1H, t, 12 Hz), 1.36-1.52 (2H, m), 1.02-1.21 (2H, m), 0.90-0.94 (1H, m); LCMS: (12 min method) m/z 368 [M–HCl+H]+, RT 4.6 min.

Example 24

Preparation of 2-(3'-Fluoro-biphenyl-2-yl)-1-morpholin-2-yl-1-(tetrahydro-pyran-4-yl)-ethanol (58)

2-Bromophenyl-1-[4-(phenylmethyl)morpholin-2-yl]-1-(tetrahydro-pyran-4-yl)-ethanol

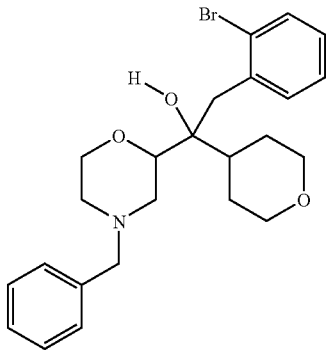

Commercially available (Aldrich) 2-bromobenzyl magnesium bromide (0.25M solution in diethylether, 48.9 mL, 12.18 mmol, 2.6 eq) is added in three portions over 90 minutes to a solution of 8 (1.35 g, 4.7 mmol) in dry THF (30 mL) at 0° C. After quenching with ice water, saturated ammonium chloride solution is added and the aqueous phase washed with EtOAc. The combined organic phases are washed with brine and water, dried over magnesium sulphate and solvents removed in vacuo. Purification by ion exchange chromatography followed by purification using automated column chromatography (eluent, EtOAc/n-heptane 10/90 to 50/50 [v/v]) gives 57 (0.56 g, 26%). MW 460.42; C24H30BrNO3; LCMS (6 minute method): m/z 462.4 [M+H]+, RT 3.11 min.

2-(3'-Fluoro-biphenyl-2-yl)-1-[4-(phenylmethyl)morpholin-2-yl]-1-(tetrahydro-pyran-4-yl)-ethanol (57)

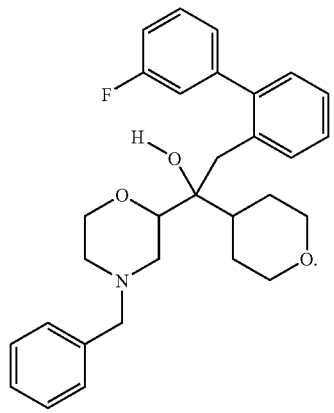

To a suspension of Pd(OAc)2 (2.44 mg, 0.011 mmol, 0.02 eq) in acetonitrile (1.5 mL) is added triphenyl phosphine (11.4 mg, 0.043 mmol, 0.08 eq) under nitrogen at room temperature leading to the formation of a white precipitate. Addition of water (0.5 mL), 3-fluoro-phenyl boronic acid (91.2 mg, 0.65 mmol, 1.2 eq) and 57 (0.25 mg, 0.54 mmol) gives a dark grey solution after 10-20 minutes which is heated to reflux and left stirring at reflux overnight. Further 3-fluoro-phenyl boronic acid (70 mg, 0.55 mmol, 1 eq) and Pd(OAc)2 (2-3 mg) are added and the mixture is left stirring at reflux for another 24 hours. Purification by ion exchange chromatography gives 57 (0.21 g, 83%) MW 475.61; C30H34FNO3; LCMS (6 minute method): m/z 476.4 [M+H]+, RT 3.41 min.

2-(3'-Fluoro-biphenyl-2-yl)-1-morpholin-2-yl-1-(tetrahydro-pyran-4-yl)-ethanol (58)

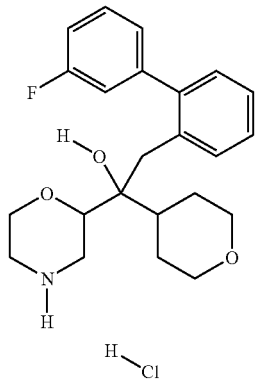

Compound 58 is obtained from 57 (0.213 g, 0.45 mmol), solid supported Hünig's base (0.25 g, 7.12 mmol, 4 eq) and α-chloroethyl chloroformate (0.19 mL, 1.79 mmol, 4 eq) in anhydrous DCM (7 mL) following General Procedure 3. Purification by ion exchange chromatography gives the free base of 58 as a white foam (125 mg) which is further purified by preparative LCMS. Conversion to its hydrochloride salt following General Procedure 4 gives 58 as a yellow gum (96.5 g, 56%). MW 421.94; $C_{23}H_{28}FNO_3HCl$; $^1H$ NMR ($CD_3OD$): δ 7.60-7.45 (1H, m), 6.90-7.45 (6H, m), 3.55-3.95 (5H, m), 2.85-3.30 (10H, m), 2.64 (1H, t, 12.0 Hz), 0.95-1.45 (5H, m); LCMS. (12 minute method): m/z 386 [M–HCl+H]$^+$, $R_T$ 4.64 min.

Example 25

Preparation of 5,5,5-trifluoro-1-(5-fluoro-2-methoxy-phenyl)-2-morpholin-2-yl-pentan-2-ol (60)

5,5,5-Trifluoro-1-[5-fluoro-2-(methyloxy)phenyl]-2-[4-(phenylmethyl)morpholin-2-yl]pentan-2-ol (59)

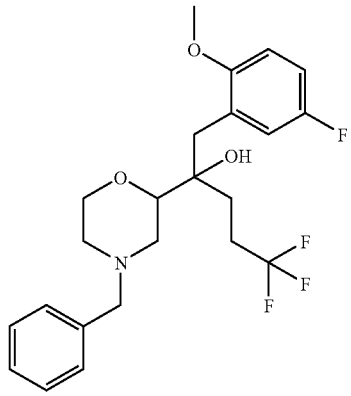

Compound 59 is obtained from 9 (0.7 g, 2.32 mmol) and 2-methoxy-5-fluorobenzyl magnesium bromide (5.11 mL, 2.55 mmol, 1.1 eq) in dry THF (15 mL) following General Procedure 2. Purification by ion exchange chromatography gives 59 as an oil of 80% purity which is directly used in the next step (0.9 g recovered material). MW 441.47; $C_{23}H_{27}F_4NO_4$; LCMS (6 minute method): m/z 442.4 [M+H]$^+$, $R_T$ 3.36 min.

5,5,5-Trifluoro-1-[5-fluoro-2-(methyloxy)phenyl]-2-morpholin-2-yl]pentan-2-ol hydrochloride (60)

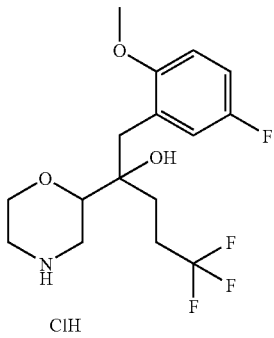

The free base of 60 is obtained from 59 (0.9 g, 2.04 mmol), α-chloroethyl chloroformate (0.88 mL, 8.15 mmol, 4 eq) and polymer-supported Hünig's base (1.15 g, 4.08 mmol, 2 eq) in DCM (25 mL) following General Procedure 3. Purification by ion exchange chromatography followed by preparative LCMS and conversion to the hydrochloride salt following General Procedure 4 gives 60 as a yellow solid (0.133 g, 17%). MW 387.80; $C_{16}H_{21}F_4NO_3$·HCl. $^1H$ NMR ($CD_3OD$): δ 6.93-6.96 (1H, m), 6.86-6.87 (2H, m), 4.09-4.13 (1H, m), 3.68-3.75 (4H, m), 3.42-3.47 (1H, m), 3.34-3.40 (1H, m), 3.16-3.25 (1H, m), 3.03-3.11 (2H, m), 2.83 (2H, 14 Hz), 2.12-2.29 (2H, m), 1.58-1.68 (1H, m), 1.29-1.39 (1H, m). LCMS (12 minute method): m/z 352.1 [M–HCl+H]$^+$, $R_T$ 4.54 and 4.66 min.

Example 26

Preparation of 5,5,5-trifluoro-2-morpholin-2-yl-1-(2-trifluoromethoxy-phenyl)-pentan-2-ol (62)

5,5,5-Trifluoro-2-[4-(phenylmethyl)morpholin-2-yl]-1{2[(-trifluoromethyl)oxy]-phenyl}pentan-2-ol (61)

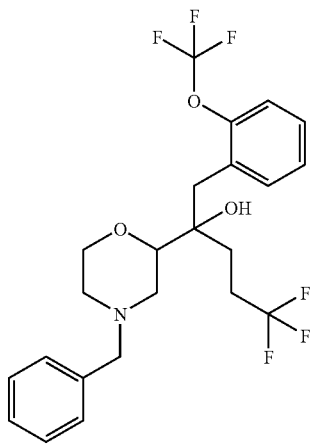

Compound 61 is obtained from 9 (0.7 g, 2.32 mmol) and commercially available (Fluorochem) 2-trifluoromethoxy benzyl magnesium bromide (5.12 mL, 2.56 mmol, 1.1 eq) in dry THF (15 mL) following General Procedure 2. Purification by ion exchange chromatography followed by automated column chromatography eluent, n-heptane/EtOAc 100/0 to 50/50 [v/v]) gives 61 as an oil (0.27 g, 25%). MW 477.45; $C_{23}H_{25}F_6NO_3$; LCMS (6 minute method): m/z 478.4 [M+H]$^+$, $R_T$ 3.63 ml.

5,5,5-Trifluoro-2-morpholin-2-yl-1-{2[(-trifluoromethyl)oxy]phenyl}pentan-2-ol hydrochloride (62)

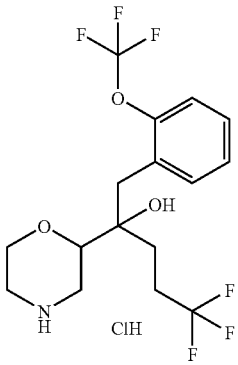

The free base of 62 is obtained from 61 (0.25 g, 0.53 mmol), α-chloroethyl chloroformate (0.23 mL, 2.12 mmol, 4 eq) and polymer-supported Hünig's base (0.30 g, 1.06 mmol, 2 eq) in DCM (5 mL) following General Procedure 3. Purification by ion exchange chromatography followed by preparative LCMS and conversion to its hydrochloride salt gives 62 as a yellow solid (0.051 g, 23%). MW 423.78; $C_{16}H_{19}F_6NO_3$·HCl; $^1H$ NMR ($CD_3OD$): δ 7.40-7.42 (1H, m), 7.19-7.30 (3H, m), 4.09-4.13 (1H, m), 3.71-3.78 (1H, m), 3.50-3.53 (1H, m), 3.36-3.40 (1H, m), 3.08-3.22 (3H, m), 2.89 (2H, 14 Hz), 2.09-2.17 (2H, m), 1.65-1.75 (1H, m), 1.30-1.40 (1H, m); LCMS (12 minute method): m/z 388.1 [M−HCl+H]$^+$, R$_T$ 4.99 min.

Example 27

Preparation of 1-[1,1'-biphenyl]-2-yl-5,5,5-trifluoro-2-morpholin-2-ylpentan-2-ol hydrochloride (64)

1-[1,1'-Biphenyl]-2-yl-5,5,5-trifluoro-2-[4-(phenylmethyl)morpholin-2-yl]pentan-2-ol (63)

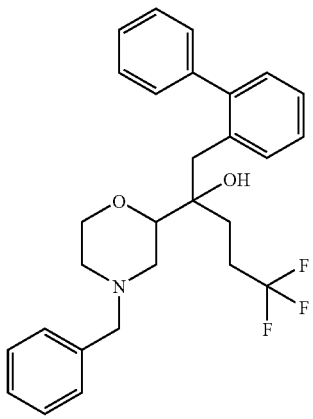

Compound 63 is obtained from 9 (0.7 g, 2.32 mmol) and 2-phenylbenzyl magnesium bromide (10.2 mL, 2.55 mmol, 1.1 eq) in dry THF (15 mL) following General Procedure 2. 2-Phenylbenzyl magnesium bromide is prepared from commercially available (Aldrich) 2-phenylbenzyl bromide following General Procedure 5. Purification by ion exchange chromatography followed by automated column chromatography (eluent, exane/EtOAc 100/0 to 70/30 [v/v]) gives 63 as an oil (604 mg, 60% purity). MW 469.55; $C_{28}H_{30}F_3NO_2$; LCMS (6 minute method): m/z 470.4 [M+H]$^+$, R$_T$ 3.77 min.

1-[1,1'-Biphenyl]-2-yl-5,5,5-trifluoro-2-morpholin-2-ylpentan-2-ol hydrochloride (64)

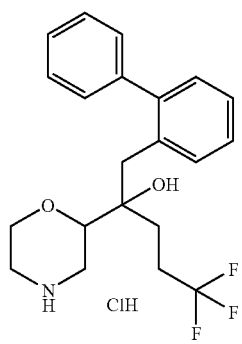

The free base of 64 is obtained from 63 (0.6 g, 1.29 mmol), α-chloroethyl chloroformate (0.56 mL, 5.15 mmol, 4 eq) and polymer-supported Hünig's base (0.72 g, 2.58 mmol, 2 eq) in DCM (12 mL) following General Procedure 3. Purification by ion exchange followed by preparative LCMS and conversion to the hydrochloride salt following General Procedure 4 gives 64 as a yellow solid (0.16 g, 30%). MW 415.89; $C_{21}H_{24}F_3NO_2$·HCl; $^1$H NMR (CD$_3$OD) δ 7.43-7.46 (1H, m), 7.18-7.35 (7H, m), 7.10-7.13 (1H, m), 3.90-3.95 (1H, m), 3.57-3.65 (1H, m), 3.34-3.38 (1H, m), 2.92 (2H, 14.5 Hz), 2.88-3.13 (4H, m), 1.59-1.85 (2H, m), 1.15-1.39 (2H, m); LCMS (12 minute method): m/z 380.1 [M−HCl+H]$^+$, R$_T$ 5.22 min.

Example 28

Preparation of 6,6,6-trifluoro-1-[5-fluoro-2-(methyloxy)phenyl]-2-morphol-2-ylhexan-2-ol hydrochloride (66)

6,6,6-Trifluoro-1-[5-fluoro-2-(methyloxy)phenyl]-2-[4-phenylmethyl)morpholin-2-yl]hexan-2-ol (65)

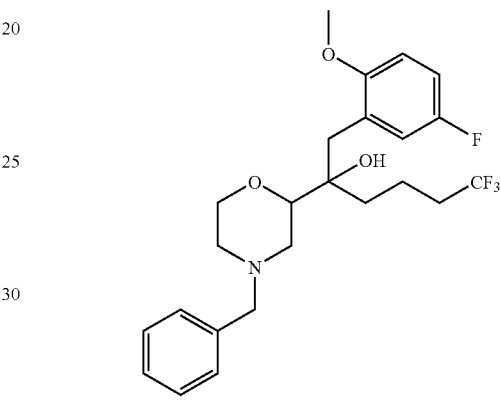

Compound 65 is obtained from 10 (0.6 g, 1.90 mmol) and 2-methoxy-5-fluorobenzyl magnesium bromide (4.2 mL, 2.09 mmol, 1.1 eq) in anhydrous THF (15 mL) following General Procedure 2 (further 2-methoxy-5-fluorobenzyl magnesium bromide is added (3.8 mL, 1.90 mmol)). Purification by ion exchange chromatography gives 65 in 87% purity as an oil which is directly used in the next step (0.7 g of recovered material). MW 455.50; $C_{24}H_{32}FNO_3$; LCMS (6 minute method) m/z 456.2 [+H]$^+$, R$_T$ 3.5 6 min.

6,6,6-Trifluoro-1-[5-fluoro-2-(methyloxy)phenyl]-2-morphol-2-ylhexan-2-ol hydrochloride (66)

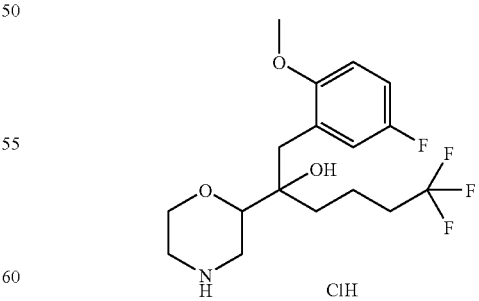

The free base of 66 is obtained from 65 (0.7 g, 1.53 mmol), α-chloroethyl chloroformate (0.66 mL, 6.1 mmol, 4 eq) and polymer-supported Hünig's base (0.86 g, 3.05 mmol, 2 eq) in DCM (13 mL) following General Procedure 3. Purification by ion exchange chromatography followed by automated column chromatography (eMeOH/DCM 0/100 to 20/80 [v/v]) and conversion to the hydrochloride salt gives 66 (0.19 g, 40%) as a white solid. MW 401.83; $C_{17}H_{23}F_4NO_3.HCl$; $^1H$ NMR (CD$_3$OD) δ 7.04-7.08 (1H, m), 6.95-6.97 (2H, m), 4.21 (1H, dd, 3.0 Hz, 13.0 Hz), 3.78-3.87 (4H, m), 3.63 (1H, dd, 2.0 Hz, 11.0 Hz), 3.45-3.49 (1H, m), 3.27-3.33 (1H, m), 3.12-3.21 (2H, m), 2.97 (2H, 14.0 Hz), 1.97-2.13 (2H,m), 1.61-1.76 (2H, m), 1.48-1.58 (1H, m), 1.17-1.31 (1H, m); LCMS (12 minute method): m/z 366.1 [M−HCl+H]$^+$, $R_T$ 4.72 min.

Example 29

Preparation of 1-[1,1'-biphenyl]-2-yl-6,6,6-trifluoro-2-morpholin-2-yl]hexan-2-ol hydrochloride (68)

1-[1,1'-Biphenyl]-2-yl-6,6,6-trifluoro-2-[4-(phenylmethyl)morpholin-2-yl]hexan-2-ol (67)

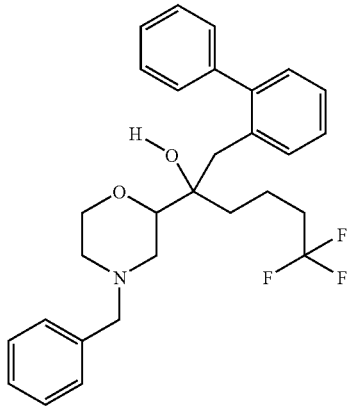

Compound 67 is prepared from 10 (0.853 g, 2.71 mmol) and 2-phenyl benzyl magnesium bromide (0.25 M solution in diethyl ether, 1.2 eq) following General Procedure 2. 2-Phenylbenzyl magnesium bromide is prepared from commercially available (Aldrich) 2-phenylbenzyl bromide following General Procedure 5. Further 2-phenyl benzyl magnesium bromide is added later (19.2 mL, 4.8 mmol). Purification by automated column chromatography (eluent, EtOAc/cyclohexane 20/80 to 40/60 [v/v]), followed by ion exchange chromatography gives 67 as a viscous oil (369 mg, 28%). MW 483.58; $C_{29}H_{32}F_3NO_2$; LCMS: (6 min method) m/z 484 [M+H]$^+$, $R_T$ 4.26 min.

1-[1,1'-Biphenyl]-2-yl-6,6,6-trifluoro-2-morpholin-2-yl]hexan-2-ol hydrochloride (68)

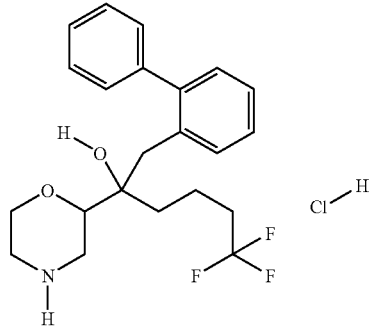

The free base of 68 is obtained from 10 (0.369 g, 0.76 mmol), solid supported Hünig's base (0.43 g) and α-chloroethyl chloroformate (0.32 mL) in anhydrous DCM (10 mL) following General Procedure 3. Purification by ion exchange chromatography gives the free base of 68 as a viscous oil (0.143 g, 48%) which is converted into the hydrochloride salt 68 following General Procedure 4. MW 429.91; $C_{22}H_{26}NO_2F_3$ HCl; $^1H$ NMR (CD$_3$OD): 7.44-7.47 (1H, m), δ 7.16-7.35 (7H, m), 7.08-7.11 (1H, m), 3.94 (1H, dd, 12.5 Hz, 3.5 Hz,), 3.57 (1H, t, 12.5 Hz), 3.34-3.38 (1H, m), 2.80-3.11 (6H, m), 1.65-3.90 (2H, m), 1.02-1.24 (4H, m). LCMS: (12 minute method) m/z 394 [M−HCl+H]$^+$, $R_T$ 5.42 min.

Example 30

Preparation of 1-Cyclopropyl-2-[2-(methyloxy)phenyl]-1-morpholin-2-ylethanol hydrochloride (70)

1-Cyclopropyl-2-[2-(methyloxy)phenyl]-1-[4-(phenylmethyl)morpholin-2-yl]ethanol (69)

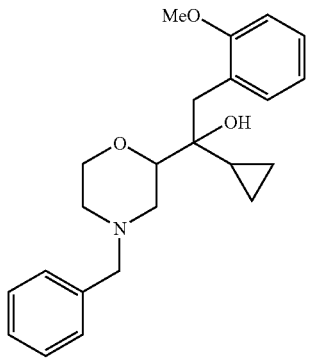

Compound 69 is obtained from 77 (0.5 g, 2.04 mmol) and 2-methoxybenzyl magnesium bromide (available from Rieke Metals) (0.25M solution in THF, 9.0 mL, 2.24 mmol, 1.1 eq.) in anhydrous THF (11 mL) following General Procedure 1. Further 2-methoxybenzyl magnesium bromide (0.25M solution in THF, 4.08 mL, 1.04 mmol, 0.5 eq) is added after 10 minutes. Purification by ion exchange chromatography gives 69 which is directly used in the next step (0.706 g, 94%, >90% purity). MW 367.49; $C_{23}H_{29}NO_3$; LCMS (6 minute method): m/z 368 [M+H]$^+$, $R_T$ 2.52 min.

1-Cyclopropyl-2-[-2-(methyloxy)phenyl]-1-morpholin-2-ylethanol hydrochloride (70)

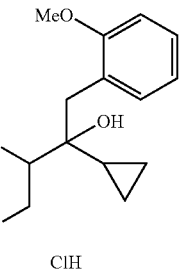

The free base of 70 is obtained from 69 (0.706 g, 1.92 mmol), α-chloroethyl chloroformate (0.83 mL, 7.69 mmol, 4 eq) and polymer-supported Hünig's base (1.08 g, 3.85 mmol, 2 eq) in DCM (25 mL) following General Procedure 3. Purification by ion exchange ion exchange chromatography followed by automated column chromatography (eluent, DCM/MeOH, 90/10 to 50/-50 [v/v]) gives the free base of 70 (0.29 g, 55%). A sample (0.06 g, 0.22 mmol) is converted into the hydrochloride salt 70 following General Procedure 4 (63 mg, 99%). MW 313.83; $C_{16}H_{23}NO_3.HCl$. $^1H$ NMR (CD$_3$OD): δ 6.95-7.15 (2H, m), 6.60-6.85 (2H, m), 3.95 (1H, dd, 2 Hz, 10 Hz), 3.55-3.7 (2H, m), 3.15-3.4 (2H, m), 3.05 (3H, s), 2.7-

3.95 (5H, m), 0.4-0.55 (1H, m), 0.15-0.3 (1H, m), −0.1-0.1 (3H, m); LCMS (12 minute method): m/z 278.1 [M−HCl+H]⁺, R_T 3.81 min.

Example 31

Preparation of 1-Cyclopropyl-2-[2-(ethyloxy)phenyl]-1-morpholin-2-ylethanol hydrochloride (72)

1-Cyclopropyl-2-[2-(ethyloxy)phenyl]-1-[4-phenylmethyl)morpholin-2-yl]ethanol (71)

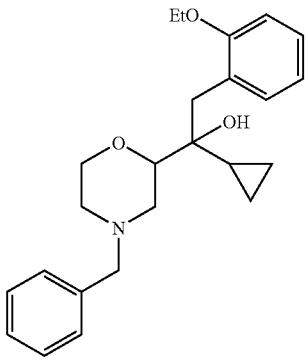

Compound 71 is obtained from 77 (0.36 g, 1.47 mmol) and 2-ethoxybenzyl magnesium bromide (available from Rieke Metals) (0.25M solution in THF, 6.47 mL, 1.61 mmol, 1.1 eq) in anhydrous THF (8 mL) following General Procedure 1. Further 2-ethoxybenzyl magnesium bromide (0.25M solution in THF, 3.23 mL, 0.8 mmol, 0.5 eq) is added after 30 minutes. Purification by ion exchange chromatography (eluent, EtOAc/n-heptane 0/100 to 40/60 [v/v]) gives 71. MW 381.52; $C_{24}H_{31}NO_3$; LCMS (6 minute method): m/z 382.4 [M+H]⁺, R_T 2.83 min.

1-Cyclopropyl-2-[2-(ethyloxy)phenyl]-1-morpholin-2-ylethanol hydrochloride (72)

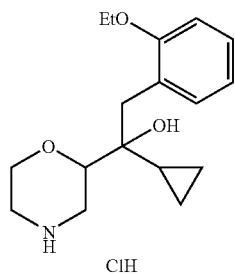

The free base of 72 is obtained from 71 (0.62 g, 1.62 mmol), α-chloroethyl chloroformate (0.93 g, 0.7 mL, 6.49 mmol, 4 eq) and polymer-supported Hünig's base (0.91 g, 3.24 mmol, 2 eq) in DCM (20 mL) following General Procedure 3. Purification by ion exchange chromatography followed by automated column chromatography (eluent, DCM/MeOH 90/10 to 50/-50 [v/v]) gives the free base of 72 as an oil (0.32 g, 68%) in 89% purity. Conversion into the hydrochloride salt following General Procedure 4 gives 72. MW 327.85; $C_{17}H_{25}NO_3 \cdot HCl$; ¹H NMR (CD₃OD); δ 6.9-7.05 (2H, m), 6.60-6.8 (2H, m), 4.05 (1H, dd, 2 Hz, 10 Hz), 3.7-3.85 (2H, m), 3.6 (1H, dt, 2 Hz, 7 Hz), 3.15-3.45 (2H, m), 2.8-2.95 (5H, m), 1.15 (3H, t, 7 Hz), 0.4-0.55 (1H, m), 0.15-0.3 (1H, m), −0.1-0.1 (3H, m). LCMS (12 minute method): m/z 292.1 [M−HCl+H]⁺, R_T 4.44 min.

Example 32

Preparation of 2-[1,1'-biphenyl]-2-yl-1-cyclopropyl-1-morpholin-2-ylethanol hydrochloride (74)

2-[1,1'-Biphenyl]-2-yl-1-cyclopropyl-1-[4-(phenylmethyl)morpholin-2-yl]ethanol (73)

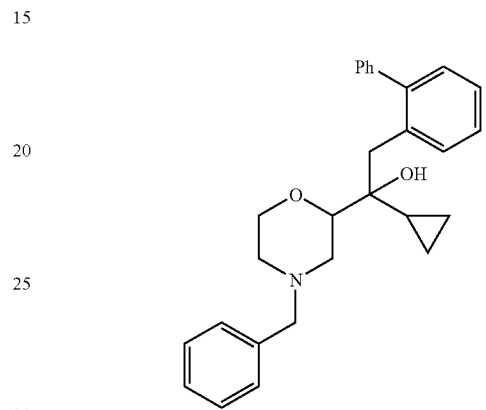

Compound 73 is obtained from 77 (0.7 g, 2.86 mmol) and 2-phenylbenzyl magnesium bromide (0.25M solution in THF, 12.58 mL, 3.15 mmol, 1.1 eq) in anhydrous THF (15 mL) following General Procedure 1. 2-Phenylbenzyl magnesium bromide is prepared from commercially available (Aldrich) 2-phenylbenzyl bromide following General Procedure 5. Further 2-phenylbenzyl magnesium bromide (0.25M solution in THF, 6.3 mL, 1.65 mmol, 0.5 eq.) is added after 30 minutes. Purification by ion exchange chromatography gives 73 as a gum (1.07 g, 91%). MW 413.56; $C_{28}H_{31}NO_2$; LCMS (6 minute method): m/z 414.4 [M+H]⁺, R_T 3.11 min.

2-[1,1'-biphenyl]-2-yl-1-cyclopropyl-1-morpholin-2-ylethanol (74)

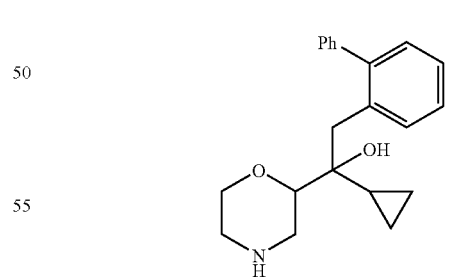

The free base of 74 is obtained from 73 (1.06 g, 2.57 mmol), α-chloroethyl chloroformate (1.11 mL, 10.3 mmol, 4 eq) and polymer-supported Hünig's base (1.44 g, 5.13 mmol, 2 eq) in DCM (30 mL) following General Procedure 3. Purification by ion exchange chromatography followed by automated column chromatography gives the free base of 74 (0.54 g, 65%) which is converted into the hydrochloride salt 74 following General Procedure 4. MW 323.44; $C_{21}H_{25}NO_2$. ¹H NMR (CDCl₃) $\delta_H$ 7.46-7.53 (1H, m), 7.30-7.44 (5H, m), 7.18-7.30 (3H, m), 3.72-7.82 (1H, m), 3.33-3.51 (2H,m), 3.07-3.20 (3H,m), 2.56-2.80 (4H, m), 0.25-0.39 (2H, m), 0.07-0.19 (1H, m), −0.09-0.03 (1H,m), −0.28--0.16 (1H, m). LCMS (12 minute method): m/z 324.2 [M+H]⁺, $R_T$ 4.96 min.

Example 33

Preparation of 1,3-Bis-(2-methoxy-phenyl)-2-morpholin-2-yl-propan-2-ol hydrochloride (79)

2-(4-benzyl-morpholin-2-yl)-1,3-bis-(2-methoxyphenyl)-propan-2-ol (78)

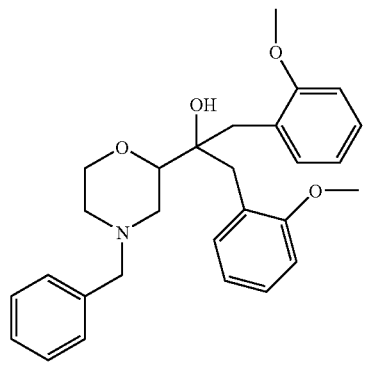

Add a solution of 4-benzyl-morpholine-2-carboxylic acid ethyl ester (1.12 g, 4.49 mmol) in tetrahydrofuran (5 mL) to a stirred solution of 2-methoxybenzylmagnesium chloride (54 mL, 0.25M solution in tetrahydrofuran, commercially available from Rieke Metals) at −10° C. under nitrogen atmosphere. After 1 hour, add a saturated aqueous solution of sodium bicarbonate and extract with diethyl ether. Combine the organic layers and extract with brine, dry over magnesium sulfate, filter, and concentrate under reduced pressure to give a residue to be taken forward without further purification. MW 447.58; $C_{28}H_{33}NO_4$; LCMS (12 minute method):m/z)= 448.2 [M+H]+) $R_T$ 4.8 min.

1,3-Bis-(2-methoxy-phenyl)-2-morpholin-2-yl-propan-2-ol hydrochloride (79)

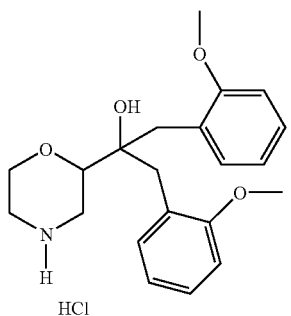

To a solution of 78 (2.2 g, 5 mmol) in EtOH (30 mL) under nitrogen atmosphere add ammonium formate (3.1 g, 50 mmol) followed by palladium on charcoal (10%, 2.2 g). Stir and heat at reflux the resulting suspension for an hour. Allow the reaction mixture to cool to room temperature and then filter it through Celite®. Wash the Celite® with copious amounts of ethanol, combine the organic layers and concentrate under reduced pressure to obtain a residue. Purify and resolve the residue by Chiral HPLC to give 79; MW 393.91; $C_{21}H_{27}NO_4$.HCl; ¹H NMR (DMSO-D₆): δ 2.41-2.52 (m, 1H), 2.61-2.78 (m, 1H), 2.85-3.44 (m, 8H), 3.50-3.65 (m, 1H), 3.7 (s, 3H), 3.79 (s, 3H), 4.00-4.12 (m, 1H), 6.79-7.01 (m, 4H), 7.07-7.25 (m, 3H), 7.26-7.35 (m, 1H); LCMS (12 minute method): m/z 358.1 [M−HCl+H]) $R_T$ 4.6 min single major peak;

Example 34

Preparation of 1-(2-Methoxy-benzyl)-2-(2-methoxyphenyl)-1-morpholin-2-yl-ethylamine dihydrochloride 1-(4-Benzyl-morpholin-2-yl)-1-(2-methoxy-benzyl)-2-(2-methoxy-phenyl)-ethylamine diacetate (80)

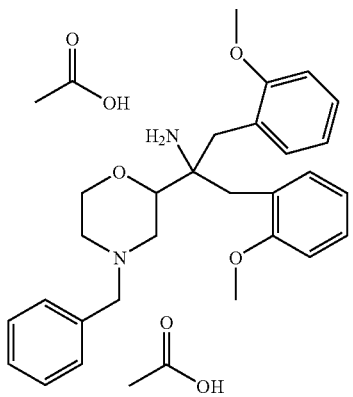

To a solution of 4-benzyl-morpholine-2-carbonitrile (10 g, 49.5 mmol) in dry diethyl ether (100 mL) at −10° C. under an atmosphere of nitrogen is added a solution of 2-methoxybenzylmagnesium chloride (0.25M solution in tetrahydrofuran, 218 mL, 54.5 mmol) available from Aldrich Chemical Company or Rieke Metals) and the reaction mixture is further stirred at −10° C. for 30 minutes. Then the reaction is allowed to warm to room temperature and stirred overnight The reaction is then cooled to 0° C. and quenched by addition of hydrochloric acid (5N aqueous solution, 50 mL) and the resulting mixture is stirred for 10 minutes at 0° C. Next the solution is basified with sodium hydroxide (2N aqueous solution), filtered through Celite® then extracted with diethyl ether, the organics collected, dried (MgSO₄) and the solvent removed under reduced pressure to give a residue which is taken up into methanol and purified by SCX-2 chromatography prior to silica gel chromatography (eluent, ethyl acetate/ n-hexane, 0/100 to 40/60 [v/v]). The fractions containing the correct mass (FIA⁺[M+H]+=447) are collected and purified via preparative HPLC to give 80 (72 mg). MW 566.69; $C_{28}H_{34}N_2O_3.C_4H_8O_4$; LCMS (12 minutes method): m/z)=447.2 [M−$C_4H_8O_4$+H]+ $R_T$ 4.60 min.

85

1-(2-Methoxy-benzyl)-2-(2-methoxy-phenyl)-1-morpholin-2-yl-ethylamine dihydrochloride (81)

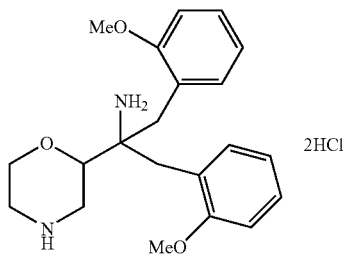

To a methanolic solution of 80 (70 mg, 0.13 mmol) is added ammonium formate (100 mg, 1.6 mmol) and 10% Pd—C (150 mg). The reaction is stirred under nitrogen and heated at reflux for 30 minutes then cooled and filtered through Celite®. The filtrate is concentrated in vacuo and the residue is taken up in methanol and purified by SCX-2 ® ion exchange resin and the resulting residue redissolved in a 2M hydrochloric acid in diethyl ether solution and then concentrated in vacuo to give 81 (1.7 mg, 0.3%). MW 429.39; $C_{21}H_{28}N_2O_3 \cdot 2HCl$; $^1H$ NMR ($CD_3OD$): δ 2.65-3.02 (m, 6H), 3.05-3.16 (m, 1H), 3.24-3.41 (m, 2H), 3.52-3.65 (m, 1H), 3.70 (s, 3H), 3.80 (s, 3H), 3.91-4.05 (m, 1H), 6.84-7.08 (m, 4H), 7.12-7.32 (m, 4H). LCMS (12 minute method) m/z 357.2 $[M-2\times HCl+H^+]^+ R_T$ 2.07 min.

Example 35

Preparation of 1-(2-Methoxy-phenyl)-2-morpholin-2-yl-hexan-2-ol hydrochloride (84)

2-(4-Benzyl-morpholin-2-yl)-1-(2-methoxy-phenyl)-hexan-2-ol (83)

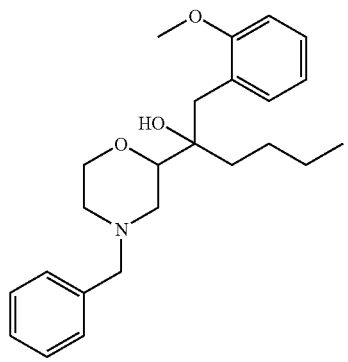

Compound 83 is obtained from 82 (0.21 g, 0.81 mmol) and 2-phenyl-benzyl magnesium bromide (4.9 mL, 1.21 mmol, 1.5 eq) in anhydrous THF (10 mL) following General Procedure 2 and left stinging for 50 minutes. Purification by ion exchange chromatography gives 83 (0.16 g crude) which was directly used in the next step. MW 383.54; $C_{24}H_{33}NO_3$; LCMS (6 minute method): m/z 384.4 $[M+H]^+$, $R_T$ 3.05 min.

86

1-(2-Methoxy-phenyl)-2-morpholin-2-yl-hexan-2-ol hydrochloride salt (84)

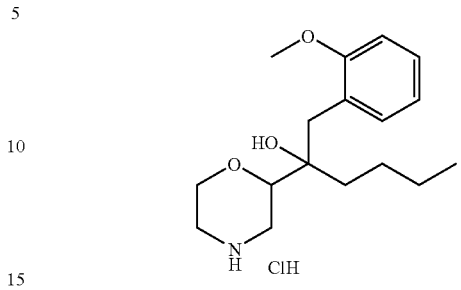

The free base of 84 is obtained from 83 (0.23 g, 0.61 mmol), α-chloroethyl chloroformate (0.17 mg, 1.21 mmol) and polymer-supported Hünig's base (0.47 g, 1.82 mmol, 3 eq) in DCM (10 mL) following General Procedure 3. Purification by ion exchange followed by preparative LCMS and conversion to the hydrochloride salt following General Procedure 4 gives 84 as a yellow solid (0.1 g, 6%). MW 329.87; $C_{17}H_{27}NO_3 \cdot HCl$; $^1H$ NMR ($CD_3OD$): δ 6.74-6.66 (m, 2H), 6.46-6.33 (m, 2H), 3.69-3.61 (m, 1E), 3.32-3.24 (m, 2H), 3.14-3.07 ($m_n$, 1H), 2.92-2.84 (m, 1H), 2.83-2.69 (n, 3H), 2.67-2.56 (m, 2H), 2.50-2.39 (m, 2H), 1.00-0.58 (m, 6H), 0.41-0.32 (m, 3H); LCMS (12 minute method): m/z 294.2 $[M-HCl+H]+$ and 316.2 $[M-HCl+Na]^+$, $R_T$ 4.158 min.

Example 36

Preparation of 2-Morpholinyl-1-biphenyl-2-yl-hexan-2-ol hydrochloride (86)

2-(4-Benzyl-morpholin-2-yl)-1-biphenyl-2-yl-hexan-2-ol (85)

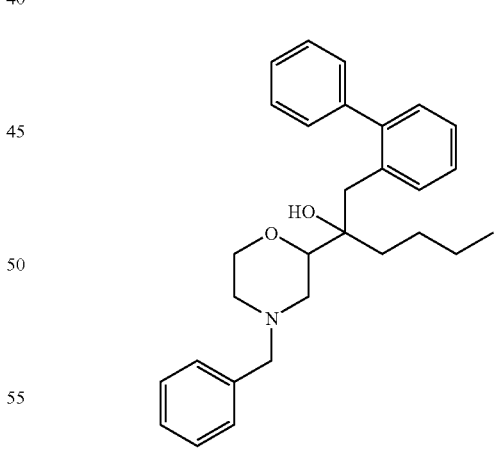

Compound 85 is obtained from 82 (0.21 g, 0.81 mmol) and 2-phenyl-benzyl magnesium bromide (4.9 mL, 1.225 mmol, 1.5 eq) in anhydrous THF (10 mL) following General Procedure 2. Further equivalents of 2-phenyl-benzyl magnesium bromide (20 mL, 5.0 mmol) are added and the mixture is left stirring for two hours. Purification by ion exchange chromatography gives 85 (0.16 g crude) which was directly used in the next step. MW 429.61; $C_{25}H_{35}NO_2$; LCMS (6 minute method): m/z 430, $[M+H]^+$, $R_T$ 3.46 min.

87

2-Morpholinyl-1-biphenyl-2-yl-hexan-2-ol hydrochloride (86)

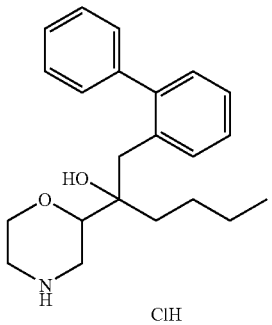

The free base of 86 is obtained from 85 (0.16 g, crude), α-chloroethyl chloroformate (0.1 mL, 0.77 mmol, excess) and polymer-supported Hünig's base (1.15 mmol, excess) in DCM (12 mL) following General Procedure 3. Purification by ion exchange followed by preparative LCMS and conversion to the hydrochloride salt following General Procedure 4 gives 86 as a yellow solid (16 mg, 5% over steps). MW 375.94; $C_{22}H_{29}NO_2 \cdot HCl$; $^1H$ NMR ($CD_3OD$): δ 7.90-7.35 (m, 9H), 4.30 (d, 1H, 10.5 Hz), 4.00-3.90 (t, 1H, 12 Hz), 3.72 (d, 1H, 10.5 Hz), 3.55 (bs, 2H), 3.44 (d, 2H, 11.5 Hz), 3.35-3.15 (m, 4H), 1.50-0.9 (m, 9H); LCMS (12 minute method): m/z 340.3 $[M-HCl+H]^+$, $R_T$ 5.1 min.

Example 37

1-(2-Chloro-6-fluoro-phenyl)-4-methyl-2-morpholin-2-yl-pentan-2-ol hydrochloride salt (88)

2-(4-Benzyl-morpholin-2-yl)-1-(2-chloro-6-fluoro-phenyl)-4-methyl-pentan-2-ol (87)

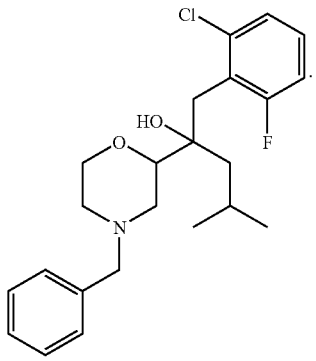

Compound 87 is obtained from 6 (0.33 g, 1.28 mmol) and 2-chloro-6-fluoro-benzyl magnesium bromide (8 mL, 1.92 mmol, 1.5 eq) in anhydrous THF (15 mL) following General Procedure 2. Further equivalents of 2-chloro-6-fluoro-benzyl magnesium bromide (20 mL, 3.75 eq) are added and the mixture is left stirring over night. Purification by ion exchange chromatography gives 87 (0.52 g, 99%) as a mixture of two diastereomers (approximately 6:1 ratio). MW 405.94; $C_{23}H_{29}ClFNO_2$; LCMS (6 minute method): m/z 406.2 $[M+H]^+$, $R_T$ 3.31 and 3.39 min.

88

1-(2-Chloro-6-fluoro-phenyl)-4-methyl-2-morpholin-2-yl-pentan-2-ol hydrochloride salt (88)

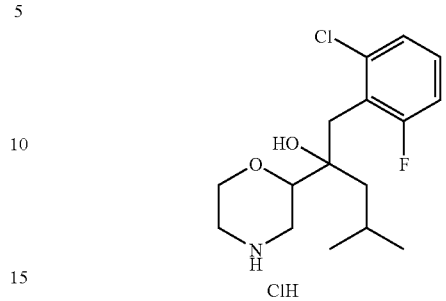

The free base of 88 is obtained from 87 (0.52 g, 1.27 mmol), α-chloroethyl chloroformate (0.28 mL, 2.54 mmol, 2 eq) and polymer-supported Hünig's base (3.81 mmol, 0.98 g) in DCM (15 mL) following General Procedure 3. Purification by ion exchange and UV-guided preparative and chiral chromatography followed by conversion of the major diastereomer to the hydrochloride salt following General Procedure 4 gives 88 (0.145 g, 32%). MW 352.27; $C_{16}H_{23}ClFNO_2 \cdot HCl$; $^1H$ NMR ($CD_3OD$): δ 7.27-7.18 (m, 2H), 7.09-6.99 (m, 1H), 4.15-4.04 (m, 1H), 3.89-3.73 (m, 2H), 3.60-3.50 (m, 1H), 3.35-3.00 (m, 5H), 1.88-1.69 (m, 2H), 1.32-1.15 (m, 1H), 0.97-0.86 (m, 6H); LCMS (12 minute method): m/z 298.1 $[M-HCl-H_2O+H]^+$ and 316.2 $[M-HCl+H]^+$, $R_T$ 4.328 min.

Example 38

1-(2-Chloro-phenyl)-4-methyl-2-morpholin-2-yl-Pentan-2-ol hydrochloride salt (90)

2-(4-Benzyl-morpholin-2-yl)-1-(2-chloro-phenyl)-4-methyl-pentan-2-ol (89)

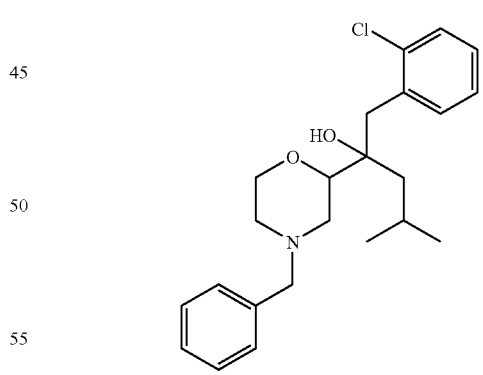

Compound 89 is obtained from 6 (0.33 g, 1.28 mmol) and 2-chloro-benzyl magnesium bromide (8 mL, 1.92 mmol, 1.5 eq) in anhydrous THF (15 mL) following General Procedure 2. Further equivalents of 2-chloro-benzyl magnesium bromide (20 mL, 3.75 eq) are added and the mixture is left stirring over night. Purification by ion exchange chromatography gives 89 (0.598 g crude) which was directly used in the next step. MW 387.95; $C_{23}H_{30}ClNO_2$; LCMS (6 minute method): m/z 388.2 $[M+H]^+$, $R_T$ 3.13 min.

1-(2-Chloro-phenyl)-4-methyl-2-morpholin-2-yl-pentan-2-ol hydrochloride salt (90)

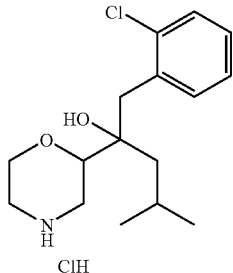

The free base of 90 is obtained from 89 (0.598 g, 1.27 mmol), α-chloroethyl chloroformate (0.31 mL, 2.82 mmol, 2.2 eq) and polymer-supported Hünig's base (4.23 mmol, 1.1 g) in DCM (15 mL) following General Procedure 3. Purification by ion exchange and UV-guided preparative and chiral chromatography followed by conversion of the major diastereomer to the hydrochloride salt following General Procedure 4 gives 90 (0.083 g, 19% over two steps). MW 334.29; $C_{16}H_{24}ClNO_2 \cdot HCl$; $^1H$ NMR (CD$_3$OD): δ 7.51-7.44 (m, 1H), 7.39-7.31 (m, 1H), 7.26-7.14 (m, 2H) 4.13 (d, 1H, 9 Hz), 3.87-3.69 (m, 2H), 3.47 (d, 1H, 9 Hz), 3.38-3.03 (m, 4H), 2.99-2.88 (m, 1H), 1.87-1.74 (m, 1H), 1.67-1.57 (m, 1H), 1.20-1.09 (m, 1H), 0.95-0.83 (m, 6H); LCMS (12 minute method): m/z 280.2 [M−HCl−H$_2$O+H]+ and 298.2 [M−HCl+H], $R_T$ 4.314 min.

The pharmacological profile of the present compounds may be demonstrated as follows. All of the exemplified compounds above have been found to exhibit a $K_i$ value less than 1 μm at the norepinephrine transporter as determined using the scintillation proximity assay described below. Furthermore, all of the exemplified compounds above have been found to inhibit the norepinephrine transporter to a greater extent than the serotonin and dopamine transporters using the scintillation proximity assays as described below.

Generation of Stable Cell-Lines Expressing the Human Dopamine, Norepinephrine and Serotonin Transporters Standard molecular cloning techniques are used to generate stable cell-lines expressing the human dopamine, norepinephrine and serotonin transporters. The polymerase chain reaction (PCR) is used in order to isolate and amplify each of the three full-length cDNAs from an appropriate cDNA library. Primers for PCR are designed using the following published sequence data:

Human dopamine transporter: GenBank M95167. Reference: Vandenbergh D J, Persico A M and Uhl G R. A human dopamine transporter cDNA predicts reduced glycosylation, displays a novel repetitive element and provides racially-dimorphic TaqI RFLPs. Molecular Brain Research (1992) volume 15, pages 161-166.

Human norepinephrine transporter: GenBank M65105. Reference: Pacholczyk T, Blakely, R D and Amara S G. Expression cloning of a cocaine- and antidepressant-sensitive human noradrenaline transporter. Nature (1991) volume 350, pages 350-354.

Human serotonin transporter: GenBank L05568. Reference: Ramaroorthy S, Bauman A L, Moore K R, Han H, Yang-Feng T, Chang A S, Ganapathy V and Blakely R D. *Antidepressant- and cocaine-sensitive human serotonin transporter: Molecular cloning, expression, and chromosomal localization*. Proceedings of the National Academy of Sciences of the USA (1993) volume 90, pages 2542-2546.

The PCR products are cloned into a mammalian expression vector (eg pcDNA3.1 (Invitrogen)) using standard ligation techniques. The constructs are then used to stably transfect HEK293 cells using a commercially available lipofection reagent (Lipofectamine™—Invitrogen) following the manufacture's protocol.

Scintillation Proximity Assays for Determining the Affinity of Test Ligands at the Norepinephrine Transporter.

The compounds of the present invention are norepinephrine reuptake inhibitors, and possess excellent activity in, for example, a scintillation proximity assay (e.g. J. Gobel, D. L. Saussy and A. Goetz, J. Pharmacol. Toxicolo. (1999), 42, 237-244). Thus $^3H$-nisoxetine binding to norepinephrine reuptake sites in a cell line transfected with DNA encoding human norepinephrine transporter binding protein is used to determine the affinity of ligands at the norepinephrine transporter.

Membrane Preparation:

Cell pastes from large scale production of HEK-293 cells expressing cloned human norepinephrine transporters are homogenized in 4 volumes 50 mM Tris-HCl containing 300 mM NaCl and 5 mM KCl, pH 7.4. The homogenate is centrifuged twice (40,000 g, 10 min, 4° C.) with pellet re-suspension in 4 volumes of Tris-HCl buffer containing the above reagents after the first spin and 8 volumes after the second spin. The suspended homogenate is centrifuged (100 g, 10 min, 4° C.) and the supernatant kept and re-centrifuged (40,000 g, 20 min, 4° C.). The pellet is resuspended in Tris-HCl buffer containing the above reagents along with 10% w/v sucrose and 0.1 mM phenylmethylsulfonyl fluoride (PMSF). The membrane preparation is stored in aliquots (1 mL) at −80° C. until required. The protein concentration of the membrane preparation is determined using a bicinchoninic acid (BCA) protein assay reagent kit (available from Pierce).

[$^3H$]-Nisoxetine Binding Assay:

Each well of a 96 well microtitre plate is set up to contain the following:

| | |
|---|---|
| 50 μl | 2 nM [N-methyl-$^3H$]-Nisoxetine hydrochloride (70-87 Ci/mmol, from NEN Life Science Products) |
| 75 μl | Assay buffer (50 mM Tris-HCl pH 7.4 containing 300 mM NaCl and 5 mM KCl) |
| 25 μl | Test compound, assay buffer (total binding) or 10 μM Desipramine HCl (non-specific binding) |
| 50 μl | Wheatgerm agglutinin coated poly (vinyltoluene) (WGA PVT) SPA Beads (Amersham Biosciences RPNQ0001) (10 mg/mL) |
| 50 μl | Membrane (0.2 mg protein per mL) |

The microtitre plates are incubated at room temperature for 10 hours prior to reading in a Trilux scintillation counter. The results are analysed using an automatic spline fitting programme (Multicalc, Packard, Milton Keynes, UK) to provide Ki values for each of the test compounds.

Serotonin Binding Assay

The ability of a test compound to compete with [$^3H$]-citalopram for its binding sites on cloned human serotonin transporter containing membranes is used as a measure of test compound ability to block serotonin uptake via its specific transporter (Ramamoorthy, S., Giovanetti, E., Qian, Y., Blakely, R., (1998) J. Biol. Chem. 273, 2458).

Membrane Preparation:

Membrane preparation is essentially similar to that for the norepinephrine transporter containing membranes as described above. The membrane preparation is stored in aliquots (1 mL) at −70° C. until required. The protein concentration of the membrane preparation is determined using a BCA protein assay reagent kit.

[$^3$H]-Citalopram Binding Assay:

Each well of a 96 well microtitre plate is set up to contain the following:

| | |
|---|---|
| 50 μl | 2 nM [$^3$H]-Citalopram (60-86 Ci/mmol, Amersham Biosciences) |
| 75 μl | Assay buffer (50 mM Tris-HCl pH 7.4 containing 150 mM NaCl and 5 mM KCl) |
| 25 μl | Diluted compound, assay buffer (total binding) or 100 μM Fluoxetine (non-specific binding) |
| 50 μl | WGA PVT SPA Beads (40 mg/mL) |
| 50 μl | Membrane preparation (0.4 mg protein per mL) |

The microtitre plates are incubated at room temperature for 10 hours prior to reading in a Trilux scintillation counter. The results are analysed using an automatic spline fitting programme (Multicalc, Packard, Milton Keynes, UK) to provide Ki (nM) values for each of the test compounds.

Dopamine Binding Assay

The ability of a test compound to compete with [3H]-WIN35,428 for its binding sites on human cell membranes containing cloned human dopamine transporter has been used as a measure of the ability of such test compounds to block dopamine uptake via its specific transporter (Ramamoorthy et al 1998 supra).

Membrane Preparation:

Is essentially the same as for membranes containing cloned human serotonin transporter as described above.

[3H]-WIN35,428 Binding Assay:

Each well of a 96 well microtitre plate is set up to contain the following:

| | |
|---|---|
| 50 μl | 4 nM [$^3$H]-WIN35,428 (84-87 Ci/mmol, from NEN Life Science Products) |
| 75 μl | Assay buffer (50 mM Tris-HCl pH 7.4 containing 150 mM NaCl and 5 mM KCl) |
| 25 μl | Diluted compound, assay buffer (total binding) or 100 μM Nomifensine (non-specific binding) |
| 50 μl | WGA PVT SPA Beads (10 mg/mL) |
| 50 μl | Membrane preparation (0.2 mg protein per mL). |

The microtitre plates are incubated at room temperature for 120 minutes prior to reading in a Trilux scintillation counter. The results are analysed using an automatic spline fitting programme (Multicalc, Packard, Milton Keynes, UK) to provide Ki values for test compounds.

Acid Stability

The acid stability of a compound according to the present invention may be determined as a solution in buffer at 6 different pH values (HCl 0.1N, pH 2, pH 4, pH 6, pH 7, and pH 8) at 40° C. over a time course of 72 hours. Samples may be taken at the beginning of the study and after 3, 6 and 24 hours and analysed by capillary electrophoresis. The original sample used in the study may contain 0.8% of the undesired epimer as internal standard. If the tested compound is chemically and configurationally stable under acidic conditions the samples taken at the different time points during the study should not show any significant change in the percentage of the undesired epimer.

In Vitro Determination of the Interaction of Compounds with CYP2D6 in Human Hepatic Microsomes Cytochrome P450 2D6 (CYP2D6) is a mammalian enzyme which is commonly associated with the metabolism of around 30% of pharmaceutical compounds. Moreover, this enzyme exhibits genetic polymorphism, resulting in the presence of both normal and poor metabolizers in the population. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) are acquired from Human Biologics (Scottsdale, Ariz., USA). Quinidine and β-NADPH (β-Nicotinamide Adenine Dinucleotide Phosphate, reduced form, tetrasodium salt) are purchased from Sigma (St Louis, Mo., USA). All the other reagents and solvents are of analytical grade. A stock solution of the new chemical entity (NCE) is prepared in a mixture of Acetonitrile/Water to reach a final concentration of acetonitrile in the incubation below 0.5%.

The microsomal incubation mixture (total volume 0.1 mL) contains the NCE (4 μM), β-NADPH (1 mM, microsomal proteins (0.5 mg/mL), and Quinidine (0 or 2 μM) in 100 mM sodium phosphate buffer pH 7.4. The mixture is incubated for 30 minutes at 37° C. in a shaking waterbath. The reaction is terminated by the addition of acetonitrile (75 μL). The samples are vortexed and the denaturated proteins are removed by centrifugation. The amount of NCE in the supernatant is analyzed by liquid chromatography/mass spectrometry (LC/MS) after addition of an internal standard. A sample is also taken at the start of the incubation (t=0), and analysed similarly.

Analysis of the NCE is performed by liquid chromatography/mass spectrometry. Ten μL of diluted samples (20 fold dilution in the mobile phase) are injected onto a Spherisorb CN Column, 5 μM and 2.1 mm×100 mm (Waters corp. Milford, Mass., USA). The mobile phase consisting of a mixture of Solvent A/Solvent B, 3070 (v/v) is pumped (Alliance 2795, Waters corp. Milford, Mass., USA) through the column at a flow rate of 0.2 mL/minute. Solvent A and Solvent B are a mixture of ammonium formate $5.10^{-3}$ M pH 4.5/methanol in the proportions 95/5 (v/v) and 10/90 (v/v), for solvent A and solvent B, respectively. The NCE and the internal standard are quantified by monitoring their molecular ion using a mass spectrometer ZMD or ZQ (Waters-Micromass corp, Machester, UK) operated in a positive electrospray ionisation.

The extent of CYP2D6 involvement (% of CYP2D6 involvement) is calculated comparing the extent of metabolism in absence and in presence of quinidine in the incubation.

The extent of metabolism without inhibitor (%) is calculated as follows:

$$\frac{(NCE \text{ response in samples without inhibitor) time 0} - (NCE \text{ response in samples without inhibitor) time 30}}{(NCE \text{ response in samples without inhibitor) time 0}} \times 100$$

The extent of metabolism with inhibitor (%) is calculated as follows:

$$\frac{(NCE \text{ response in samples without inhibitor) time 0} - (NCE \text{ response in samples without inhibitor) time 30}}{(NCE \text{ response in samples without inhibitor) time 0}} \times 100$$

where the NCE response is the area of the NCE divided by the area of the internal standard in the LC/MS analysis chromatogram, time 0 and time 30 correspond to the 0 and 30 minutes incubation time.

The % of CYP2D6 involvement is calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an $IC_{50}$ higher than 6 µM for CYP2D6 activity, the $IC_{50}$ being the concentration of the compound that gives 50% of inhibition of the CYP2D6 activity.

Material and Methods:

Human liver microsomes (mixture of 20 different donors, mixed gender) are acquired from Human Biologics (Scottsdale, Ariz.). β-NADPH is purchased from Sigma (St Louis, Mo.). Bufuralol is purchased from Ultrafine (Manchester, UK). All the other reagents and solvents are of analytical grade.

Microsomal incubation mixture (total volume 0.1 mL) contains bufuralol 10 µM, β-NADPH (2 mM), microsomal proteins (0.5 mg/mL), and the new chemical entity (NCE) (0, 5, and 25 µM) in 100 mM sodium phosphate buffer pH 7.4. The mixture is incubated in a shaking waterbath at 37° C. for 5 minutes. The reaction is terminated by the addition of methanol (75 µL). The samples are vortexed and the denaturated proteins are removed by centrifugation. The supernatant is analyzed by liquid chromatography connected to a fluorescence detector. The formation of the 1'-hydroxybufuralol is monitored in control samples (0 µM NCE) and in the samples incubated in presence of the NCE. The stock solution of NCE is prepared in a mixture of Acetonitrile/Water to reach a final concentration of acetonitrile in the incubation below 1.0%.

The determination of 1'hydroxybufuralol in the samples is performed by liquid chromatography with fluorimetric detection as described below. Twenty five µL samples are injected onto a Chromolith Performance RP-18e column (100 mm×4.6 mm) (Merck KGAa, Darmstadt, Germany). The mobile phase, consisting of a mixture of solvent A and solvent B whose proportions change according the following linear gradient, is pumped through the column at a flow rate of 1 mL/min:

| Time (minutes) | Solvent A (%) | Solvent B (%) |
|---|---|---|
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consist of a mixture of 0.02 M potassium dihydrogenophosphate buffer pH3/methanol in the proportion 90/10 (v/v) for solvent A and 10/90 (v/v) for solvent B. The run time is 7.5 minutes. Formation of 1'-hydroxybufuralol is monitored by fluorimetric detection with extinction at λ 252 nm and emission at λ 302 nm.

The $IC_{50}$ of the NCE for CYP2D6 is calculated by the measurement of the percent of inhibition of the formation of the 1'-hydroxybufuralol in presence of the NCE compared to control samples (no NCE) at a known concentration of the NCE.

The percent of inhibition of the formation of the 1'-hydroxybufuralol is calculated as follows:

$$\frac{(1'\text{-hydroxybufuralol formed without inhibitor}) - (1'\text{-hydroxybufuralol formed with inhibitor})}{(1'\text{-hydroxybufuralol area formed without inhibitor})}$$

The $IC_{50}$ is calculated from the percent inhibition of the formation of the 1'-hydroxybufuralol as follows (assuming competitive inhibition):

$$\frac{NCE \text{ Concentration} \times (100 - \text{Percent of inhibition})}{\text{Percent of inhibition}}$$

The $IC_{50}$ estimation is assumed valid if inhibition is between 20% and 80% (Moody G C, Griffin S J, Mather A N, McGinnity D F, Riley R J. 1999. Fully automated analysis of activities catalyzed by the major human liver cytochrome P450 (CYP) enzymes: assessment of human CYP inhibition potential. Xenobiotica, 29(1): 53-75).

The invention claimed is:

1. A compound of formula (VI)

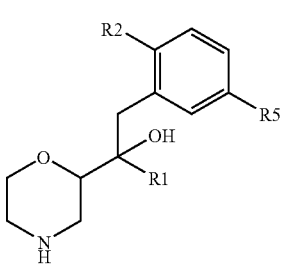

wherein,
- R1 is C1-C6 alkyl optionally substituted with 1, 2 or 3 fluorine atoms, or C3-C6 cycloalkyl wherein one C—C bond within the cycloalkyl moiety is optionally substituted by an O—C bond;
- R2 is C1-C4 alkyl optionally substituted with 1, 2 or 3 fluorine atoms, C1-C4 alkoxy optionally substituted with 1, 2 or 3 fluorine atoms, or phenyl optionally substituted with 1, 2 or 3 fluorine atoms; and R5 is H or F; or a pharmaceutically acceptable salt thereof.

2. The compound according to claim 1 of the formula

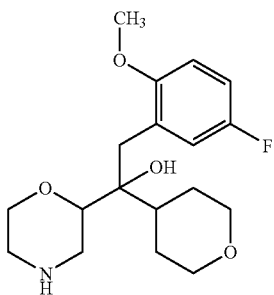

or a pharmaceutically acceptable salt thereof.

3. The compound according to claim 2 of the formula

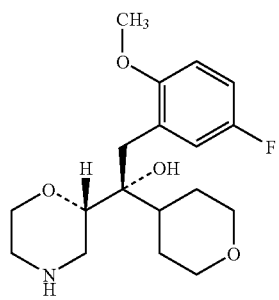

or a pharmaceutically acceptable salt thereof.

4. The hydrochloride salt of a compound according to claim 3.

5. A pharmaceutical composition, comprising a compound according to claim 1, or a pharmaceutically acceptable salt thereof, together with a pharmaceutically acceptable diluent, excipient or carrier.

6. The hydrochloride salt of a compound according to claim 2.

7. A pharmaceutical composition, comprising a compound according to claim 3, or a pharmaceutically acceptable salt thereof, together with a pharmaceutically acceptable diluent, excipient or carrier.

8. The pharmaceutical composition of claim 7, where said pharmaceutically acceptable salt is a hydrochloride salt.

* * * * *

UNITED STATES PATENT AND TRADEMARK OFFICE
CERTIFICATE OF CORRECTION

PATENT NO. : 7,423,037 B2
APPLICATION NO. : 10/577841
DATED : September 9, 2008
INVENTOR(S) : Gordon Iain Campbell et al.

It is certified that error appears in the above-identified patent and that said Letters Patent is hereby corrected as shown below:

In the issued patent, please note the following corrections:

<u>On Title page should read,</u>

Insert Item    -- [60]    Related U.S. Application Data

Provisional application No. 60/535,459, filed on January 9, 2004 --

Signed and Sealed this

Nineteenth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,423,037 B2 | Page 1 of 1 |
| APPLICATION NO. | : 10/577841 | |
| DATED | : September 9, 2008 | |
| INVENTOR(S) | : Gordon Iain Campbell et al. | |

It is certified that error appears in the above-identified patent and that said Letters Patent is hereby corrected as shown below:

On the first page of the specification, insert the following cross-reference after the title:

--This is the national phase application, under 35 USC 371, for PCT/US2004/032771, filed 28 October 2004, which claims the benefit, under 35 USC 119(e), of GB provisional applications 0326148.4 filed 10 November 2003 and US provisional application 60/535,459 filed 09 January 2004.--

Signed and Sealed this
Twenty-ninth Day of March, 2011

David J. Kappos
*Director of the United States Patent and Trademark Office*